(12) United States Patent
Gingeras et al.

(10) Patent No.: US 6,924,094 B1
(45) Date of Patent: *Aug. 2, 2005

(54) CHIP-BASED SPECIES IDENTIFICATION AND PHENOTYPIC CHARACTERIZATION OF MICROORGANISMS

(75) Inventors: Thomas R. Gingeras, Encinitas, CA (US); David Mack, Menlo Park, CA (US); Mark S. Chee, Palo Alto, CA (US); Anthony J. Berno, San Jose, CA (US); Lubert Stryer, Stanford, CA (US); Ghassan Ghandour, Atherton, CA (US); Ching Wang, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 09/724,938

(22) Filed: Nov. 28, 2000

Related U.S. Application Data

(63) Continuation of application No. 08/797,812, filed on Feb. 7, 1997, now Pat. No. 6,228,575, which is a continuation-in-part of application No. 08/629,031, filed on Apr. 8, 1996, now abandoned.
(60) Provisional application No. 60/017,765, filed on May 15, 1996, provisional application No. 60/012,631, filed on Mar. 1, 1996, and provisional application No. 60/011,339, filed on Feb. 8, 1996.

(51) Int. Cl.[7] .............................. C12Q 1/70; C12Q 1/68
(52) U.S. Cl. ................................. 435/5; 435/6
(58) Field of Search .............................. 435/5, 6, 91.2; 436/94

(56) References Cited

U.S. PATENT DOCUMENTS 3,817,837 A    6/1974  Rubenstein et al. .. 195/103.5 R
3,850,752 A   11/1974  Schuurs et al. ....... 195/103.5 R
3,939,350 A    2/1976  Kronic et al. ............... 250/365
3,996,345 A   12/1976  Ullman et al. ................ 424/12
4,275,149 A    6/1981  Litman et al. ................. 435/7

(Continued)

FOREIGN PATENT DOCUMENTS

| EP | 0 543 550 A1 | 5/1993 |
|---|---|---|
| WO | 89/10977 | 11/1989 |
| WO | 90/15070 | 12/1990 |
| WO | 92/10092 | 6/1992 |
| WO | WO 92/10588 A1 | 6/1992 |
| WO | 94/10128 | 5/1994 |
| WO | 94/12305 | 6/1994 |
| WO | 95/11995 | 5/1995 |

OTHER PUBLICATIONS

Favre, N., "Supplementary European Search Report," 5 pages, European Patent Office, Munich, Switzerland (Sep. 2, 2004).

Bugawan, T.L., et al., "A method for typing polymorphism at the HLA–A locus using PCR amplification and immobilized oligonucleotide probes," *Tissue Antigens* 44:137–147, Munksgaard, Copenhagen, Denmark (1994).

(Continued)

*Primary Examiner*—Kenneth R. Horlick
(74) *Attorney, Agent, or Firm*—Morgan Lewis & Bockius LLP; Sandra E. Wells

(57) ABSTRACT

This invention provides oligonucleotide based arrays and methods for speciating and phenotyping organisms, for example, using oligonucleotide sequences based on the *Mycobacterium tubercluosis rpoB* gene. The groups or species to which an organism belongs may be determined by comparing hybridization patterns of target nucleic acid from the organism to hybridization patterns in a database.

12 Claims, 34 Drawing Sheets

Fingerprints of Mycobacterium Species

M. avium    M. gordonae    M. chelonae

M. kansasii    M. scrofulaceum    M. xenopi

M. avim/intracellulare    M. tuberculosis

U.S. PATENT DOCUMENTS

| | | | |
|---|---|---|---|
| 4,277,437 A | 7/1981 | Maggio | 422/61 |
| 4,366,241 A | 12/1982 | Tom et al. | 435/7 |
| 5,143,854 A | 9/1992 | Pirrung et al. | 436/518 |
| 5,384,261 A | 1/1995 | Winkler et al. | 436/518 |
| 5,424,186 A | 6/1995 | Fodor et al. | 435/6 |
| 5,429,807 A | 7/1995 | Matson et al. | 422/131 |
| 5,436,327 A | 7/1995 | Southern et al. | 536/25.34 |
| 5,445,934 A | 8/1995 | Fodor et al. | 435/6 |
| 5,545,531 A | 8/1996 | Rava et al. | 435/6 |
| 5,547,839 A | 8/1996 | Dower et al. | |
| 5,700,637 A | 12/1997 | Southern | 435/6 |
| 5,795,716 A | 8/1998 | Chee et al. | 435/6 |
| 5,800,992 A | 9/1998 | Fodor et al. | 435/6 |
| 5,837,832 A | 11/1998 | Chee et al. | 536/22.1 |
| 5,861,242 A | 1/1999 | Chee et al. | 435/5 |

OTHER PUBLICATIONS

Gress, T.M., et al., "Hybridization fingerprinting of high–density cDNA–library arrays with cDNA pools derived from whole tissues," *Mammalian Genome* 3:609–619, Springer–Verlag, New York, New York (1992).

Barringer et al., "Blunt–end and single–strand ligations by *Escherichia coli* ligase: influence on an in vitro amplification scheme", *Gene,* vol. 89, 1990, pp. 117–122.

Beattie et al., "Genosensor Technology", *Clin. Chemistry,* vol. 39, No. 4, 1993, pp. 719–722.

Bloch et al., "Nationwide Survey of Drug–Resistant Tuberculosis in the United States", *JAMA,* vol. 271, No. 9, Mar. 2, 1994, pp. 665–671.

Chetverin et al., "Oligonucleotide Arrays: New Concepts and Possibilities", *Bio/Technology,* vol. 12, Nov. 1994, pp. 1093–1099.

Elder, "Analysis of DNA Oligonucleotide Hybridization Data by Maximum Entropy", *Proceedings of the Twelfth International Workshop on Maximum Entropy and Bayesian Methods.* Kluwer Academic Publishers. 1992.

Fodor et al., Light–Directed Spatially Addressable Parallel Chemical Synthesis *Science,* vol. 251, 1991, pp. 767–773.

Fodor et al., "Multiplexed biochemical assays with biological chips", *Nature,* vol. 364, Aug. 5, 1993, pp. 555–556.

Felmlee et al., "Genotypic Detection of *Mycobacterium tuberculosis* Rifampin Resistance: Comparison of Single–Strand Conformation Polymorphism and Dideoxy Fingerprinting", *Jrnl. of Clin. Microbiology,* vol. 33, No. 6, 1995, pp. 1617–1623.

Gingeras et al., Simultaneous Genotyping and Species Identification Using Hybridization Pattern Recognition Analysis of Generic Mycobacterium DNA Arrays, *Genome Research,* vol. 8, 1998, pp. 435–448.

Guatelli et al., "Isothermal, in vitro amplification of nucleic acids by a multienzyme reaction modeled after retroviral replication", *Proc. Natl. Acad. Sci. USA,* vol. 87, Mar. 1990, pp. 1874–1878.

Hughes et al., "Identification of Mycobacteria from Animals by Restriction Enzyme Analysis and Direct DNA Cycle Sequencing of Polymerase Chain Reaction–Amplified 16S rRNA Gene Sequences", *Jrnl. of Clin. Microbiology,* Dec. 1993, pp. 3216–3222.

Hoffner, "Pulmonary Infections Caused by Less Frequently Encountered Slow–Growing Environmental Mycobacteria", *Eur. Jrnl. Clin., Microbiol. Infect. Dis.,* vol. 13, No. 11, Nov. 1994, pp. 937–941.

Hunt et al., "Detection of a Genetic Locus Encoding Resistance to Rifampin in Mycobacterial Cultures and in Clinical Specimens", *Diagn. Microbiol. Infect. Dis.,* vol. 18, 1994, pp. 219–227.

Jonas et al., "Detection and Identification of *Mycobacterium tuberculosis* Directly from Sputum Sediments by Amplification of rRNA", *Jrnl. of Clin. Microbiology,* Sep. 1993, pp. 2410–2416.

Kanal, "Patterns in Pattern Recognition", *IEEE Trans. Info. Theory,* 1974, pp. IT–20(6): 697–722.

Kapur et al., "Rapid Mycobacterium Species Assignment and Unambiguous Identification of Mutations Associated with Antimicrobial Resistance in *Mycobacterium tuberculosis* by Automated DNA Sequencing", *Arch. Pathol. Lab. Med.,* Feb. 1995, vol. 119, pp. 131–138.

Kox et al., "PCR Assay Based on DNA Coding for 16S rRNA for Detection and Identification of Mycobacteria in Clinical Samples", *Jrnl. Clin.. Microbiol.,* 1995 pp. 33(12): 3225–3233.

Kwoh et al., "Transcription–based amplification system and detection of amplified human immunodeficiency virus type 1 with a bead–based sandwich hybridization format", *Proc. Natl. Acad. Sci. USA,* vol. 86, Feb. 1989, pp. 1173–1177.

Landegren et al., "A Ligase–Mediated Gene Detection Technique", *Science,* vol. 241, Aug. 26, 1988, pp. 1077–1080.

Lipschutz et al., "Using Oligonucleotide Probe Arrays To Access Genetic Diversity", *Biotechniques,* vol. 19, No. 3, Sep. 1995, pp. 442–447.

Lipshutz, *Clin. Chem.* vol. 40, No. 6, 1994 abstract, p. 1173.

Musser, "Antimicrobial Agent Resistance in Mycobacteria: Molecular Genetic Insights", *Clin. Microbiology Reviews,* Oct. 1995, pp. 496–514.

Pease et al., "Light–generated oligonucleotide arrays for rapid DNA sequence analysis", *Proc. Natl. Acad. Sci. U.S.A.,* vol. 91, May 1994, pp. 5022–5026.

Plikaytis et al., "Differentiation of Slowly Growing Mycobacterium Species, Including *Mycobacterium tuberculosis* by Gene Amplification and Restriction Fragment Length Polymorphism Analysis", *Jrnl. of Clin. Microbiology,* Jul. 1992, pp. 1815–1822.

Salazar et al., "Nucleic acid scanning–by–hybridization of enterohemorrhagic *Exchericha coli* isolates using oligodeoxynucleotide arrays", *Nucleic Acids Res,* vol. 24, No. 24, 1996, pp. 5056–5057.

Schirm et al., "Comparison of Amplicor, In–House PCR, and Conventional Culture for Detection of *Mycobacterium tuberculosis* in Clinical Samples", *Jrnl. of Clin. Microbiology,* 1995, pp. 3221–3224.

Sewell et al, "Comparison of the Septi–Chek AFB and BACTEC Systems and Conventional Culture for Recovery of Mycobacteria", *Jrnl. of Clin. Microbiology,* Oct. 1993, pp. 2689–2691.

Schafer et al., "*Mycobacterium xenopi, Mycobacterium fortuitum, Mycobacterium kansasii,* and Other Nontuberculous Mycobacteria in an Area of Endemicity for AIDS", *Clin. Infectious Diseases,* 1992, pp. 161–162.

Southern et al., "Analyzing and Comparing Nucleic Acid Sequences by Hybridization to Arrays of Oligonucleotides: Evaluation Using Experimental Models", *Genomics 13,* 1992, pp. 1008–1017.

Small et al., "Molecular Epidemiology of Tuberculosis", *Tuberculosis: Pathogenesis, Protection and Control,* 1994, pp. 569–582.

Stager et al., "Role of Solid Media When Used in Conjunction with the BACTEC Systems for Mycobacterial Isolation and Identification", *Jrnl. Clin.. Microbiol.,* Jan. 1991, pp. 154–157.

Telenti et al., "Detection of rifampicin–resistance mutations in *Mycobacterium tuberculosis*", *The Lancet,* vol. 341, Mar. 13, 1993, pp. 647–650.

Van der Viliet et al., "Nucleic acid sequence–based amplification (NASBA) for the identification of mycobacteria", *Jrnl. of General Microbiology,* vol. 139, 1993, pp. 2423–2429.

Wolinsky, "Mycobacterial Diseases Other Than Tuberculosis", *Clin. Infectious Diseases,* vol. 15, 1992, pp. 1–12.

Wu et al., "The Litigation Amplification Reaction (LAR)—Amplification of Specific DNA Sequences Using Sequential Rounds of Template–Dependent Ligation", *Genomics 4,* 1989, pp. 560–569.

Whelen et al., "Direct Genotypic Detection of *Mycobacterium tuberculosis* Rifampin Resistance in Clinical Specimens by Using Single–tube Heminested PCR", *Jrnl. of Clin. Microbiology,* vol. 33, No. 3, 1995, pp. 556–561.

$n_1 n_2 n_3 n_4 n_5$
A C T G T T A G C T A A T T G G —— REF. SEQ.

|  | | | | | |
|---|---|---|---|---|---|
| A-LANE | TGAC | GAAA | AGAA | CAAT | AAAG |
| C-LANE | TGCC | GACA | ACCA | CACT | AACG |
| G-LANE | TGGC | GAGA | ACGA | CAGT | AAGG |
| T-LANE | TGTC | GATA | ACTA | CATT | AATG |
|  | $i_1$ | $i_2$ | $i_3$ | $i_4$ | $i_5$ |
| WT. LANE | TGAC | GACA | ACAA | CAAT | AATG |

FIG. 4

CORRESPONDING NUCLEOTIDE
n
ACTGTTAGCTAATTGG—REF. SEQ.
　　　　CAATCGA ——— PROBE FROM FIRST SET
　　　　CAA-CGAT ——— DELETION PROBE
　　　　CAATACGA ⎫
　　　　CAATCCGA ⎬ INSERTION
　　　　CAATGCGA ⎪ PROBES
　　　　CAATTCGA ⎭

FIG. 5

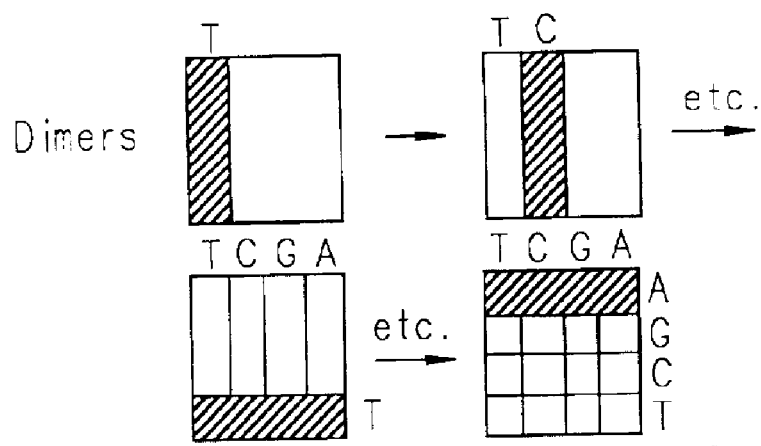
In polynomial notation: $(T+C+A+G)^2 = $ All dimers
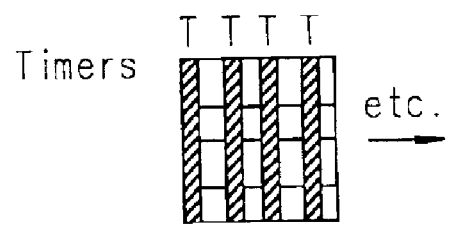
FIG. 7

Tiling Strategy for Sequence Determination

| Non Coding Sequences | | | | | | | Coding Sequences | | | | | | | | | | | | | | |
|---|---|---|---|---|---|---|---|---|---|---|---|---|---|---|---|---|---|---|---|---|---|
| -7 | -6 | -5 | -4 | -3 | -2 | -1 | 1 | 2 | 3 | 4 | 5 | 6 | 7 | 8 | 9 | 10 | 11 | 12 | 13 | 14 |
| | | | | | | | A | | | | | | | | | | | | | |
| | | | | | | | C | | | | | | | | | | | | | |
| | | | | | | | G | | | | | | | | | | | | | |
| | | | | | | | T | | | | | | | | | | | | | |
| | | | | | | | | A | | | | | | | | | | | | |
| | | | | | | | | C | | | | | | | | | | | | |
| | | | | | | | | G | | | | | | | | | | | | |
| | | | | | | | | T | | | | | | | | | | | | |
| | | | | | | | | | A | | | | | | | | | | | |
| | | | | | | | | | C | | | | | | | | | | | |
| | | | | | | | | | G | | | | | | | | | | | |
| | | | | | | | | | T | | | | | | | | | | | |
| | | | | | | | | | | A | | | | | | | | | | |
| | | | | | | | | | | C | | | | | | | | | | |
| | | | | | | | | | | G | | | | | | | | | | |
| | | | | | | | | | | T | | | | | | | | | | |
| | | | | | | | 1 | 2 | 3 | 4 | | | | | | | | | | |

FIG. 9

Fingerprints of Mycobacterium Species
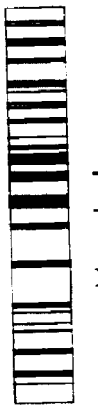
M. avium
M. gordonae
M. chelonae
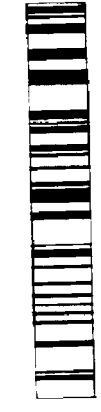
M. kansasii
M. scrofulaceum
M. xenopi
M. avim/intracellulare
M. tuberculosis
FIG. 14A

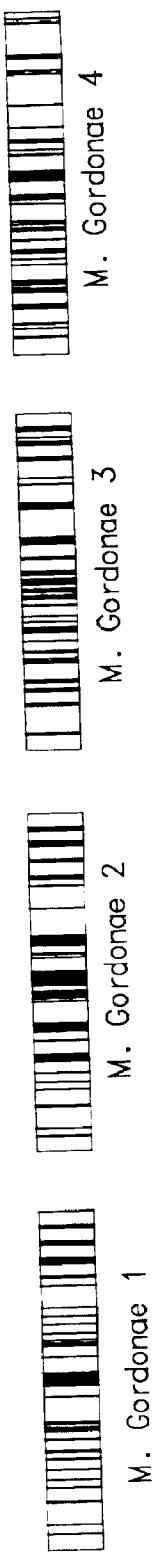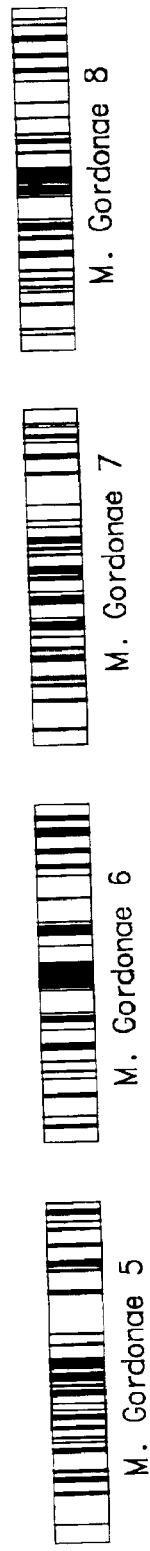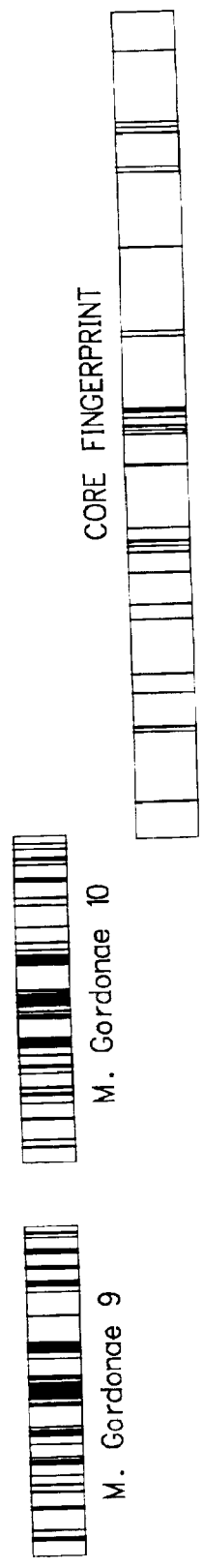
FIG. 15

GeneChip Sequences

| | 10 | 20 | 30 | 40 | 50 | |
|---|---|---|---|---|---|---|
| MTB.TXT | NCCCAGGACG | TGGAGGCGAT | CACACCGCAG | ACGTTGATCA | ACATCCGGCC | GGTGGTCGCC | 60
| GO-LB-MT.TXT | NCCCAGGACG | TGGAGGCGAT | CACACCGCAG | ACCGCATCA | ACATCCGGCG | GGTCGTCGCC |
| MTB.TXT | GCGATCAAGG | AGTTCTTCGG | CACCAGCCAG | CTGAGCCAAT | TCATGGACCA | GAACAACCCG | 120
| GO-LB-MT.TXT | GCGATCAAGG | AGTTCTTCGG | CACCAGCCAG | CCCAKGTGGN | TCATGGACCA | GAACAACCCG |
| MTB.TXT | CTGTCGGGGT | TGACCCACAA | GCGCCGACTG | TCGGCGCTGG | GGCCGGCGG | TCTGTCACGT | 180
| GO-LB-MT.TXT | CTGTCGGTTC | GGACCCACAA | GCGTDNTHYG | TCGGCGCTGG | GGTCGGTBG | TCTGTCCGT |
| MTB.TXT | GAGCGTGCCG | GCTGGGAGT | CCGCGACGTG | CACCCGTCGC | ACTACGGCCG | GATGTGCCCG | 240
| GO-LB-MT.TXT | GAGCGTGCG | GTGGNATDNA | ANNTCACGTG | CACCCGTCGC | ACTACGGNCS | CATGTGCCCG |
| MTB.TXT | ATCGAAACC | CTGAGGGGCC | CAACATCGGT | CTGATCGGCT | CGCTGTCGGT | GTACGCGCGG | 300
| GO-LB-MT.TXT | ATCGAGAAAT | KNGCCKNAGN | BNTHVTCGG | CTGATCGG | CGCTGTCGGT | GTACGCGCGG |
| MTB.TXT | GTCAACCCGT | TCGGGTTCAT | CGAAACGCCG | TACCGCAAGG | TGGTCGACGG | CGTGGTTAGC | 360
| GO-LB-MT.TXT | GTCAACCCGT | TCGGCTTCCA | VCNGNTNASN | NTNNTGBDGR | NGKGGNNSKC | NACCHGDBGT |
| MTB.TXT | GACGAGATCG | TGTACCTTGAC | CGCCGACGAG | CGCCGACCGCC | ACGTGGTGGC | ACAGGCCAAT | 420
| GO-LB-MT.TXT | GACGAGATCG | CNCVCHGCAC | CGCCGACGAG | CGCCGACCGCC | ACGTGGDGGC | GCCGWNCAAC |
| MTB.TXT | TCGCCGATCG | ATGCGGACGG | TCGCTTCGTC | GAGCCGACG | TGCTGGTCCG | CCGCAAGGCG | 480
| GO-LB-MT.TXT | TCGCCGNGNG | MCNCGCGNGD | GCTNCSTATT | GGGCCGACG | TTTCTGGTCCG | CCGCAGGGCG |
| MTB.TXT | GGCGAGGTGG | AGTACGTGCC | CTCGTCTGAG | GTGGACTACA | TGGACGTCTC | GCCCGCCAG | 540
| GO-LB-MT.TXT | GGCGAGGTGG | AGTACGTGCC | CTCGTCGAG | GTGGACTACA | TGGACGTCTC | CCGCGCCAG |
| MTB.TXT | ATGGTGTCGG | TGGCCACCGC | GATGATTCCC | TTCCTGGAGC | ACGACGACGC | CAACCGTGCC | 600
| GO-LB-MT.TXT | ATGGTGTCGG | TGGCACCGC | GATGATTCCG | DKCCBCSTAC | ACGACGACGC | CAACCGTGCC |
| MTB.TXT | CTCATGGGGG | CAAACATGCA | GCGCCAGGCG | GTGCCGCTGG | TCCGTAGCGA | GGCCCGCTG | 660
| GO-LB-MT.TXT | CTGGNNNTTC | DCMACATGCA | GCGCCAGGCG | GTTCCGGICN | TGSGCCNGHN | NGCACCGCTG |
| MTB.TXT | GTGGGCACCG | GCATGGAGCT | GCGGCGGCG | ATCGACGCGG | CGACGT | | 706
| GO-LB-MT.TXT | GTGGGCACCG | GCATGGAGT | GCGGCGGCG | ATCGACGCGG | CGAANV | |

*FIG. 16B*

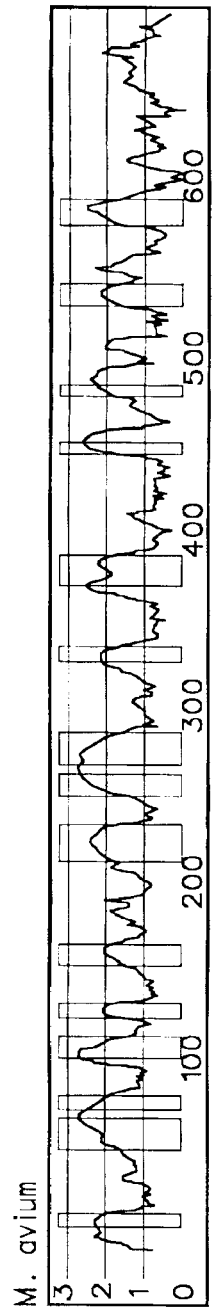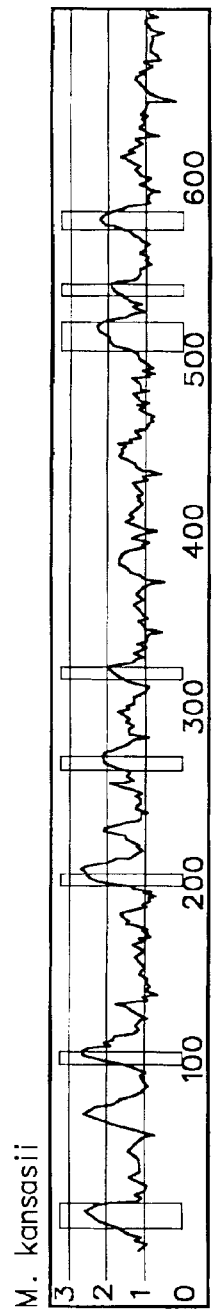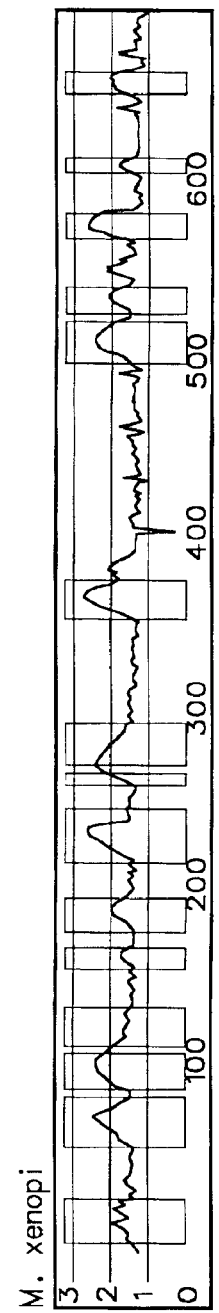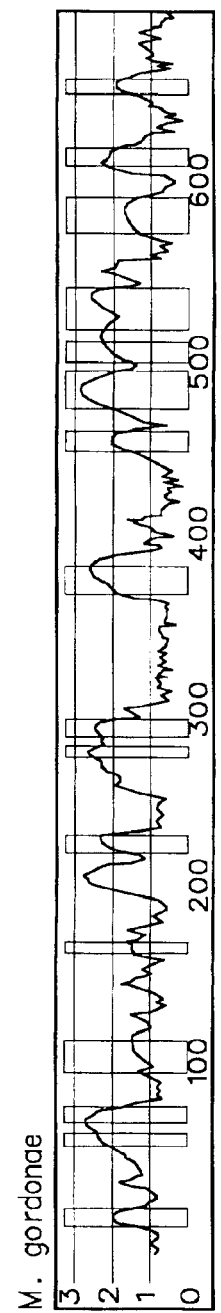
FIG. 17

FIG. 18
Mycobacteria Species vs. Mycobacterium tuberculosis

Mycobacterium tuberculosis vs. M. gordonae
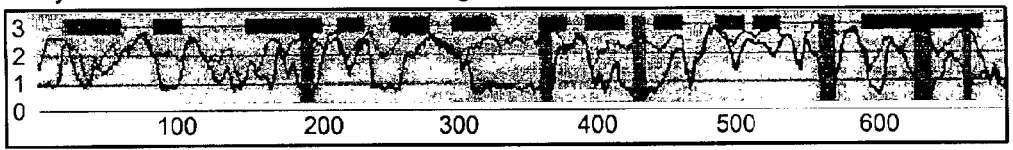

Mycobacterium tuberculosis vs. M. chelonae
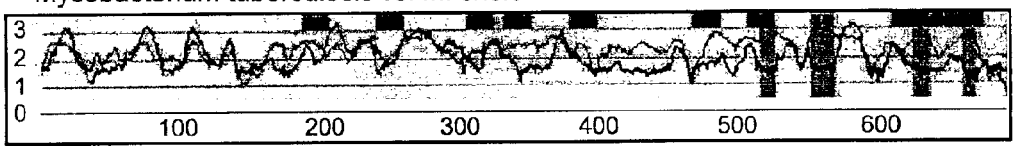

Mycobacterium tuberculosis vs. M. avium
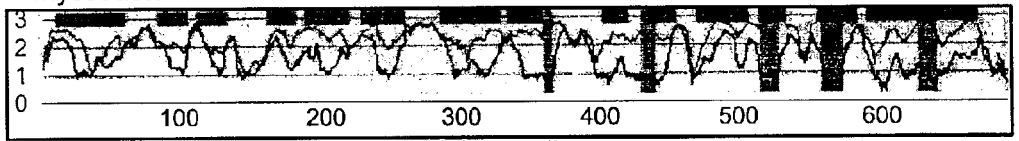

Mycobacterium tuberculosis vs. M. kansasii
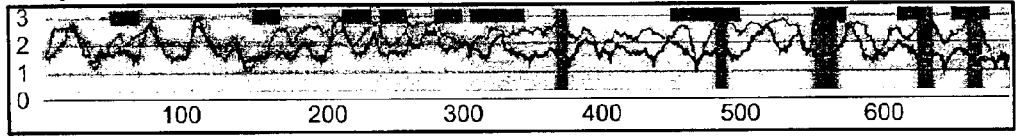

Mycobacterium tuberculosis vs. M. scrofulaceum
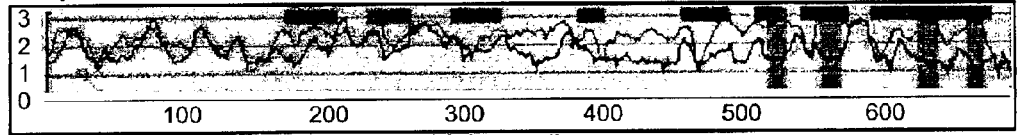

Mycobacterium tuberculosis vs. M. intracelluare
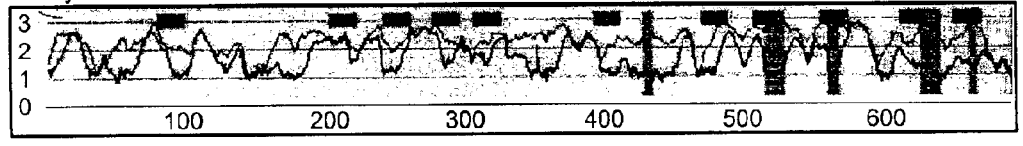

Mycobacterium tuberculosis vs. M. xenopi
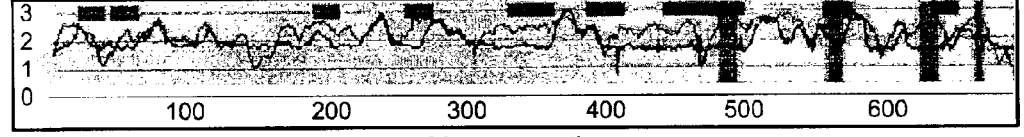

Mycobacterium tuberculosis vs. M. smegmatis
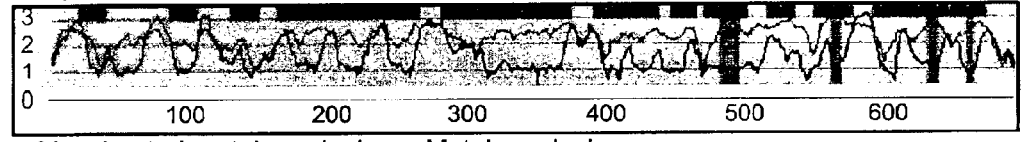

Mycobacterium tuberculosis vs. M. tuberculosis
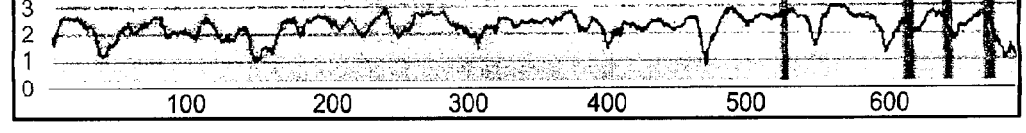

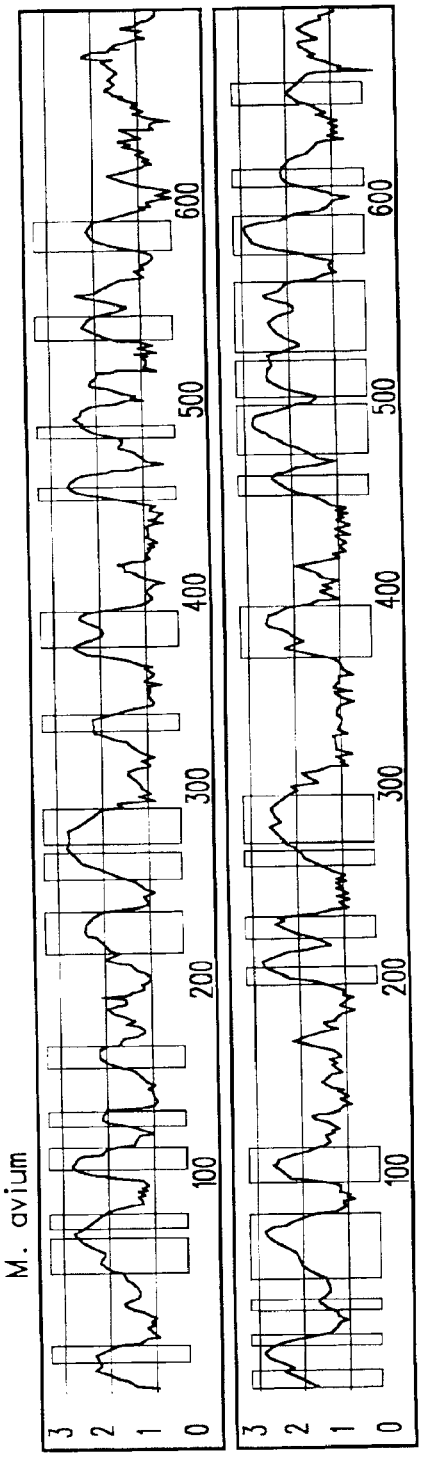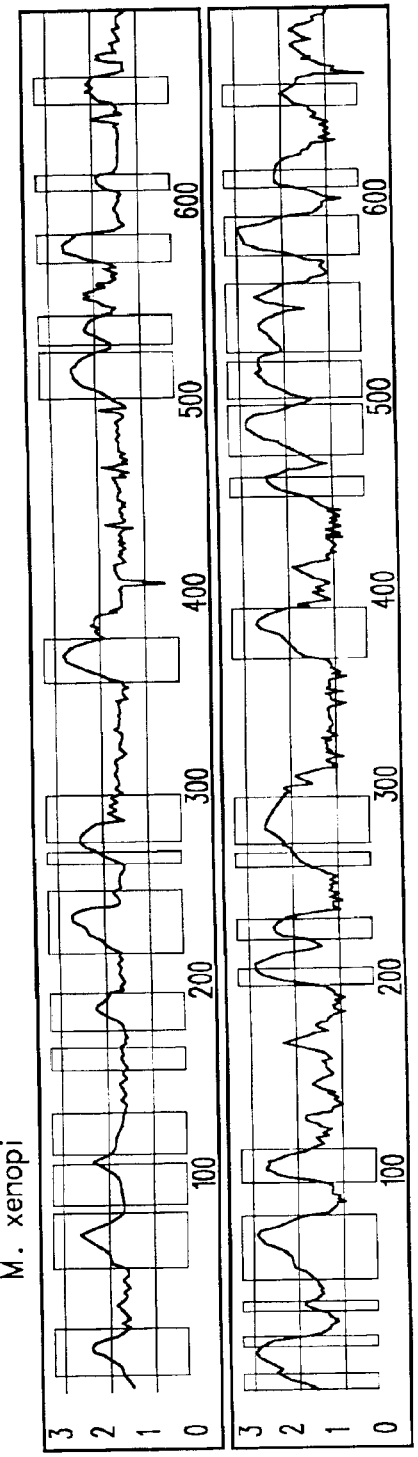
FIG. 19A
FIG. 19B

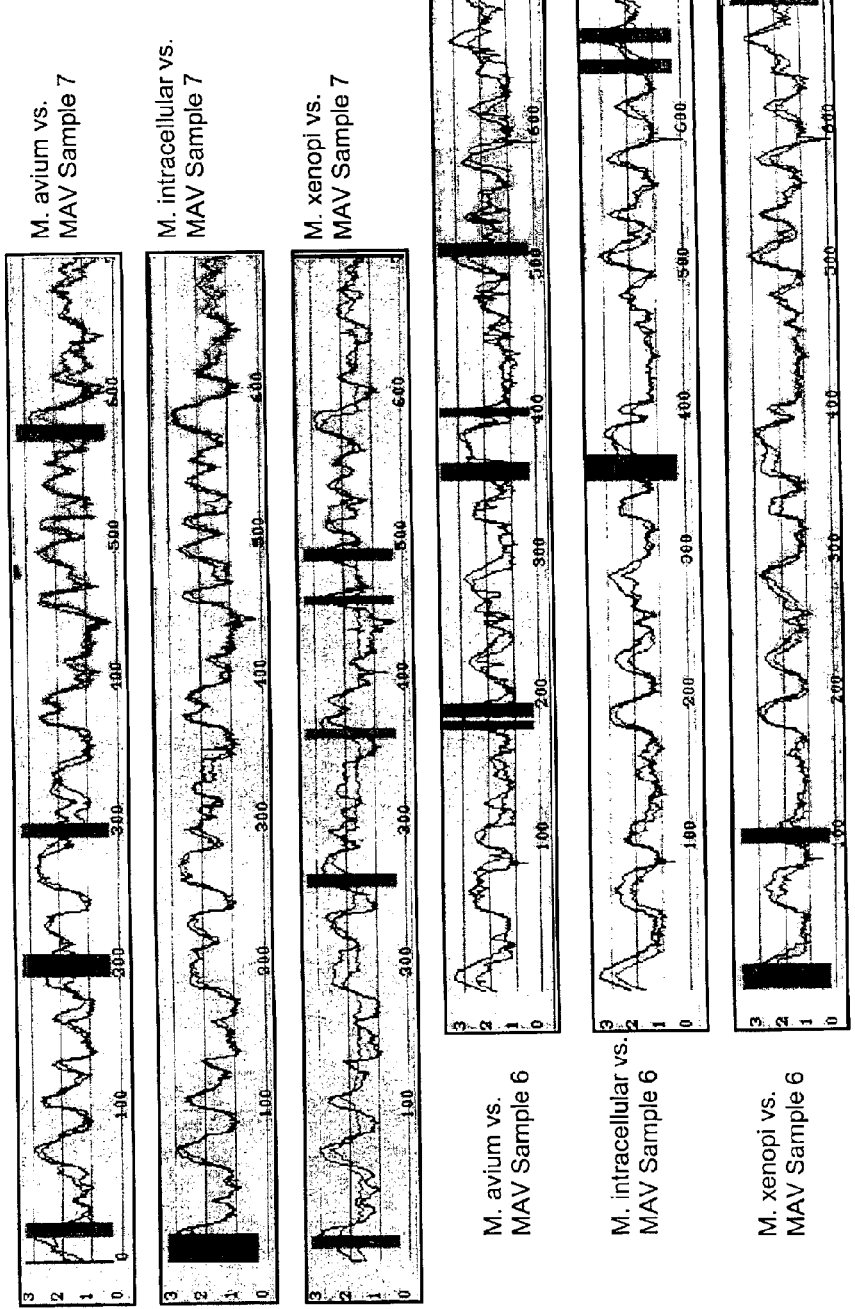

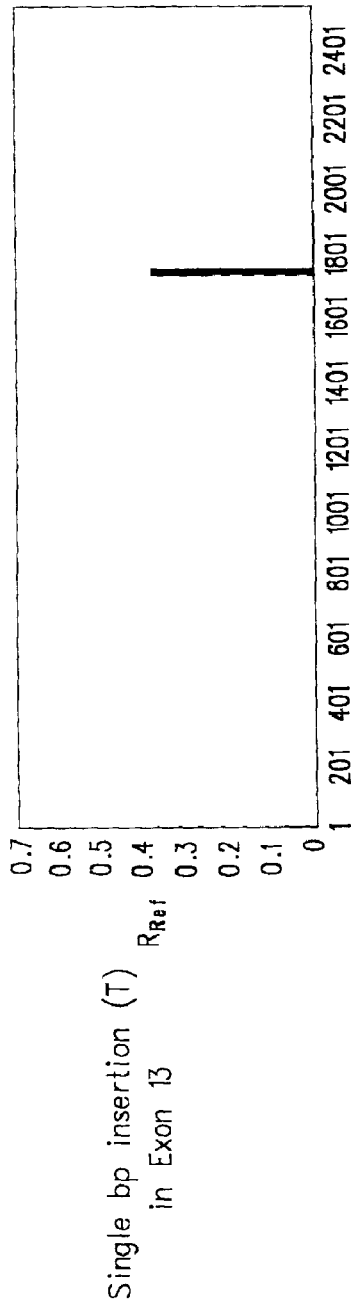
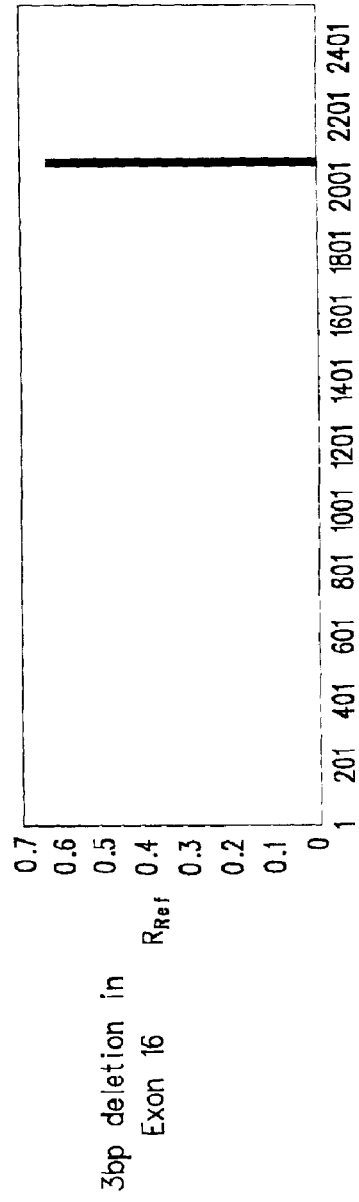
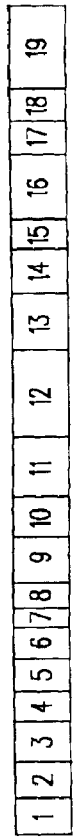
FIG. 28

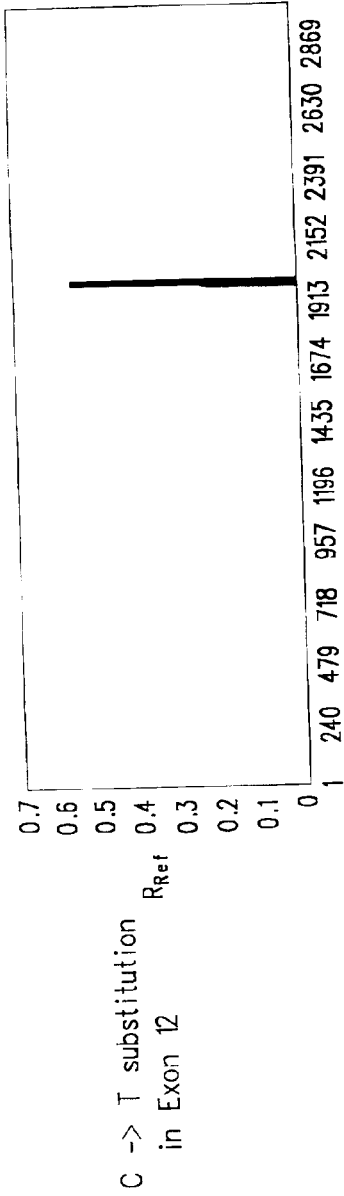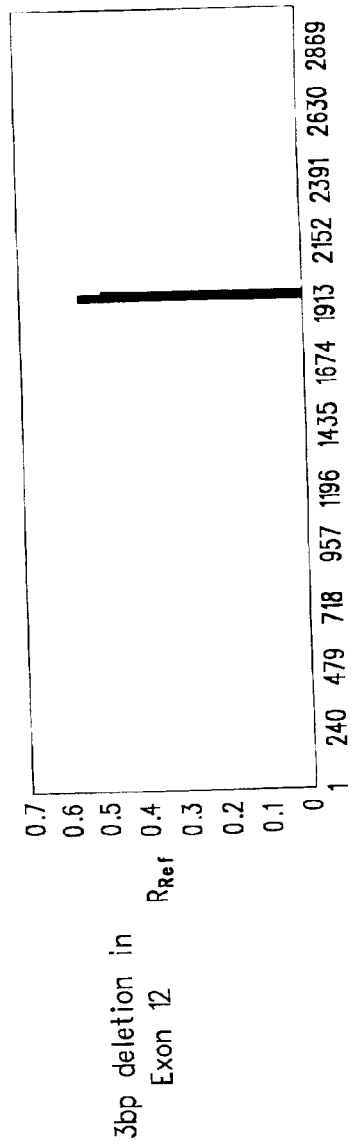
FIG. 29

CHIP-BASED SPECIES IDENTIFICATION AND PHENOTYPIC CHARACTERIZATION OF MICROORGANISMS

This application is a continuation of U.S. application Ser. No. 08/797,812 filed Sep. 7, 1997, now U.S. Pat. No. 6,228,575, which is a continuation in part of U.S. Ser. No. 08/629,031 filed Apr. 8, 1996 now abandoned, U.S. application Ser. No. 08/797,812 filed Sep. 7, 1997, now U.S. Pat. No. 6,228,575, claims the benefit of priority of U.S. Provisional application Ser. No. 60/017,765 filed May 15, 1996, and U.S. Ser. No. 08/629,031 filed Apr. 8, 1996 claims the benefit of priority of U.S. provisional application Ser. No. 60/011,339 filed Feb. 8, 1996 and U.S. provisional application Ser. No. 60/012,31 filed Mar. 1, 1996.

BACKGROUND OF THE INVENTION

Copyright Notice

A portion of the disclosure of this patnet document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

Field of the Invention

This invention relates to the identification and characterization of microorganisms.

Background of the Invention

Multidrug resistance and human immunodeficiency virus (HIV-1) infections are factors which have had a profound impact on the tuberculosis problem. An increase in the frequency of *Mycobacterium tuberculosis* strains resistant to one or more anti-mycobacterial agents has been reported, Block, et al., (1994) JAMA 271:665–671. Immunocompromised HIV-1 infected patients not infected with *M. tuberculosis* are frequently infected with *M. avium* complex (MAC) or *M. avium-M. intracellulare* (MAI) complex. These mycobacteria species are often resistant to the drugs used to treat *M. tuberculosis*. These factors have re-emphasized the importance for the accurate determination of drug sensitivities and mycobacteria species identification.

In HIV-1 infected patients, the correct diagnosis of the mycobacterial disease is essential since treatment of *M. tuberculosis* infections differs from that called for by other mycobacteria infections, Hoffner, S. E. (1994) *Eur. J. Clin. Microbiol. Inf. Dis.* 13:937–941. Non-tuberculosis mycobacteria commonly associated with HIV-1 infections include *M. kansasii, M. xenopi, M. fortuitum, M. avium* and *M. intracellular*, Wolinsky, E., (1992) *Clin. Infect. Dis.* 15:1–12, Shafer, R. W. and Sierra, M. F. 1992 *Clin. Infect. Dis.* 15:161–162. Additionally, 13% of new cases (HIV-1 infected and non-infected) of *M. tuberculosis* are resistant to one of the primary anti-tuberculosis drugs (isoniazid [INH], rifampin [RIF], streptomycin [STR], ethambutol [EMB] and pyrazinamide [PZA] and 3.2% are resistant to both RIF and INH, Block, et al., *JAMA* 271:665–671, (1994). Consequently, mycobacterial species identification and the determination of drug resistance have become central concerns during the diagnosis of mycobacterial diseases.

Methods used to detect, and to identify *Mycobacterium* species vary considerably. For detection of *Mycobacterium tuberculosis*, microscopic examination of acid-fast stained smears and cultures are still the methods of choice in most microbiological clinical laboratories. However, culture of clinical samples is hampered by the slow growth of mycobacteria. A mean time of four weeks is required before sufficient growth is obtained to enable detection and possible identification. Recently, two more rapid methods for culture have been developed involving a radiometric, Stager, C. E. et al., (1991) *J. Clin. Microbiol.* 29:154–157, and a biphasic (broth/agar) system Sewell, et al., (1993) *J. Clin. Microbiol,* 29:2689–2472. Once grown, cultured mycobacteria can be analyzed by lipid composition, the use of species specific antibodies, species specific DNA or RNA probes and PCR-based sequence analysis of 16S rRNA gene (Schirm, et al. (1995) *J. Clin. Microbiol,* 33:3221–3224; Kox, et al. (1995) *J. Clin. Microbiol.* 33:3225–3233) and IS6110 specific repetitive sequence analysis (For a review see, e.g., Small et al., P. M. and van Embden, J. D. A. (1994) *Am. Society for Microbiology,* pp. 569–582). The analysis of 16S rRNA sequences (RNA and DNA) has been the most informative molecular approach to identify *Mycobacteria* species (Jonas, et al., *J. Clin. Microbiol,* 31:2410–2416 (1993)). However, to obtain drug sensitivity information for the same isolate, additional protocols (culture) or alternative gene analysis is necessary.

To determine drug sensitivity information, culture methods are still the protocols of choice. *Mycobacteria* are judged to be resistant to particular drugs by use of either the standard proportional plate method or minimal inhibitory concentration (MIC) method. However, given the inherent lengthy times required by culture methods, approaches to determine drug sensitivity based on molecular genetics have been recently developed.

Table 1 lists the *M. tuberculosis* genes with which when mutated have been shown to confer drug resistance (other genes are know, e.g., the pncA gene). Of the drugs listed in Table 1, RIF and INH form the backbone of tuberculosis treatment. Detection of RIF resistance in *M. tuberculosis* is important not only because of its clinical and epidemiological implications but also because it is a marker for the highly threatening multidrug resistant phenotype (Telenti, et al. (1993) *The Lancet* 341:647–650). Of the drug resistances listed in Table 1, decreased sensitivity to RIF is the best understood on a genetic basis.

TABLE 1

*M. tuberculosis* Genes with Mutations Which Confer Drug Resistance

| Drug | Gene | Size (bp) | Gene Product |
|---|---|---|---|
| RIF | rpoB | 3,534 | β-subunit of RNA polymerase |
| INH | katG | 2,205 | catalase-peroxidase |
| INH-ETH | inhA | 810 | fatty and biosynthesis |
| STR | rpsL | 372 | ribosomal protein S12 |
|  | rrs | 1,464 | 16S rRNA |
| FQ | gyrA | 2,517 | DNA gyrase A subunit |

Because resistance to RIF is *E. coli* strains was observed to arise as a result of mutations in the rpoB gene, Telenti, et al., id., identified a 69 base pair (bp) region of the *M. tuberculosis rpoB* gene as the locus where RIF resistant mutations were focused. Kapur, et al., (1995) *Arch Pathol. Lab. Med.* 119:131–138, identified additional novel mutations in the *M. tuberculosis rpoB* gene which extended this core region to 81 bp. In a detailed review on antimicrobial agent resistance in mycobacteria, Musser {*Clin. Microbiol. Rev.,* 8:496–514 (1995)], summarized all the characterized mutations and their relative frequency of occurrence in this 81 bp region of rpoB. Missense mutations comprise 88% of all known mutations while insertions (3 or 6 bp) and deletions (3, 6 and 9 bp) account for 4% and 8% of the remaining mutations, respectively. Approximately 90% of all RIF resistant tuberculosis isolates have been shown to have mutations in this 81 bp region. The remaining 10% are thought possibly to involve genes other than rpoB.

For the above reasons, it would be desirable to have simpler methods which identify and characterize microorganisms, such as *Mycobacteria*, both at the phenotypic and genotypic level. This invention fulfills that and related needs.

SUMMARY OF THE INVENTION

The present invention provides systems, methods, and devices for characterizing and identifying organisms. In one aspect of the invention, a method for identifying a genotype of a first organism, comprising:

(a) providing an array of oligonucleotides at known locations on a substrate, said array comprising probes complementary to reference DNA or RNA sequences from a second organism;

(b) hybridizing a target nucleic acid sequence from the first organism to the array; and (c) based on an overall hybridization pattern of the target to the array, identifying the genotype of the first organism, and optionally identifying a phenotype of the first organism.

Another aspect of the invention provides a method for identifying the genotype and/or phenotype of an organism by comparing a target nucleic acid sequence from a first organism coding for a gene (or its complement) to a reference sequence coding for the same gene (or its complement) from a second organism, the method comprising:

(a) hybridizing a sample comprising the target nucleic acid or a subsequence thereof to an array of oligonucleotide probes immobilized on a solid support, the array comprising:

a first probe set comprising a plurality of probes, each probe comprising a segment of nucleotides exactly complementary to a subsequence of the reference sequence, the segment including at least one interrogation position complementary to a corresponding nucleotide in the reference sequence;

(b) determining which probes in the first probe set bind to the target nucleic acid or subsequence thereof relative to their binding to the reference sequence, such relative binding indicating whether a nucleotide in the target sequence is the same or different from the corresponding nucleotide in the reference sequence;

(c) based on differences between the nucleotides of the target sequence and the reference sequence identifying the phenotype of the first organism;

(d) deriving one or more sets of differences between the reference sequence and the first organism; and (e) comparing the set of differences to a data base comprising sets of differences correlated with speciation of organisms to identify the genotype of the first organism.

Another aspect of the invention provides a method for identifying the genotype and/or phenotype of an organism by comparing a target nucleic acid sequence from a first organism coding for a gene (or its complement) to a reference sequence coding for the same gene (or its complement) from a second organism, the method comprising:

(a) hybridizing a sample comprising the target nucleic acid or a subsequence thereof to an array of oligonucleotide probes immobilized on a solid support, the array comprising:

a first probe set comprising a plurality of probes, each probe comprising a segment of nucleotides exactly complementary to a subsequence of the reference sequence, the segment including at least one interrogation position complementary to a corresponding nucleotide in the reference sequence, wherein each interrogation position corresonds to a nucleotide position in the reference or target sequence;

(b) determining a hybridization intensity from each probe;

(c) plotting the hybridization intensities versus the nucleotide position corresponding to the probe from which the hybridization intensity was determined to derive a target plot of hybridization intensity;

(d) repeating steps (a)–(c) with the target sequence replaced by the reference sequence, to derive a baseline plot of the reference sequence; and (e) comparing the target plot to the baseline plot to identify the genotype and/or phenotype of the organism.

Another aspect of the invention provides an array of oligonucleotide probes immobilized on a solid support, the array comprising:

a first probe set comprising a pluality of probes, each probe comprising a segment of nucleotides exactly complementary to a subsequence of a reference sequence, the segment including at least one interrogation position complementary to a corresponding nucleotide in the reference sequence;

wherein the reference sequence is a gene from *Mycobacterium tuberculosis*.

Another aspect of the invention provides a method of identifying the presence of a nucleic acid polymorphism in a patient sample, comprising the steps of:

(a) determining the difference between the hybridization intensities of a nucleic acid sequence from the patient sample and a corresponding nuclec acid sequence from a wild type sample to an array of reference nucleic acid probes;

(b) deriving ratios of the difference in (a) to the hybridization intensity of the wild type sample for each base position corresponding to each reference nucleic acid probe; and (c) identifying the presence of a polymorphism at a base position corresponding to a reference probe if the ratio in (b) for the base position corresponding to the reference probe is greater than or equal to an assigned value.

Another aspect of the invention provides a computer program product that identifies the presence of a nucleic acid polymorphism in a patient sample, comprising:

computer code that determines the difference between the hybridization intensities of a nucleic acid sequence from the patient sample and a corresponding nucleic acid sequence from a wild type sample to an array of reference nucleic acid probes;

computer codes that derives ratios of the difference to the hybridization intensity of the wild type sample for each base position corresponding to each reference nucleic acid probe;

computer code that identifies the presence of a polymorphism at a base position corresponding to a reference probe if the ratio for the base position coresponding to the reference probe is greater than or equal to an assigned value; and a computer readable medium that stores the computer codes.

Another aspect of the invention provides, in a computer system, a method of assigning an organism to a group, comprising the steps of:

inputting groups of a plurality of known nucleic acid sequences, the plurality of known nucleic acid sequences being from known organisms;

inputting hybridization patterns for the plurality of known nucleic acid sequences, each hybridization pattern indicating hybridization of subsequences of the known nucleic acid sequence to a subsequences of a reference nucleic acid sequence;

inputting a hybridization pattern for a sample nucleic acid sequence from the organism indicating hybridization of subsequences of the sample nucleic acid sequence to subsequences of the reference nucleic acid sequence;

comparing the hybridization pattern for the sample nucleic acid sequence to the hybridization patterns for the plurality of known nucleic acid sequences; and assigning a particular group to which the organism belongs according to the group of at least one of the known nucleic acid sequences that has a hybridization pattern that most closely matches the hybridization pattern of the sample nucleic acid sequence at specific locations.

Another aspect of the invention provides a computer program product that assigns an organism to a group, comprising:

computer code that receives as input groups of a plurality of known nucleic acid sequences, the plurality of known nucleic acid sequences being from known organisms;

computer code that receives as input hybridization patterns for the plurality of known nucleic acid sequences, each hybridization pattern indicating hybridization of subsequences of the known nucleic acid sequence of subsequences of a reference nucleic acid sequence;

computer code that receives as input a hybridization pattern for a sample nucleic aicd sequence from the organism indicating hybridization of subsequences of the sample nucleic acid sequence to subsequences of the reference nucleic acid sequence;

computer code that compares the hybridization pattern for the sample nucleic acid sequence to the hybridization patterns for the plurality of known nucleic acid sequences;

computer code that assigns a particular group to which the organism belongs according to the groups of at least one of the known nucleic acid sequences that has a hybridization pattern that most closely matches the hybridization pattern of the sample nucleic acid sequence at specific locations; and a computer readable medium that stores the computer codes.

Another aspect of the invention provides, in a computer system, a method of assigning groups to which organisms belong utilizing a generic probe array, comprising the steps of:

inputting hybridization intensities for a plurality of isolates, the hybridization intensities indicating hybridization affinity between the isolate and the generic probe array;

selecting hybridization intensities that have the most variance across the plurality of isolate; and assigning each of the plurality of isolates to a group according to the selected hybridization intensities.

Another aspect of the invention provides a computer program product that assigns groups to which organisms belong utilizing a generic probe array, comprising the steps of:

computer code that receives as input hybridization intensities for a plurality of isolates, the hybridization intensities indicating hybridization affinity between the isolate and the generic probe array;

computer code that selects hybridization intensities that have the most variance across the plurality of isolates;

computer code that assigns a group to each of the plurality of isolates according to the selected hybridization intensities; and a computer readable medium that stores the computer codes.

BRIEF DESCRIPTION OF THE DRAWINGS

FIG. 4: Exemplary arrangement of lanes on a chip. The chip shows four probe sets, each having five probes and each having a total of five interrogation positions (I1-I5), one per probe.

FIG. 5: Strategies for detecting deletion and insertion mutations. Bases in brackets may or may not be present.

FIG. 7: Shows the synthesis of a combinatorial array all possible tetranucleotide oligomers on a chip.

FIG. 9: A tiling strategy for sequence determination.

FIGS. 14A and 14B: Hybridization patterns and bar code fingerprint representations of seven *Mycobacterium* species.

FIG. 15: Bar code fingerprint representations of seven *M. gordonae* clinical isolates and the core fingerprint derived therefrom.

FIGS. 16A and 16B: Plot of hybridization intensity vs. nucleotide position using *M. gordonae* as target on an *Mycobacterium* tuberculosis rpoB chip. The bottom panel shows the sequences of the rpoB genes of *M. tuberculosis* and *M. gordonae* with the position of difference outlined in black.

FIG. 17: Plot of hybridization intensity vs. nucleotide position using other *Mycobacterium* species as target on an *Mycobacterium tuberculosis* rpoB chip.

FIG. 18: Plots of hybridization intensity vs. nucleotide position using *Mycobacterium* species as target on an *Mycobacterium tuberculosis* rpoB chip overlayed on the corresponding plot for *Mycobacterium tuberculosis*.

FIGS. 19A–19D and FIG. 20: Plots of hybridization intensity vs. nucleotide position of an unknown patient sample compared to plots of known *Mycobacterium* species as target on an *Mycobacterium tuberculosis* rpoB chip.

FIG. 21: Plots of hybridization intensity vs. nucleotide position of *Mycobacterium gordonae* isolates as target on an

*Mycobacterium tuberculosis rpoB* chip compared to a reference ATCC isolate.

FIGS. 22A and 22B: Design of a tiled array.

Figure 23:
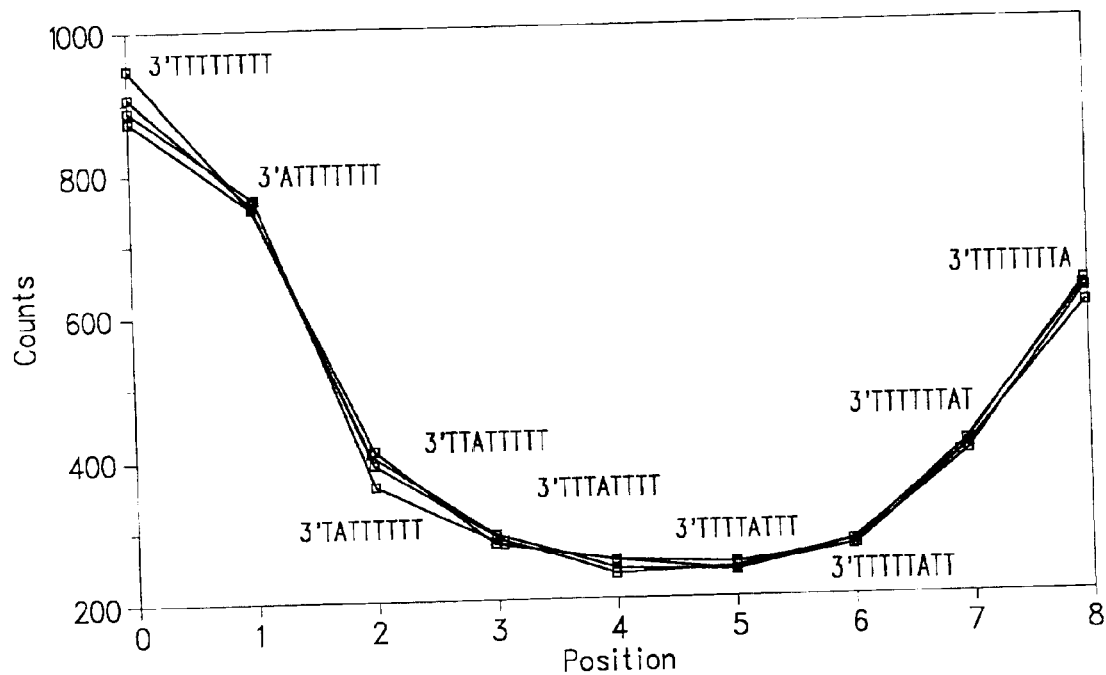

FIG. 23: Effect and positional dependence of a single base mismatch on hybrid stability using the MT1 DNA chip. The sequences of the perfect match probe and each A:A single base mismatch probe are shown. The results of five independent experiments are plotted.

Figure 24A:
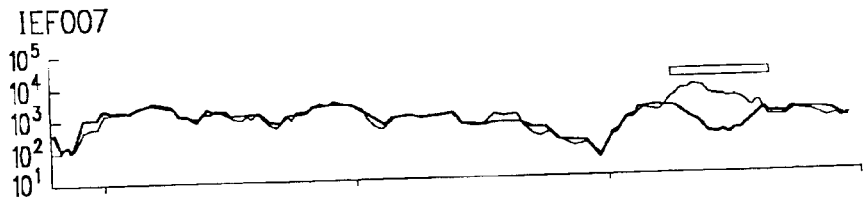
Figure 24B:
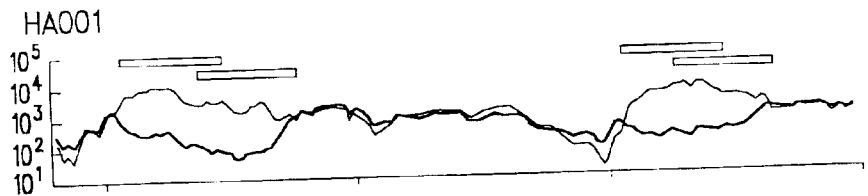
Figure 24C:
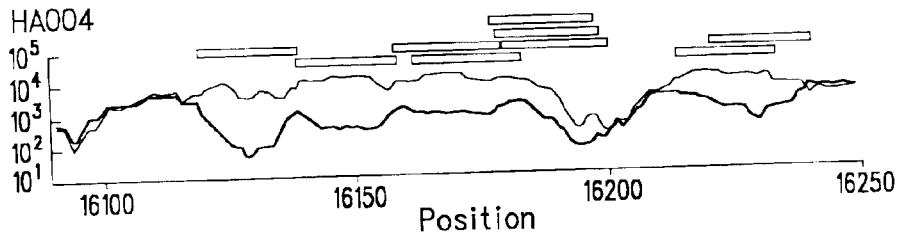

FIGS. 24A, 24B and 24C: Detection of base difference in a 2.5 kb region of human mitochondrial DNA between a sample and reference target by comparison of scaled $p^0$ hybridization intensity patterns.

Figure 25B:
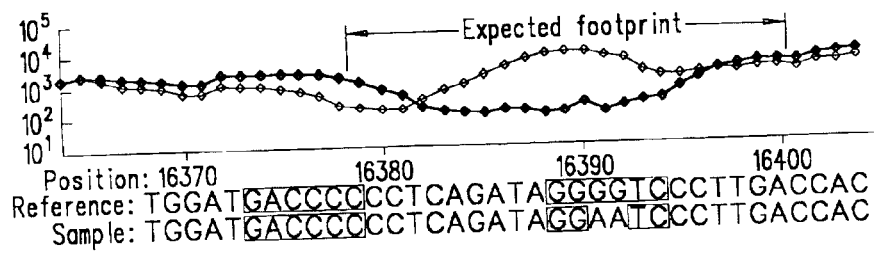
Figure 25A:
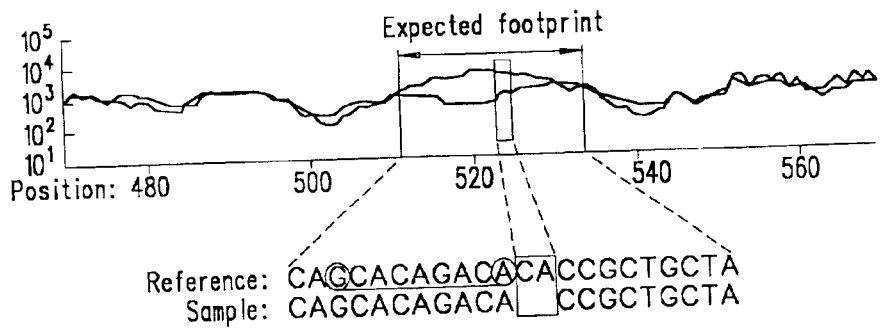

FIGS. 25A and 25B: Detection of deletion sequences of human mitochondrial DNA.

FIGS. 26A, 26B and 26C: Hybridization of 16.3 kb of a mitochondrial target to chip with the entire mitochondrial genome.

Figure 27:
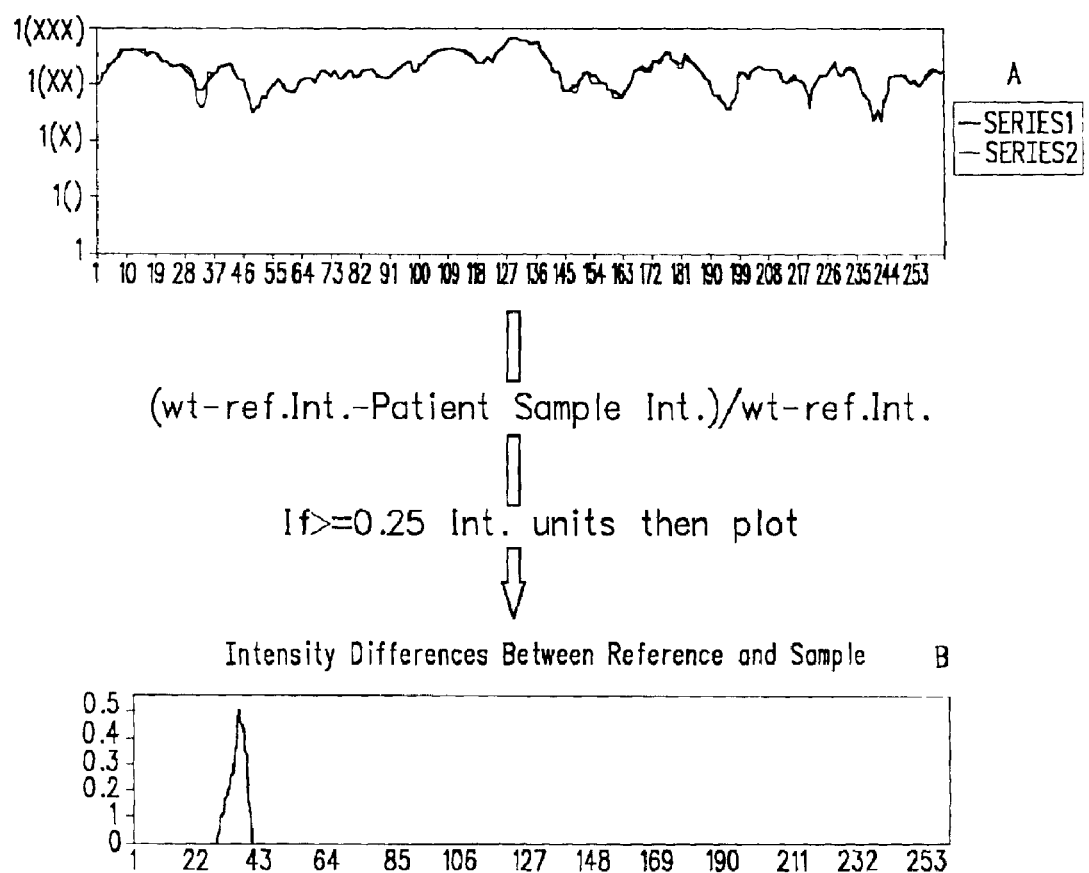

FIGS. 27A and 27B: (A) Overlay of hybridization intensities of Exon 12 of the MSH2 gene from a patient sample and from a wild type sample. (B) Plot of hybridization intensity differences greater than 0.25 between patient sample and wild type sample as a function of base position.

FIG. 28: Plot of hybridization intensity differences greater than 0.25 between patient sample and wild type sample as a function of base position for Exon 13 and Exon 16 of the MLH1 gene.

FIG. 29: Plot of hybridization intensity differences greater than 0.25 between patient sample and wild type sample as a function of base position for Exon 12 of the MSH2 gene.

Figure 30:
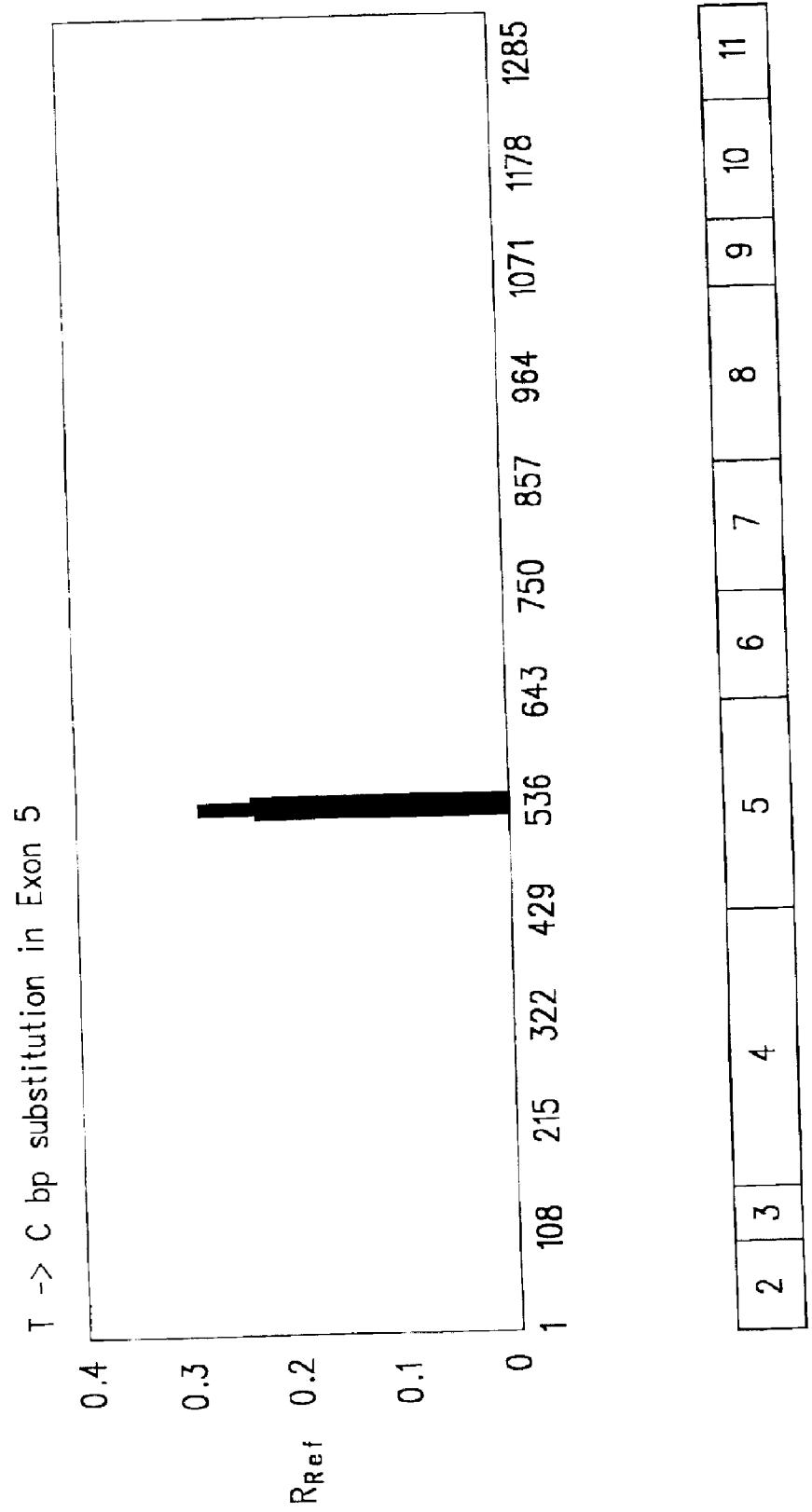

FIG. 30: Plot of hybridization intensity differences greater than 0.25 between patient sample and wild type sample as a function of base position for Exon 5 of the p53 gene.

Figure 31:
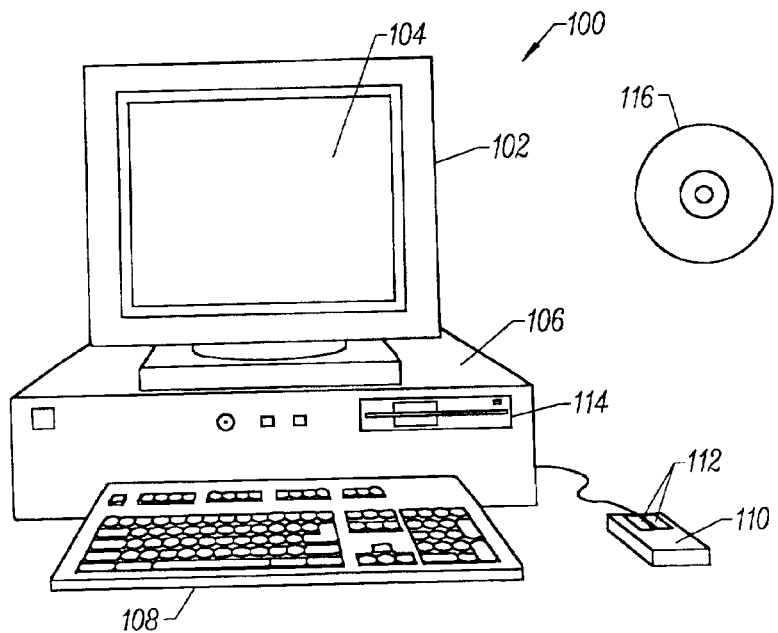

FIG. 31: Computer that may be utilized to execute software embodiments of the present invention.

Figure 32:
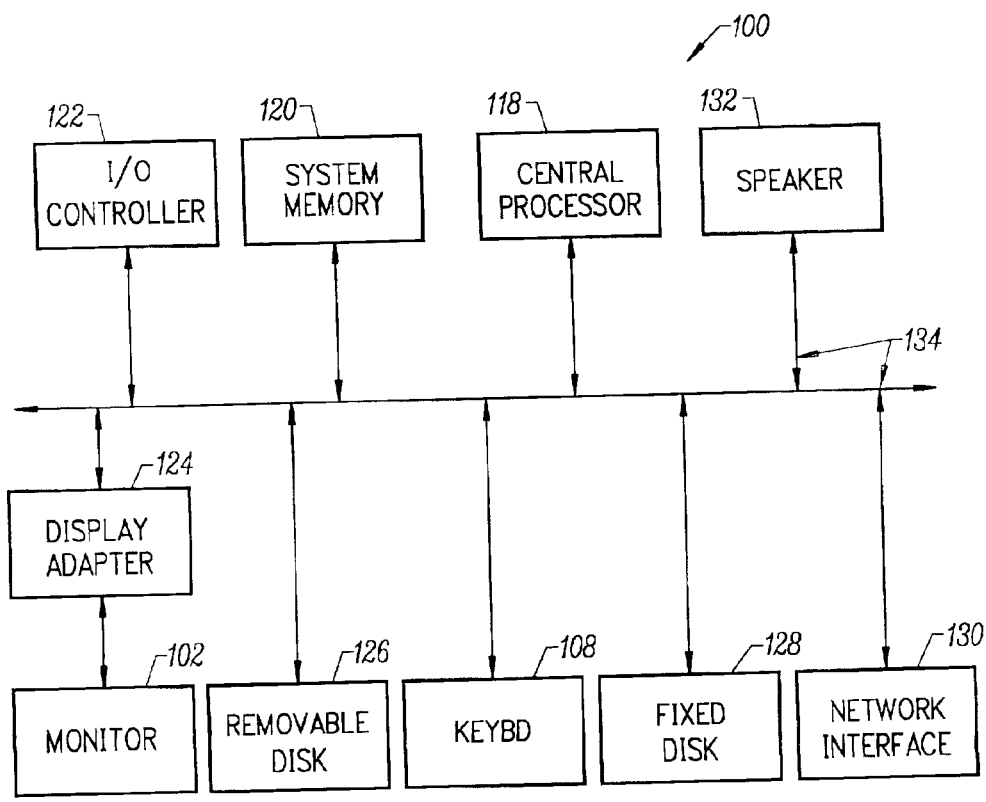

FIG. 32: A system block diagram of a typical computer system that may be used to execute software embodiments of the invention.

Figure 33:
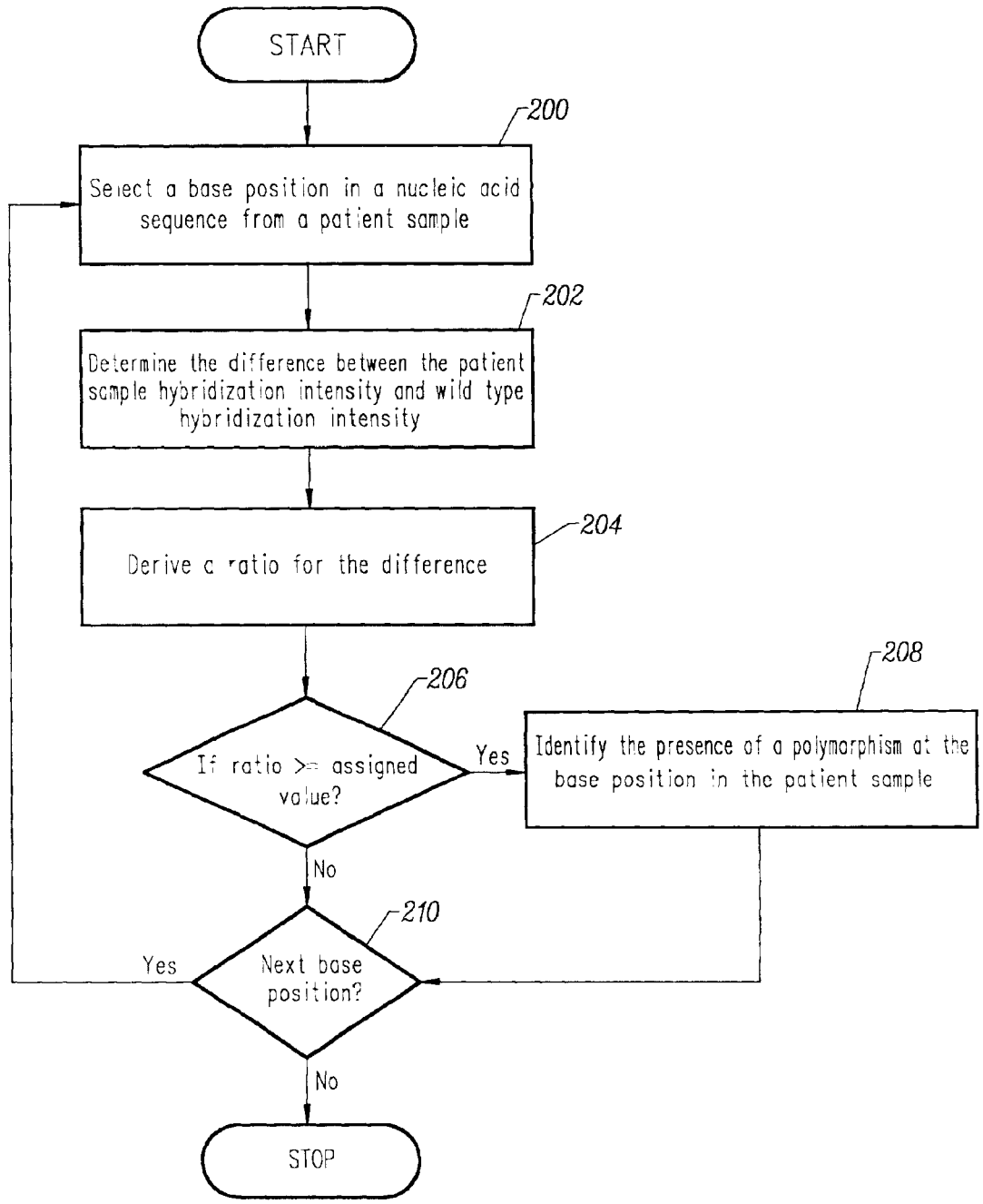

FIG. 33: A high level flowchart of identifying the presence of a polymorphism in a nucleic acid sequence from a patient sample.

Figure 34:
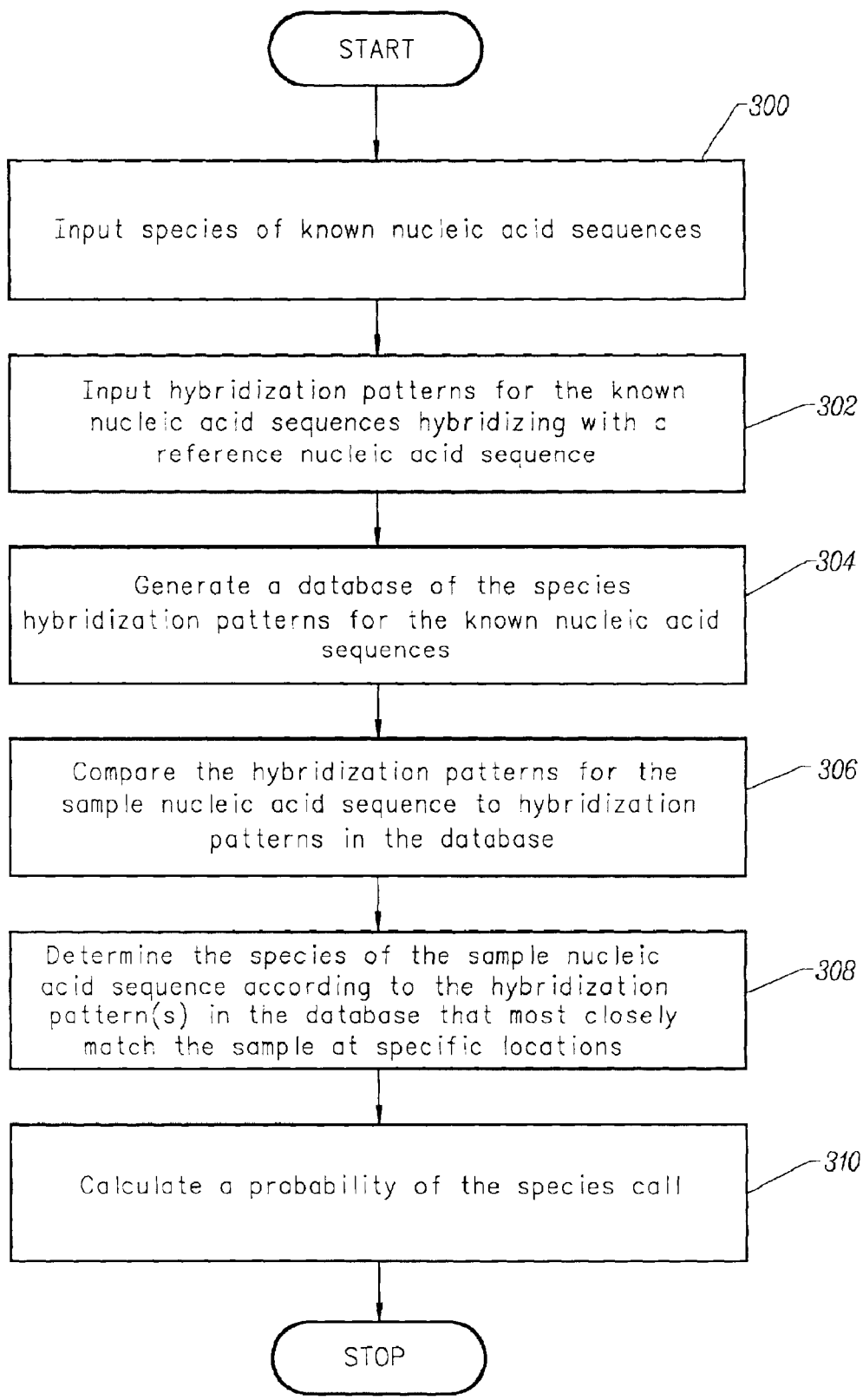

FIG. 34: A high level flowchart of a method of identifying a species within a genus to which an organism belongs.

Figure 35:
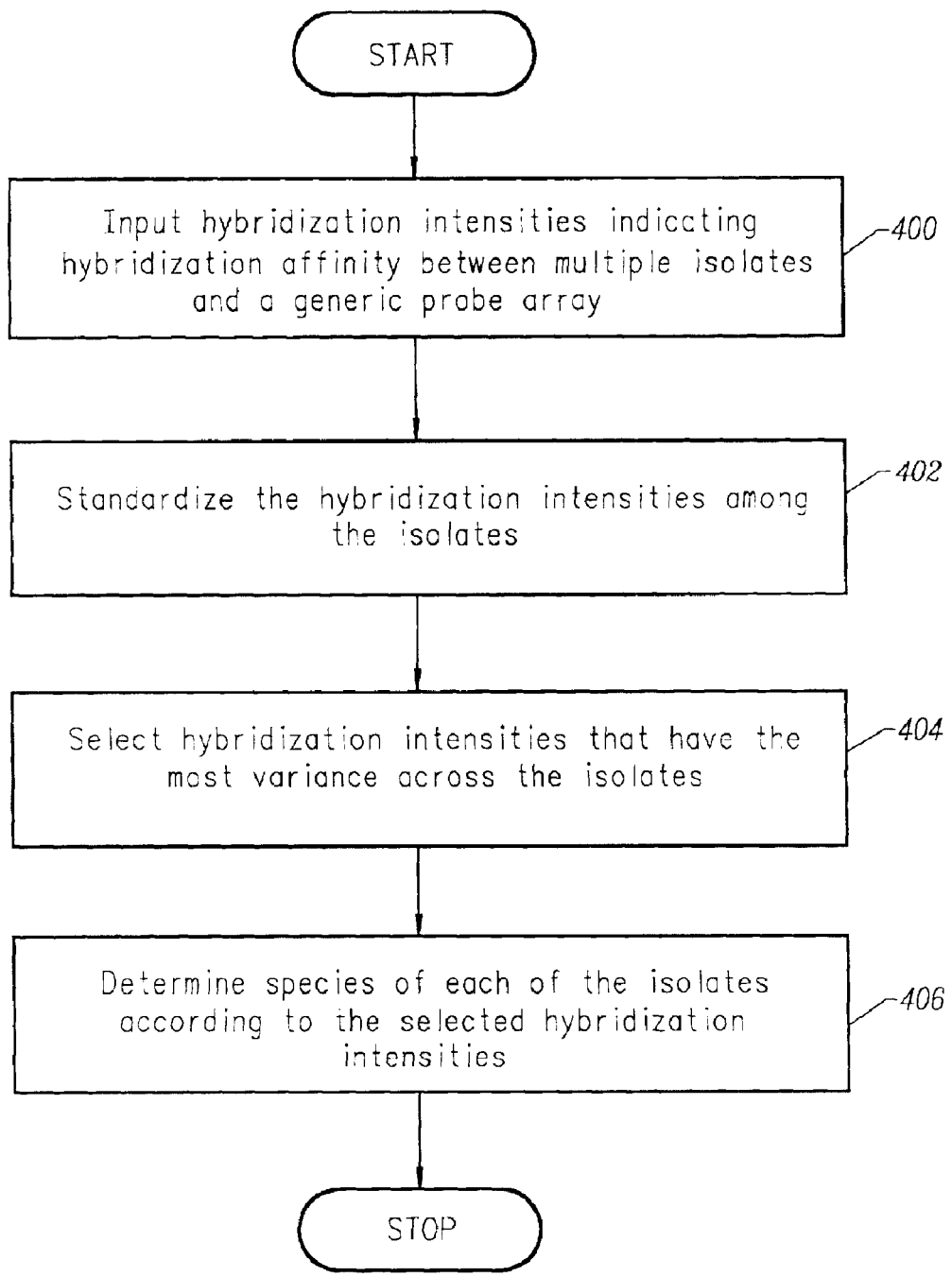

FIG. 35: A high level flowchart of a method of identifying species within a genus to which organisms belong.

Figure 36:
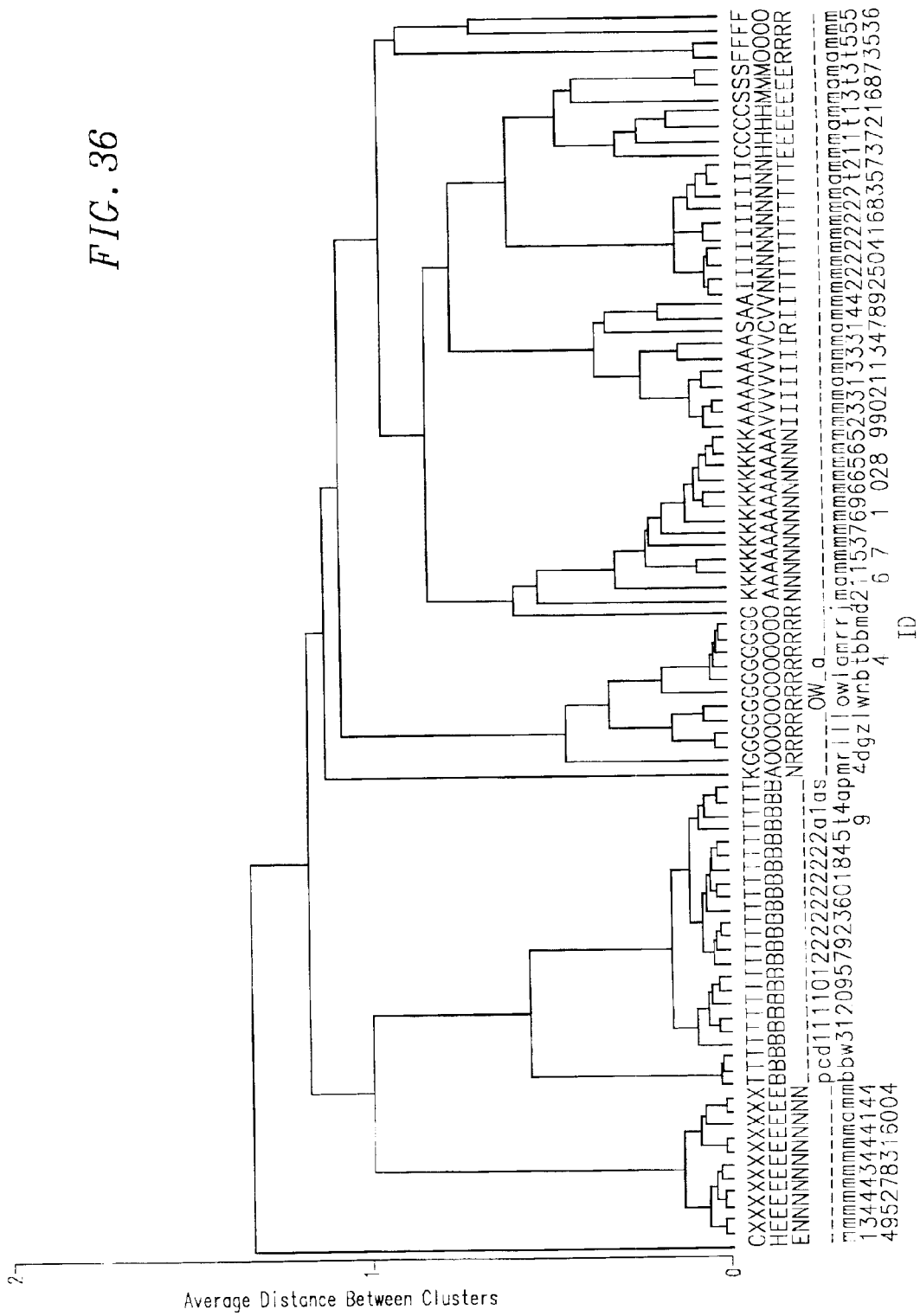

FIG. 36: A hierarchical clustering of isolates of *Mycobacterium*.

DESCRIPTION OF THE PREFERRED EMBODIMENT

This invention provides methods, compositions and devices for identifying the group or species of an organism and obtaining functional phenotypic information about the organism based on genotypic analysis of one or more genomic regions of the organism. In one embodiment, the method compares a target nucleic acid sequence from the organism coding for a gene (or its complement) to a reference sequence coding for the same gene (or its complement).

In principle, a reference sequence from any genomic region of the organism can be used. When phentotypes are being identified, it will be understood by one of skill in the art that mutations within that region will affect the phenotypic trait which is being characterized. Genotyping by contrast, only requires that a polymorphism, which may or may not code for a mutation, be present. The reference sequence can be from a highly polymorphic region, a region of intermediate polymorphic complexity or in some cases, a highly conserved region. Highly polymorphic regions are typically more informative when doing speciation analysis. The method disclosed herein is readily applicable to using reference sequences from highly polymorphic regions, though in certain cases one may prefer to use a reference sequence from a highly conserved region within the organism, since this reduces the mathematical complexity of the deconvolution required of the overall hybridization patterns observed during the analysis. In this context, a "highly conserved region" of a organism refers to a degree of conservation at the genotypic level of greater than 50%, preferably greater than 75%, and more preferably greater than 90%. A particularly useful reference sequence is the 700 bp rpoB gene from *Mycobacterium tuberculosis* (Mt), since it is well defined. Other useful reference sequences include 16SrRNA, rpoB gene, katG gene, inhA gene, gyrA gene, 23SnRNA gene, rrs gene, pncA gene, and rpsL gene. Furthermore, an 81 bp segment within this gene contains all the known mutations which code for rifampacin resistance in *M tuberculosis*. The invention is particularly useful for phenotypic and genotypic characterization of microorganisms. In this context, the term "microorganism" refers to bacteria, fungi, protozoa or viruses.

The invention finds particular utility in assaying biological samples. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Frequently, it is desirable to amplify the nucleic acid sample prior to hybridization. Suitable amplification methods include, but are not limited to polymerase chain reaction (PCR) (Innis, et al., PCR Protocols. A guide to Methods and Application. Academic Press, Inc. San Diego, (1990)), ligase chain reaction (LCR) (see Wu and Wallace, Genomics, 4:560 (1989), Landegren, et al., Science, 241:1077 (1988) and Barringer, et al., Gene, 89:117 (1990), transcription amplification (Kwoh, et al., Proc. Natl. Acad. Sci. USA, 86:1173 (1989)), and self-sustanined sequence replication (Guatelli, et al., Proc. Nat. Acad. Sci. USA, 87: 1874 (1990)).

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and coloimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

An oligonucleotide probe array complementary to the reference sequence or subsequence thereof is immobilized on a solid support using one of the display strategies described below. For the purposes of clarity, much of the following description of the invention will use probe arrays derived from the *Mycobacterium rpoB* gene as an example; however it should be recognized, as described previously, that probe arrays derived from other genes may also be used, depending on the phenotypic trait being monitored, the availability of suitable primers and the like.

Initially, target nucleic acids derived from *Mycobacterium* species having rpoB genes of known sequence and known drug resistance mutations are screened against a solid phase probe array derived from sequences complementary to the *Mycobacterium tuberculosis rpoB* gene (the Mtb rpoB chip). The known sequences are either available from the literature or can be independently established by another method, such as dideoxynucleotide sequencing. The overall hybridization pattern observed with each these speciis is compared to the overall hybridization pattern observed with *Mycobacterium tuberculosis* and differences between the two hybridization patterns are derived. A sample derived from the *Mycobacterium tuberculosis* (Mt) used as the reference sequence, being exactly complementary to the probe set(s) on the solid support, will bind to all the probes. Samples derived from other organisms, which contain one or more polymorphisms at the genotypic level, will not display similar binding. The observed patterns will vary as a function of the variation in the sequences of the rpoB genes of the individual species. Subsequences identical to Mt will generate hybridization subpatterns identical to the subpattern observed with Mt for that corresponding subsequence. Subsequences which differ from Mt will generate hybridization subpatterns which differ from the Mt subpattern for that corresponding subsequence. Thus, the overall hybridization pattern observed with a particular species allows one to identify regions of the ropB gene of the species which differ from that of Mt.

The presence of a different hybridization pattern in a specified region of the substrate can be correlated with a probability that the target nucleic acid is from a specific species. In the idealized case, the differential hybridization pattern in a single region will allow species identification. This can occur when one or more polymorphisms in that region are uniquely associated with a specific species. More frequently however, such an unique one-to-one correspondence is not present. Instead, differential hybridization patterns (i.e., relative to the reference sequence) are observed in multiple regions, none of which will bear an unique correspondence to a particular species. However, each differential hybridization patterns will be associated with a probability of the organism being screened belonging to a particular species (or not) or carrying a particular phenotypic trait (or not). As a result, detection of an increasing number of these sets of differences allows one to classify the organism with an increasing level of confidence. Other algorithms can be used to derive such composite probabilities from the detection of multiple sets of differences. Therefore, the overall hybridization pattern, which is the aggregrate of all the differential hybridizations observed at all regions of the substrate, allows one to assign with high confidence, the speciation and/or phenotype of the organism.

When a single probe set is being used on the substrate, it will usually not be able to define the differences in sequence between the target and the reference sequence, absent additional knowledge about the target. Multiple probe sets can be used, as with the tiling strategies disclosed herein and described in more detail in PCT publication WO95/11995. In some cases, the differences will be definable, i.e., the different nucleotide responsible for the different hybridization pattern will be known. In other cases the differences will not be definable, i.e., all one will know is that a polymorphism is present in that region. However, this is primarily a function of the probe array used on the chip. If necessary the sample can be screened against a different probe array to assign the polymorphism present in that region. Since the point mutations which confer antibiotic resistance, for example to rifampacin, for Mt are frequently known, the presence of a change in the hybridization pattern in the region where the point mutation occurs signals the presence of a rifampacin resistant species. It will be apparent that this technique is not limited to identifying drug resistance. Any phenotypic trait whose variation has been mapped to mutations is a particular genomic region can be identified by this method. Representative and nonlimiting examples include the presence of toxin and pathogenic markers.

It is important to recognize that this method provides more than the ability to identify genotypic variations and thus phenotype by hybridization. Analysis of hybridization patterns of a single genomic region of a microorganism with the Mt rpoB chip also provides, as explained below, a method of identifying the species of the microorganism.

This chip based screening method allows one to build up a data base of hybridization patterns corresponding to different species. Some regions of the hybridization pattern will be shared among subsets of the species because their sequences in regions corresponding to those hybridizations are identical. Other regions of the hybridization pattern will differ between two species because the sequence corresponding to those hybridizations are different. In all cases, the sequences of the rpoB gene of the unknown species are being compared to the corresponding sequence of Mt. Differences in the hybridization pattern of a particular species to the pattern observed with Mt as sample, can be correlated to the presence of a polymorphism at a particular point in the sequence of that species. Some polymorphisms will be definable, i.e., one will know not only that the nucleotide at that position differs from that of Mt, but one will also know the identity of that nucleotide. Some polymorphisms will be unique to the particular species, i.e., species-specific; they will be present in that particular species and not in any other species. Other polymorphisms will be shared, i.e., they will not be unique to a particular species. Certain subsets of species will have the polymorphism and others will not. However, each of these polymorphisms can be assigned to its particular subset of species. Therefore, the presence of a shared polymorphism, despite not indicating with certainty that the sample being screened contains a particular species, increases the probability that one species of that particular subset of species is present.

The hybridization pattern of a particular sample can be represented as a "bar code" in which the individual lines of the bar code indicate the presence of a polymorphism reltaive to Mt. This invention provides a method of screening large numbers of individual species and thus deriving information on the polymorphisms present in those species. Each individual line can be assigned a probability of being associated with different species. In this fashion, a data base can be bulit up in which increasing numbers of polymorphisms can be associated with the different species. As one will recognize, the presence of an unique species-specific polymorphism will allow the immediate identification of a sample as being a particular species. However, even the presence of shared polymorphisms among several species will allow species identification. In the simplest case, each species can be assigned a "fingerprint" of shared polymorphisms, i.e., that species and isolates of that species will possess a particular collection of shared polymorphisms. However, it is not necessary for one to be able to assign an unique "fingerprint" pattern of shared polymorphisms to a species in order to be able to identify that species. As long as one can correlate the presence of a particular polymorphism or subset of polymorphisms with a probability of the sample being a particular species, the detection of increasing numbers of such polymorphisms allows one to predict with increasing probability the speciation of the sample, i.e, as one observes more and more such polymorphisms associated with a particular species, the confidence level of the sample being that particular speices increases. Standard mathematical algorithms can be used to make this prediction. Therefore, once the data base is sufficiently larger, the lack of an "unique" fingerprint for a species becomes irrelevant. Typically, the mathematical algorithm will make a call of the identity of the species and assign a confidence level to that call. One can determine the confidence level (>90%, >95% etc.) that one desires and the algorithm will analyze the hybridization pattern and either provide an identification or not. Occasionally, the call may be that the sample may be one of two, three or more species, in which case a specific identification will not be possible. However, one of the strengths of this technique is that the rapid screening made possible by the chip-based hybridization allows one to continuously expand the data base of patterns and polymorphisms to ultimately enable the identification of species previously unidentifiable due to lack of sufficient information.

Analysis of an increasing number of isolates of a known species will allow one to build up a fingerprint that is characteristic of that species. However, it is important to note that as the total number of analyzed isolates for each species is increased, it is unlikely that a single and unique core fingerprint will define a *Mycobacterium* species. Rather, it is expected that any particular isolate of a *Mycobacterium* species will have a subset of all possible fingerprints. Identification of the *Mycobacterium* species based on a fingerprint pattern will require a classification analysis, such as by using a tree-based classification algorithm as described below, built upon a collected database consisting of species specific and shared single nucleotide polymorphisms (SNPs) and fingerprints. Thus, the chip-based method of determining hybridization patterns disclosed herein allows one to both build up a data base of polymorphisms associated with a particular species and use that data base to identify the specation and phenotypic characteristic of an unknown sample from a single hybridization experiment.

It should also be recognized that since this technique rests on differences in hybridization patterns, this method of speciation does not rest on knowing the actual identity of the polymorphism. The hybridization pattern relative to Mt will differ as long as a nucleotide at a particular point in the sequence differs from that of Mt. The exact nature of the substitution, insertion or deletion, e.g., A to T, C or G is less important than the fact that the nucleotide is not A (assuming for the purposes of illustration that Mt carries an A at that position). It is not necessary that the sample be sequenced in order to idenify its speciation.

A second layer of confidence can be added to the initial determination by analyzing whether the differences in hybridization patterns are shared or unique. If the species identified is supposed to have either a shared or unique polymorphism at a particular site and the chi has in face detected such a polymorphism, then one can be more confident in the initial determination.

Both identification and phenotyping can be accomplished based on genotypic determinations of a single region of the mycobacteria genome in place of analysis of two genomic regions (the rpoB and the 16S rRNA genes). Two generic implications can derived from the successful demonstration of the use of high density oligonucleotide arrays for mycobacteria identification and antibiotic drug sensitivity. First, other genes affecting drug sensitivity can be encoded on the high density oligonucleotide arrays (see Table 1) and hybridization patterns for each of these additional genes can be used to confirm and provide confidence measurements for fingerprints derived from the rpoB gene. Second, the same chip-based strategy could be employed for other eubacteria species which simultaneously could provide genotypic information concerning important clinical phenotypes (e.g., toxin and pathogen marker genes) as well as identification information.

The preceding discussion has used the Mt rpoB gene as an example. It should be recognized that this method is generally appicable to other microorganisms and reference sequences derived from other genomic regions, such as, for example, the human mitochondrial DNA sequence and the MT DNA sequence. The length of a reference sequence can vary widely from a full-length genome, to an individual chromosome, episome, gene, component of a gene, such as an exon or regulatory sequences, to a few nucleotides. A reference sequence of between about 2, 5, 10, 20, 50, 100, 5000, 1000, 5,000 or 10,000, 20,000 or 100,000 nucleotides is common. Sometimes only particular regions of a sequence are of interest. In such situations, the particular regions can be considered as separate reference sequences or can be considered as components of a singlereference sequence, i.e., the microbial genome.

A reference sequence can be any naturally occurring, mutant, consensus sequence of nucleotides, RNA or DNA. For example, sequences can be obtained from computer data bases, publications or can be determined or conceived de novo. Usually, a reference sequence is selected to show a high degrss of sequence identity to envisaged target sequences. Often, particularly, where a significant degree of divergence is anticipated between target sequences, more than one reference sequence is selected. Combinations of wild-type and mutant reference sequences are employed in several applications of the tiling strategy.

FIG. 31 illustrates an example of a computer system that may be used to execute software embodiments of the present invention. FIG. 31 shows a computer system 100 which includes a monitor 102, screen 104, cabinet 106, keyboard 108, and mouse 110. Mouse 110 may have one or more buttons such as mouse buttons 112. Cabinet 106 houses a CD-ROM drive 114, a system memory and a hard drive (see FIG. 32) which may be utilized to store and retrieve software programs incorporating code that implements the present invention, data for use with the present invention, and the like. Although a CD-ROM 116 is shown as an exemplary computer readable storage medium, other computer readable storage media including floppy disks, tape, flash memory, system memory, and hard drives may be utilized. Cabinet 106 also houses familiar computer components such as a central processor, system memory, hard disk, and the like.

FIG. 32 shows a system block diagram of computer system 100 that may be used to execute software embodiments of the present invention. As in FIG. 31, computer system 100 includes monitor 102 and keyboard 108. Computer system 100 further includes subsystems such as a central processor 102, system memory 120. I/O controller 122, display adapter 124, removable disk 126 (e.g., CD-ROM drive), fixed disk 128 (e.g., hard drive), network interface 130, and speaker 132. Other computer systems suitable for use with the present invention may include additional or fewer subsystems. For example, another computer system could include more than one processor 102 (i.e., a multi-processor system) or a cache memory.

Arrows such as 134 represent the system bus architecture of computer system 100. However, these arrows are illustrative of any interconnection scheme serving to link the subsystems. For example, a local bus could be utilized to connect the central processor to the system memory and display adapter. Computer system 100 shown in FIG. 32 is but an example of a computer system suitable for use with the present invention. Other configurations of subsystems suitable for use with the present invention will be readily apparent to one or ordinary skill in the art.

The methods of this invention employ oligonucleotide arrays which comprise probes exhibiting complementarity to one or more selected refernce sequences whose sequence is known. Typically, these arrays are immobilized in a high density array ("DNA on chip") on a solid surface as described in U.S. Pat. No. 5,143,854 and PCT patent publication Nos. WO 90/15070, WO 92/10092 and WO 95/11995, each of which is incorporated herein by reference.

Various strategies are available to order and display the oligonucleotide probe arrays on the chip and thereby maximize the hybridization pattern and sequence information derivable regarding the target nucleic acid. Exemplary display and ordering strategies are described in PCT patent publication No. WO 94/12305, incorporated herein by reference. For the purposes of fuller description, a brief description of the basic strategy is described below.

The basic tiling strategy provides an array of immobilized probes for analysis of target sequences showing a high degree of sequence identity to one or more selected reference sequences. The strategy is illustrated for an array that is subdivided into four probe sets, although it will be apparent that satisfactory results are obtained from one probe set (i.e., a probe set complementary to the reference sequence as described earlier).

A first probe set comprises a plurality of probes exhibiting perfect complementarity with a selected reference sequence. The perfect complementarity usually exists throughout the length of the probe. However, probes having a segment or segments of perfect complementarity that is/are flanked by leading or trailing sequences lacking complementarity to the reference sequence can also be used. Within a segment of complementarity, each probe in the first probe set has at least one interrogation position that corresponds to a nucleotide in the reference sequence. That is, the interrogation position is aligned with the corresponding nucleotide in the reference sequence, when the probe and reference sequence are aligned to maximize complementarity between the two. If a probe has more than one interrogation position, each corresponds with a respective nucleotide in the reference sequence. The identity of an interrogation position and corresponding nucleotide in a particular probe in the first probe set cannot be determined simply by inspection of the probe in the first set. As will become apparent, an interrogation position and corresponding nucleotide is defined by the comparative structures of probes in the first probe set and corresponding probes from additional probe sets.

In principle, a probe could have an interrogation position at each position in the segment complementary to the reference sequence. Sometimes, interrogation positions provide more accurate data when located away from the ends of a segment of complementarity. Thus, typically a probe having a segment of complementarity of length x does not contain more than x-2 interrogation positions. Since probes are typically 9–21 nucleotides, and usually all of a probe is complementary, a probe typically has 1–19 interrogation positions. Often the probes contain a single interrogation position, at or near the center of probe.

Figure 1:
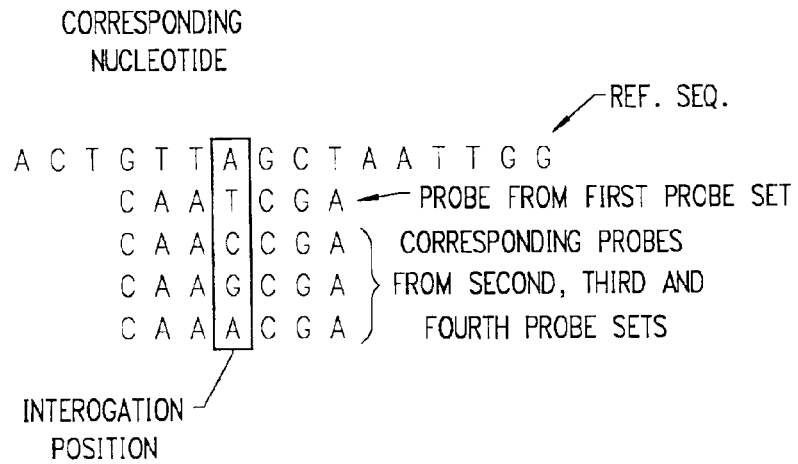
FIG 1: Basic tiling strategy. The figure illustrates the relationship between an interrogation position (I) and a corresponding nucleotide (n) in the reference sequence, and between a probe from the first probe set and corresponding probes from second, third and fourth probe sets.
Figure 2:
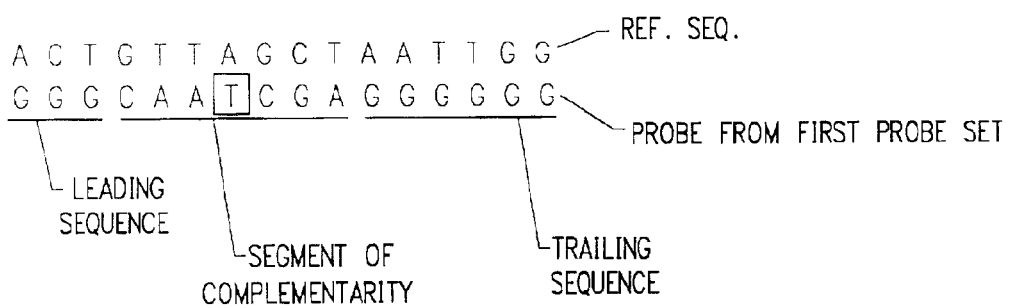
FIG 2: Segment of complementary in a probe from the first probe set.

For each probe in the first set, there are, for purposes of the present illustration, up to three corresponding probes from three additional probe sets. FIG. 1 illustrates the basic "tiling" strategy of the invention. Thus, there are four probes corresponding to each nucleotide of interest in the reference sequence. Each of the four corresponding probes has an interrogation position aligned with that nucleotide of interest. Usually, the probes from the three additional probe sets are identical to the corresponding probe from the first probe set with one exception. The exception is that at least one (and often only one) interrogation position, which occurs in the same position in each of the four corresponding probes from the four probe sets, is occupied by a different nucleotide in the four probe sets. For example, for an A nucleotide in the reference sequence, the corresponding probe from the first probe set has its interrogation position occupied by a T, and the corresponding probes from the additional three probe sets have their respective interrogation positions occupied by A, C, or G, a different nucleotide in each probe. Of course, if a probe from the first probe set comprises trailing or flanking sequences lacking complementarity to the reference sequences (see FIG. 2), these sequences need not be present in corresponding probes from the three additional sets. Likewise corresponding probes from the three additional sets can contain leading or trailing sequences outside the segment of complementarity that are not present in the corresponding probe from the first probe set. Occasionally, the probes from the additional three probe set are identical (with the exception of interrogation position(s)) to a contiguous subsequence of the full complementary segement of the corresponding probe from the first probe set. In this case, the subsequence includes the interrogation position and usually differs from the full-length probe only in the omission of one or both terminal nucleotides from the termini of a segment of complementarity. That is, if a probe from the first probe set has a segment of complementarity of length n, corresponding probes from the other sets will usually include a subsequence of the segment of at least length n-2. Thus, the subsequence is usually at least 3, 4, 7, 9, 15, 21, or 25 nucleotides long, most typically, in the range of 9–21 nucleotides. The subsequence should be sufficiently long or hybridization conditions such to allow a probe to hybridize detectably more strongly to a variant of the reference sequence mutated at the interrogation position than to the reference sequence.

The probes can be oligodeoxyribonucleotides or oligoribonucleotides, or any modified forms of these polymers that are capable of hybridizing with a target nucleic sequence by complementary base-pairing. Complementary base pairing means sequence-specific base pairing which includes e.g., Watson-Crick base pairing as well as other forms of base pairing such as Hoogsteen base pairing. Modified forms include 2'-O-methyl oligoribonucleotides and so-called PNAs, in which oligodeoxyribonucleotides are linked via peptide bonds rather than phophodiester bonds. The probes can be attached by any linkabe to a support (e.g., 3', 5' or via the base). 3' attachment is more usual as this orientation is compatible with the preferred chemistry for solid phase synthesis of oligonucleotides.

The number of probes in the first probe set (and as a consequence the number of probes in additional probe sets) depends on the length of the reference sequence, the number of nucleotides of interest in the reference sequence and the number of interrogation positions per probe. In general, each nucleotide of interest in the reference sequence requires the same interrogation position in the four sets of probes. Consider, as an example, a reference sequence of 100 nucleotides, 50 of which are of interest, and probes each having a single interrogation position. In this situation, the first probe set requires fifty probes, each having one interrogation position corresponding to a nucleotide of interest in the reference sequence. The second, third and fourth probe sets each have a corresponding probe for each probe in the first probe set, and so each also contains a total of fifty probes. The identity of each nucleotide of interest in the reference sequence is determined by comparing the relative hybridization signals at four probes having interrogation positions corresponding to that nucleotide from the four probe sets.

Figure 3:
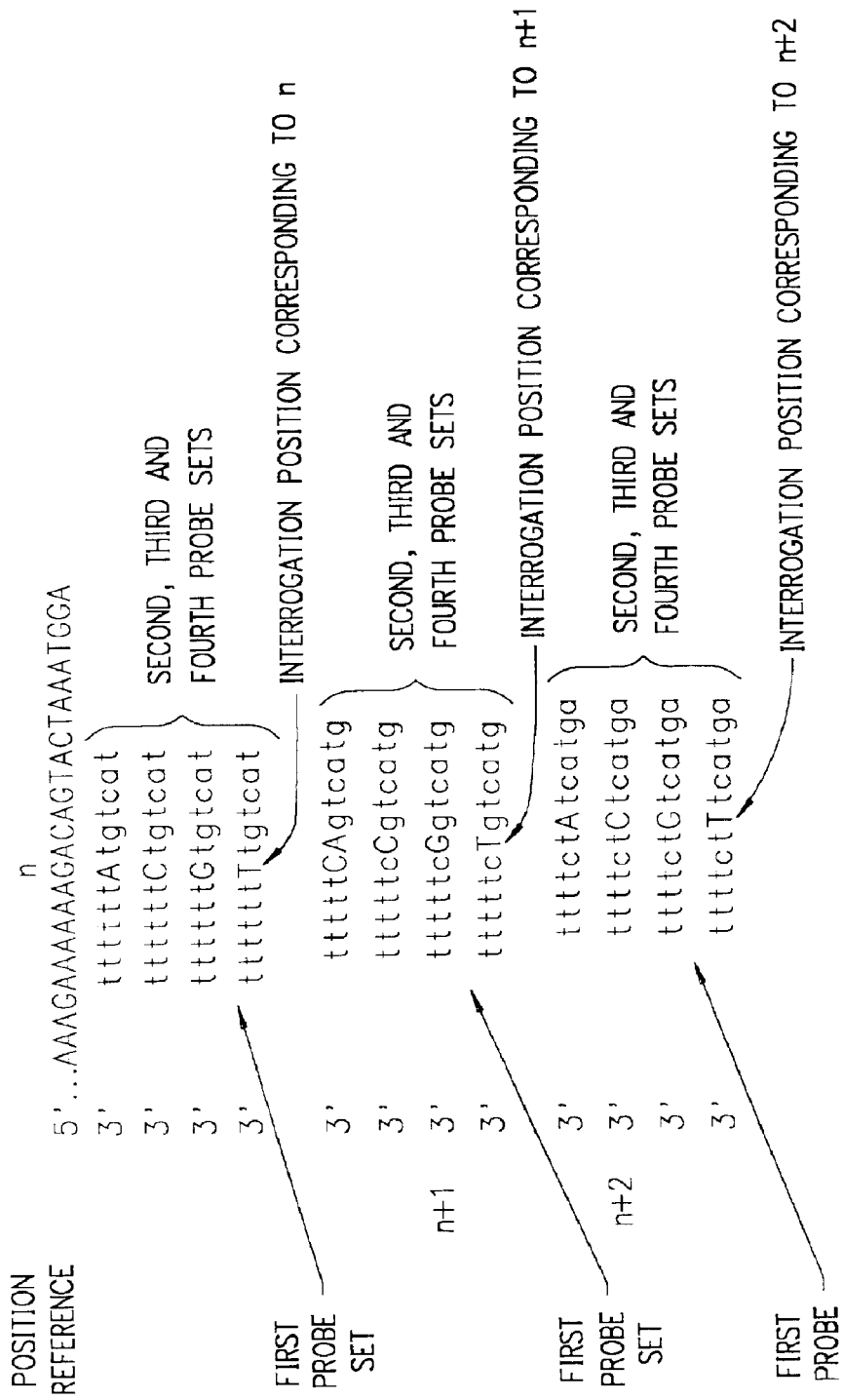
FIG 3: Incremental succession of probes in a basic tiling strategy. The figure shows four probe sets, each having three probes. Note that each probe differs from its predecessor in the same set by the acquisition of a 5' nucleotide and the loss of a 3' nucleotide, as well as in the nucleotide occupying the interrogation position.

In some reference sequences, every nucleotide is of interest. In other reference sequences, only certain portions in which variants (e.g., mutations or polymorphisms) are concentrated are of interest. In other reference sequences, only particular mutations or polymorphisms and immediately adjacent nucleotides are of interest. Usually, the first probe set has interrogation positions selected to correspond to at least a nucleotide (e.g., representing a point mutation) and one immediately adjacent nucleotide. Usually, the probes in the first set have interrogation positions corresponding to at least 3, 10, 50, 100, 1000, 20,000, 100,000, 1,000,000, 10,000,000, or more contiguous nucleotides. The probes usually have interrogation positions corresponding to at least 5, 10, 30, 50, 75, 90, 99 or sometimes 100% of the nucleotides in a reference sequence. Frequently, the probes in the first probe set completely span the reference sequence and overlap with one another relative to the reference sequence. For example, in one common arrangement each probe in the first probe set differs from another probe in that set by the omission of a 3' base complementary to the reference sequence and the acquisition of a 5' base complementary to the reference sequence. FIG. 3 illustrates an incremental succession of probes in a basic tiling strategy.

The number of probes on the chip can be quite large (e.g., $10^5$–$10^6$). However, often only a relatively small proportion (i.e., less than about 50%, 25%, 10%, 5% or 1%) of the total number of probes of a given length are selected to pursue a particular tiling strategy. For example, a complete set of octomer probes comprises 65,536 probes; thus, an array of the invention typically has fewer than 32,768 octomer probes. A complete array of decamer probes comprises 1,048,576 probes; thus, an array of the invention typically has fewer than about 500,000 decamer probes. Often arrays have a lower limit of 25, 50 or 100 probes and as many probes as $10^4$, $10^5$, $10^6$, $10^7$, $10^8 10^9$, $10^{10}$, etc. probes. The arrays can have other components besides the probes such as linkers attaching the probes to a support.

Some advantages of the use of only a proportion of all possible probes of a given length include: (i) each position in the array is highly informative, whether or not hybridization occurs; (ii) nonspecific hybridization is minimized; (iii) it is straightforward to correlate hybridization differences with sequence differences, particularly with reference to the hybridization pattern of a known standard; and (iv) the ability to address each probe independently during synthesis, using high resolution photolithography, allows the array to be designed and optimized for any sequence. For example the length of any probe can be varied independently of the others.

For conceptual simplicity, the probes in a set are usually arranged in order of the sequence in a lane across the chip, although this arrangement is not required. For example, the probes can be randomly distributed on the chip. A lane contains a series of overlapping probes, which represent or tile across, the selected reference sequence (see FIG. 3). The components of the four sets of probes are usually laid down in four parallel lanes, collectively constituting a row in the horizontal direction and a series of 4-member columns in the vertical direction. Corresponding probes from the four probe sets (i.e., complementary to the same subsequence of the reference sequence) occupy a column. Each probe in a lane usually differs from its predecessor in the lane by the omission of a base at one end and the inclusion of additional base at the other end as shown in FIG. 3. However, this orderly progression of probes can be interrupted by the inclusion of control probes or omission of probes in certain columns of the array. Such columns serve as controls to orient the chip, or gauge the background, which can include target sequence nonspecifically bound to the chip.

The probes sets are usually laid down in lanes such that all probes having an interrogation position occupied by an A nucleotide form an A-lane, all probes having an interrogation position occupied by a C nucleotide form a C-lane, all probes having an interrogation position occupied by a G nucleotid form a G-lane, and all probes having an interrogation position occupied by a T (or U) form a T lane (or a U lane). Note that in this arrangement there is not a unique correspondence between probe sets and lanes. Thus, the probe from the first probe set is laid down in the A-lane, C-lane, A-lane, A-lane and T-lane for the five columns in FIG. 4. The interrogation position on a column of probes corresponds to the position in the target sequence whose identity is determined from analysis of hybridization to the probes in that column. Thus, $I_1$–$I_5$ respectively correspond to $N_1$–$N_5$ in FIG. 4. The interrogation position can be anywhere in a probe but is usually at or near the central position of the probe to maximize differential hybridization signals between a perfect match and a single-base mismatch. For example, for an 11 mer probe, the central position is the sixth nucleotide.

Although the array of probes is usually laid down in rows and columns as described above, such a physical arrangement of probes on the chip is not essential. Provided that the spatial location of each probe in an array is known, the data from the probes can be collected and processed to yield the sequence of a target irrespective of the physical arrangement of the probes on a chip. In processing the data, the hybridization signals from the respective probes can be reassorted into any conceptual array desired for subsequent data reduction whatever the physical arrangement of probes on the chip.

A range of lengths of probes can be employed in the chips. As noted above, a probe may consist exclusively of a complementary segments, or may have one or more complementary segments juxtaposed by flanking, trailing and/or intervening segments. In the latter situation, the total length of complementary segment(s) is more important that the length of the probe. In functional terms, the complementary segment(s) of the first probe sets should be sufficiently long to allow the probe to hybridize detectably more strongly to a reference sequence compared with a variant of the reference including a single base mutation at the nucleotide corresponding to the interrogation position of the probe. Similarly, the complementary segment(s) in corresponding probes from additional probe sets should be sufficiently long to allow a probe to hybridize detectably more strongly to a variant of the reference sequence having a single nucleotide substitution at the interrogation position relative to the reference sequence. A probe usually has a single complementary segment having a length of at least 3 nucleotides, and more usually at least 5, 6, 7, 8, 9, 10, 11, 12, 13, 14, 15, 16, 17, 18, 19, 20, 21, 22, 23, 24, 25 or 30 bases exhibiting perfect complementary (other than possibly at the interrogation position(s) depending on the probe set) to the reference sequence.

In some chips, all probes are the same length. Other chips employ different groups of probe sets, in which case the probes are of the same size within a group, but differ between different groups. For example, some chips have one group comprising four sets of probes as described above in which all the probes are 11 mers, together with a second group comprising four sets of probes in which all of the probes are 13 mers. Of course, additional groups of probes can be added. Thus, some chips contain, e.g., four groups of probes having sizes of 11 mers, 13 mers, 15 mers and 17 mers. Other chips have different size probes within the same group of four probes. In these chips, the probes in the first set can vary in length independently of each other. Probes in the other sets are usually the same length as the probe occupying the same column from the first set. However, occasionally different lengths of probes can be included at the same column position in the four lanes. The different length probes are included to equalize hybridization signals from probes depending on the hybridization stability of the oligonucleotide probe at the pH, temperature, and ionic conditions of the reaction.

The length of a probe can be important in distinguishing between a perfectly matched probe and probes showing a single-base mismatch with the target sequence. The discrimination is usually greater for short probes. Shorter probes are usually also less susceptible to formation of secondary structures. However, the absolute amount of target sequence bound, and hence the signal, is greater for larger probes. The probe length representing the optimum comprise between these competing considerations may vary depending on inter alia the GC content of a particular region of the target DNA sequence, secondary structure, synthesis efficiency and cross-hybridization. In some regions of the target, depending on hybridization conditions, short probes (e.g., 11 mers) may provide information that is inaccessible from longer probes (e.g., 19 mers) and vice versa. Maximum sequence information can be read by including several groups of different sized probes on the chip as noted above. However, for many regions of the target sequence, such a strategy provides redundant information in that the same sequence is read multiple times from the different groups of probes. Equivalent information can be obtained from a single group of different sized probes in which the sizes are selected to maximize readable sequence at particular regions of the target sequence.

Some chips provide an additional probe set specifically designed for analyzing deletion mutations. The additional probe set comprises a probe corresponding to each probe in the first probe set as described above. However, a probe from the additional probe set differs from the corresponding probe in the first probe set in that the nucleotide occupying the interrogation position is deleted in the probe from the additional probe set, as shown in FIG. 5. Optically, the probe from the additional probe set bears an additional nucleotide at one of its termini relative to the corresponding probe from the first probe set (shown in brackets in FIG. 5). The probe from the additional probe set will hybridize more strongly than the corresponding probe from the first probe set to a target sequence having a single base deletion at the nucleotide corresponding to the interrogation position. Additional probe sets are provided in which note only the interrogation position, but also an adjacent nucleotide is deleted.

Similarly, other chips provide additional probe sets for analyzing insertions. For example, one additinal probe set has a probe corresponding to each probe in the first probe set as described above. However, the probe in the additional probe set has an extra T nucleotide inserted adjacent to the interrogation position. See FIG. 5 (the extra T is shown in a square box). Optionally, the probe has one fewer nucleotide at one of its termini relative to the corresponding proe from the first probe set (shown in brackets). The probe from the additional probe set hybridizes more strongly than the corresponding probe from the first probe set to a target sequence having an A insertion to the left of nucleotide "n" of the reference sequence in FIG. 5. Similar additional probe sets can be constructed having C, G or A nucleotides inserted adjacent to the interrogation position.

Usually, four such additional probe sets, one for each nucleotide, are used in combination. Comparison of the hybridization signal of the probes from the additional probe sets with the corresponding probe from the first probe set indicates whether the target sequence contains and insertion. For example, if a probe from one of the additional probe sets shows a higher hybridization signal than a corresponding probe from the first probe set, it is deduced that the target sequence contains an insertion adjacent to the corresponding nucleotide (n) in the target sequence. The inserted base in the target is the complement of the inserted base in the probe from the additional probe set showing the highest hybridization signal. If the corresponding probe from the first probe set shows a higher hybridization signal than the corresponding probes from the additional probe sets, then the target sequence does not contain an insertion to the left of corresponding position (("n" n FIG. 5)) in the target sequence.

Other chips provide additional probes (multiple-mutation probes) for analyzing target sequences having multiple closely spaced mutations. A multipe-mutation probe is usually identical to a corresponding probe from the first set as described above, except in the base occupying the interrogation position, and except at one or more additional positions, corresponding to nucleotides in which substitution may occur in the reference sequence. The one or more additional positions in the multiple mutation probe are occupied by nucleotides complementary to the nucleotides occupying corresponding positions in the reference sequence when the possible substitutions have occurred.

Another aspect of the invention derives hybridization patterns from a chip with a first probe set comprising a plurality of probes of perfect complemntarity to the reference sequence, and optionally, one or more additional probe sets, each additional set comprising probes corresponding to a probe in the first set with an interrogation position for a nucleotide of interest. The pobes in the additional probe sets differ from their corresponding probes in the first probe set by having a different nucleotide in the interrogation position. The overall hybridization is derived by plotting the maximum hybridization intensity observed from target hybridization to the group of probes consisting of a probe in the first probe set and its corresponding probes in the additional probe sets versus the nucleotide position of the target being interrogated by this group of probes. Thus, in this method, the probes are grouped according to groups in which all the probes in a particular group interrogate a common nucleotide position in the sequence being analyzed. These groups are referred to as groups of interrogatory probes. For example, with reference to FIG. 4, the first column of probes with interrogation position $I^1$ is interrogating position $n^1$, the second column of probes with interrogation position $I^2$ is interrogating position $n^2$ and so on. In the case described above in FIG. 1, where the corresponding probe from the first probe set has a T nucleotide in the interrogatio position and the corresponding probes from the other three probe sets have a C, G, and A nucleotide respectively, there would be a total of four probes interrogating the particular nucleotide of interest at that position of the sample sequence being analyzed. One measures the highest of the intensities observed from each of these probes and assigns that measured value as being the maximum hybridization intensity corresponding to that position of the sample sequence. This determination is then repeated iteratively for the remaining nucleotide positions of the sample sequence being anaylzed, allowing one to obtain a plot of hybridization intensity vs. nucleotide position.

It should be recognized that it is not necessary that there be additional sets of corresponding probes which interrogate all four possible nucleotide polymorphisms at a particular postion. The method described immediately above measures both the maximum hybridization intensity at a particular position and also how that maximum intensity changes from that position to the next adjacent position as one scans or "tiles through" the sequence of the target. Therefore, the chip can use a single probe set complementary to the reference sequence; multiple probe sets each of which interrogate a particular position in the target by varying the corresponding nucleotide of interest at that position; or even additional probe sets which are of different lengths to the first and additional probe sets comprising the first set of groups of interrogatory probes.

Figure 16A:
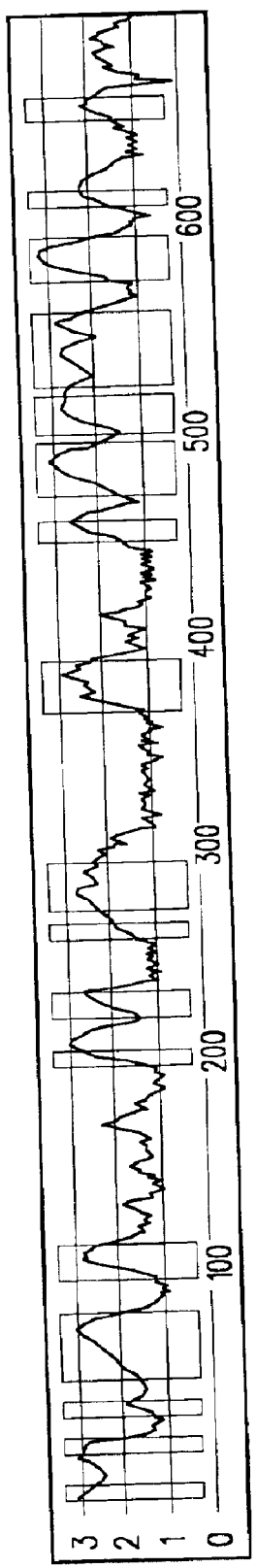
Figure 19C:
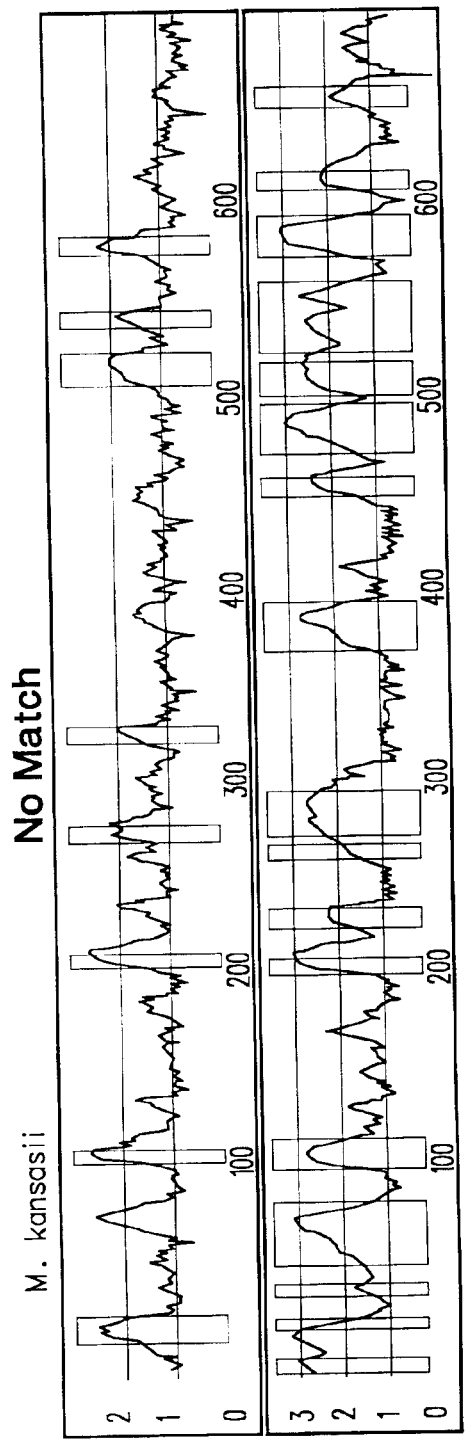
Figure 19D:
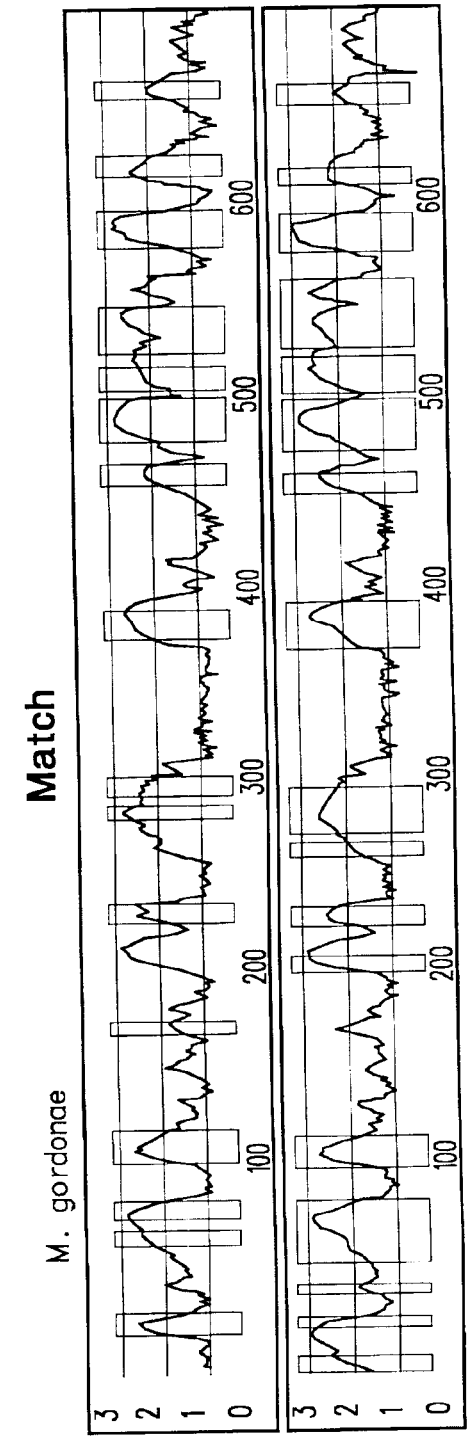

For example, one can use a chip with a single probe set complementary to the reference that tiles across the reference sequence. In this case, despite there being only one probe which interrogates a particular nucleotide position of the sample, one plots the hybridization intensity of that particular probe as a function of the nucleotide position being interrogated. In this case, there is no "maximum" hybridization intensity because each position is being "interrogated" by just one probe. However, one can still derive from the image plots of hybridization intensity as a function of nucleotide position of the sequence being analyzed and build up databases which correlate genotype with the derived plot. This method, using one set of probes (complementary to the reference sequence) is described in U.S. patent application Ser. No. 08/531,137, filed Oct. 16, 1995. A plot obtained from such a method is shown in FIG. 16. This entire plot is derived from the image gathered from a single hybridization experiment.

As the sample sequence being analyzed varies, the shape of this plot will also vary. For the purposes of clarity of explanation the following discussion uses a chip with probes complementary to a reference sequence from the *Mycobacterium tuberculosis rpoB* gene and the plot of maximum hybridization intensity derived from the image observed when the reference sequence (i.e., from an *M. tuberculosis* sample) is hybridized to the chip is clled the baseline or reference plot (or pattern). Target sequences from species of *Mycobacterium* other than tuberculosis will give plots of different shape. Hybridization experiments with targets of known speciation thus provides a database in which each of these differently shaped plots is correlated with speciation or other genotypic feature, which then in turns allows one to predict the presence of a phenotype. It should be apparent that any gene of interest can be tiled across the chip and that the hybridization pattern derived from the image on the chip from any other sample suspected of containing that gene or polymorphic variant thereof can be used to detect the presence or absence of a particular variant of that gene in the sample.

FIG. 16 shows the plot of hybridization intensity as a function of position being interrogated along the reference sequence for the case where the reference sequence is from the *Mycobacterium tuberculosis rpoB* gene (the Mtb chip described in the Examples) and the target is *M. gordonae*. FIG. 17 shows similar plots obtained with other *Mycobacterium* species. It is also noteworthy that species different to *M. tuberculosis* produce differences in hybridization intensity even from segments of the sequence which are identical to *M. tuberculosis*. Thus this method allows one to derive information even from subsequences that are identical to *M. tuberculosis*. As will be apparent, each species produces a characteristic pattern. One can pick the pattern obtained with the reference, in this case, the Mt rpoB, as being the baseline (or reference) pattern and overlay the pattern from the target over the pattern from the reference to detect differences from the reference. FIG. 18 shows such an overlay of patterns from different targets versus Mtb as observed on an Mtb chip. As one expects, when the target is *M. tuberculosis* (bottom panel) the overlay is perfect, whereas when the target is not *M. tuberculosis* differences are present. Each of these patterns is thus a "fingerprint" for that particular species. Once a database of fingerprints is established for one can compare the corresponding pattern obtained from an unknown target to either conclusively identify the target as being a particular species, or exclude the possibility of that target being any one of the species represented in the data base. FIGS. 19A, 19B, 19C and 19D show such a comparison of an unknown patient sample to fingerprints from four *Mycobacterium* species showing a match and thus identifying the unknown as being *M. gordonae*. FIG. 20 shows a similar identification of two other samples (6 and 7, previously incorrectly identified as *M. avium* by another technique) as *M. xenopi* and *M. intracellulare*.

As the above discussion indicates, there are several ways of plotting hybridization intensity versus nucleotide position of the sample, all of which provide patterns which are characteristic of a genotypic difference. As such, this invention is not limited using plots derived by the specific protocols disclosed herein. As explained earlier, identification of genotype and genotypic differences also allow the prediction of a phenotype.

It should also be recognized that the sequence used to generate the baseline pattern against which the target pattern is compared need not be that derived from a sample in which the reference sequence was hybridized to the chip. Any other sample that is related to the target sample may be used since the method compares differences between the baseline pattern and the pattern from the unknown target.

High density oligonucleotide arrays may be utilized to detect drug resistance conferring mutations using information gathered form gene regions utilized to identify species of isolates within the genus *Mycobacterium*. For example, the 700 base pairs of the rpoB gene of *Mycobacterium* may be utilized to detect mutations that confer resistance to rifampin and to detect polymorphisms which allow for the identification of *Mycobacterium* species.

Table 1B indicates the total polymorphic variation observed among the nine non-tuberculosis species compared to *M. tuberculosis* within the 700 base pairs of rpoB. With any of these non-tuberculosis species there are both species specific (base positions where observed polymorphisms found only with that species) and share (base positions which have polymorphisms found in some of the isolates of that species and some isolates of other *Mycobacterium* species). Virtually all of these polymorphisms have never been previously described and constitute useful and important markers for the identification of their corresponding species.

TABLE 1B

*Mycobacteria* Polymorphic Analysis

| Species | Total Polymorphisms | Species Specific | Shared |
|---|---|---|---|
| M. avium | 72 | 3 | 69 |
| M. chelonae | 106 | 8 | 48 |
| M. fortuitum | 103 | 21 | 81 |
| M. gordonae | 102 | 26 | 76 |
| M. intracellulare | 59 | 3 | 56 |
| M. kansasii | 84 | 12 | 72 |
| M. scrofulaceum | 62 | 2 | 60 |
| M. smegmatis | 101 | 10 | 91 |
| M. xenopii | 73 | 13 | 60 |

16SrRNA sequences are commonly utilized to identify species of *Mycobacterium*. However, analysis of the hybridization pattern using the rpoB gene indicates that there are some isolates that have been misclassified. For example, two *Mycobacterium* isolates received from the California Public Health department, 96-1761 and 95-1760, were indicated as *M. avium* isolates. When the rpoB gene is utilized, it was determined that the most similar match was with *M. intracellulare* (a close relaitve of *M. avium*).

The following will describe an embodiment that identifies the species within a genus to which an organism belongs. However, the process is generally applicable to assigning groups to organisms, where the groups may be species, subspecies, phenotypes, genotypes, and the like. Accordingly, the description that follows illustrates one embodiment of the invention.

FIG. 34 shows a computer-implemented flowchart of a method of identifying a species within a genus to which an organism belongs. At step 300, species of nucleic acid sequences from known organisms are input. These nucleic acid sequences will be called "known nucleic acid sequences." Additionally, at step 302, hybridization patterns for the known nucleic acid sequences. The hybridization patterns indicate the hybridization affinity of subsequences of the known nucleic acid sequences to subsequences of a reference nucleic acid sequence. For example, the subsequences of the reference nucleic acid sequence may be portions of nucleic acid probes on a chip.

At step 304, a database of the species and hybridization patterns of the known nucleic acid sequences may be generated. As with other steps, this step is optional but may make identifying species more efficient.

The system compares the hybridization pattern of a sample nucleic acid sequence to the hybridization patterns for the known nucleic acid sequences at step 308, which may be optionally stored in a database. At step 308, the system determines the species of the organism from which the sample nucleic acid was obtained according to the hybridization pattern of the known nucleic acid sequences that most closely matches the hybridization pattern of the sample nucleic acid at specific locations. Although an overall pattern matching technique may be utilized, one may alos analyze species specific polymorphic locations and/or shared polymorphic locations. Additionally, it may be a combination of hybridization patterns that are utilized to identify the species of the sample nucleic acid sequence.

Comparing the hybridization patterns may be done in any number of known techniques. In a preferred embodiment, linear regression is utilized across all or selected base positions to normalize the hybridization intensities. A regression coefficient from the linear regression is then utilized to measure the closeness of the hybridization intensities of the hybridization patterns and thretore, the nucleic acid sequences. Additionally, depending on how closely the hybridization pattern of the sample nucleic acid matches a hybridization pattern of the known nucleic acid sequences, the system may calculate a probability that the identified species for the sample is correct as indicated at step 310.

Again referring to FIG. 18, the figure shows plots of hybridization intensities of *Mycobacteria* species. A DNA assay was designed for *Mycobacteria tuberculosis* (Mtb) as the chip wild-type sequence. This chip will be referred to as the Mtb chip to indicate that the chip was tiled for Mtb. In other words, in addition to other probes, there are probes that are perfectly complementary to Mtb at sequential base locations. These probes will be referred to as the wild-type probes or probes complementary to the reference sequence.

Mtb was hybridized to the Mtb chip and the hybridization intensities of the wild-type probes (here measured as a logarithmic function of the photon counts) vs. the base portion is shown in the bottom graph identified as "Mtb vs. *M. tuberculosis*." The graph illustrates an example of a hybridization pattern for Mtb. As indicated by the title of the graph, the graph actually shows the Mtb hybridization intensity pattern vs. itself so that there are actually two hybridization patterns superimposed on each other. In the following paragraphs, the Mtb sequence will be identified as the reference sequence (i.e., is typically a known sequence).

There are many species of *Mycobacteria*. Numerous species were hybridized to the Mtb chip and the graphs in FIG. 19 show the hybridization intensities of the wild-type probes (again measured as a logarithmic function of the photon counts) vs. the base position. In addition to the hybridization pattern for the *Mycobacteria* species, each graph also shows the hybridization pattern for the reference sequence, Mtb.

Although 80% of the bases of the different *Mycobacteria* species may be the same, each species generates a unique hybridization pattern or footprint. A sample sequence which is known to be a *Mycobacteria* species (e.g., from previous base calling algorithms or dideoxy sequencing) may be similarly hybridized to the Mtb chip. The hybridization pattern that results may be compared to the hybridization patterns of known sequences to determine the identity of the sample sequence.

The *Mycobacteria* species themselves (or other species) may have enough similarities that the base calling algorithm is able to identify the sample as a *Mycobacteria* species. The species may also have enough differences that this method is able to identify the species according to the hybridization pattern.

Although in this example, the chip-wild type sequence and the reference sequence were the same sequence, different sequences may be utilized. The hybridization patterns discussed were generated by the hybridization intensities of the wild-type probes. However, hybridization patterns may be generated other ways including utilizing hybridization intensities of the highest intensity probe at each base position. Additionally, the method may be utilized on other species or even unrelated nucleic acid sequences to identify a sample sequence.

Figure 21:
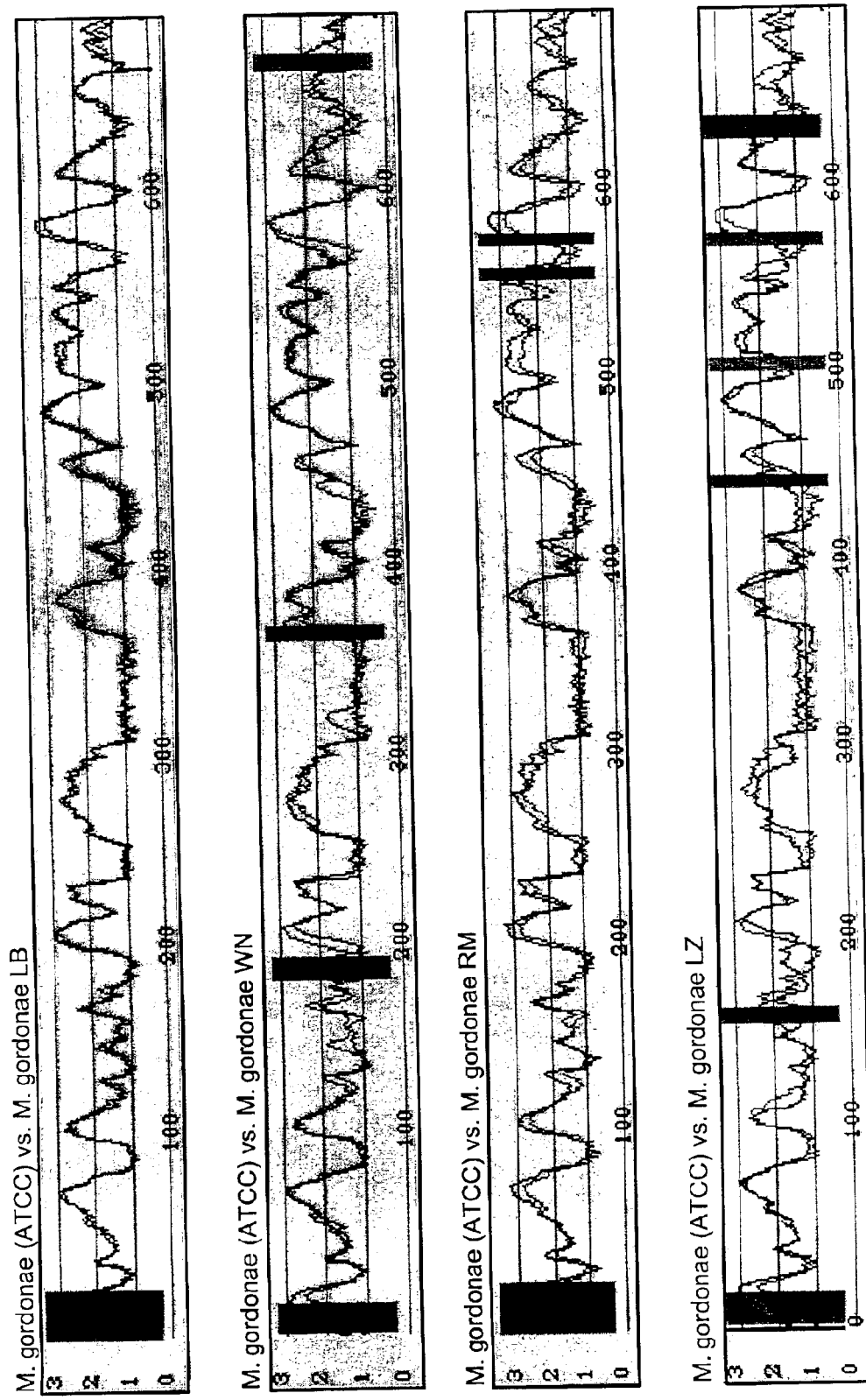

Typically, the hybridization differences observed between different species are large, whereas, as expected, the differences between different isolates of the same species are smaller. Therefore, one can set the cut off of the discriminating pattern matching function to whatever predetermined level is desired, depending on whether one is attempting to assign speciation or track an isolate. FIG. 21 shows the patterns observed with different isolates of *M. gordonae* and their comparison to a single isolate of *M. gordonae* (ATCC isolate).

It should be noted that derivation of hybridization intensity vs. nucleotide position patterns and their correlation with patterns of known identity does not require that one identify the base present at particular position of the target or sequence the target. Instead, one determines the maximum hybridization intensity observed from any of the one or more probes which are interrogating for the presence of nucleotide identical to that of the reference sequence at the corresponding position in the target and plots how this changes as a function of base position. The pattern thus obtained is compared to a database of patterns from organisms of known speciation to establish the presence or absence of match. Thus, there is no necessity to "call" or identify any of the bases in the target sequence in order to make an assignment.

Once differences between the target sequence pattern and the baseline reference pattern are established, these differences can be used in the same manner as the presence of differences in nucleotide sequence between target and reference to derive probabilities that the presence of a certain level of difference in hybridization intensity at a particular position indicate a certain species or genotype. All the observed differences from the reference can then be combined to give a composite probability of the sample being of a particular species or genotype. Thus, derivation of these patterns of hybridization also allows the use of the "bar code" type of identification method described earlier. As FIG. 16 shows, using patterns derived from hybridization intensity allows one to obtain information from the entire sequence, not just the regions where the sequence of the target differs from that of the reference.

One advantage of this method of pattern matching is that provided the same set of probes is used on a chip, one can use different chips at different times and with different concentrations of sample to make the assignment because each different species will produce the same and invariant hybridization pattern. For example, one does not need to derive a control pattern from the reference sequence simultaneous with the analysis of the target to comparing the two patterns (target vs. reference sequence), since the control pattern is invariant and the pattern matching looks at the relative changes in maximum hybridization intensities between succeeding base positions along the sequence. Thus, factors such as amplification conditions and sample concentration which would affect hybridization at all sites equally can be normalized during the analysis.

One will recognize that this method of using oligonucleotide arrays with such pattern matching techniques is generally applicable to reference sequences other than the rpoB gene and can be used to detect any differences between a target and reference sequence from any gene. By way of example, and not limitation, the reference sequence can be from a gene coding for an HIV gene, breast cancer (BRCA-1) or for cystic fibrosis. Software is used to plot the hybridization intensities and compare the pattern so derived to a pattern from the reference or other sequence to establish differences between the target and reference, identity or lack thereof of target to sequence in the database of patterns.

Polynucleotide sequence can be represented as an assembly of overlapping oligonucleotides. Therefore, an array consisting of the set of complementary oligonucleotides to a specific sequence can be used to determine the identity of a target sequence, quantitate the amount of the target, or detect differences between the target sequence and a reference. Many different arrays can be designed for these purposes. One such design, termed a tiled array, is depicted schematically in FIG. 22A.

The use of a tiled array of probes to read a target sequence is illustrated in FIG. 22B. A $p^{15,7}$ (15-mers varied at position 7 from the 3' end) tiled array was designed and synthesized against MT1, a cloned sequence containing 1,311 bases spanning the D-loop, or control region of the human mitochondrial DNA. The upper image panel of FIG. 22B shows a portion of the fluorescence image of $mt^1$ fluorescein labelled RNA hybridized to the array. The base sequence can be read by comparing the intensities of the four probes within each column. For example, the column labelled 16,493 consists of the four probes, 3' TGACAT AGGCTGTAG (SEQ ID NO:1), 3' TGACATCGGCTGTAG (SEQ ID NO:2), 3' TGACATGGGCTGTAG (SEQ ID NO:3), 3' TGACATTGGCTGTAG (SEQ ID NO:4). The probe with the strongest signal is the probe with the A substitution (A 301, C 57, G 135, T 110 counts), identifying the base at position 16,493 as a U (complementary to the A probe) in the RNA transcript. Continuing the process, the rest of the sequence can be read directly from the hybridization intensities.

The detection of a single base polymorphism is shown in the lower image panel of FIG. 23B. The target hybridized in the lower panel is MT2, which differs from MT1 in this region by a T to C transition at position 16,493. Accordingly, the probe with the G substitution shows the strongest signal. Since the tiled array was designed to MT1, neighboring probes which overlap 16,493 are also affected by the change. Because 15-mer probes are used, a total of 15 columns, or 60 probes, are affected by a single base change in the target. In the $p^{15,7}$ array, probes in the 8 positions to the left and 6 positions to the right of the probe set interrogating the mutation have an additional mismatch to the target. The result is a characteristic "footprint", or loss of signal in the probes flanking a mutation position, reminiscent of the U shaped curve of FIG. 23. (The data shown in FIG. 23 are for 8 mer probes, but we have been able to discriminate single base end position mismatches from perfect matches even using 20 mers). Of the four interrogation probes at each position, signal loss is greatest from the probe designed to have zero mismatches to MT1. We identify the set of these designed probes as $p^{015,7}$ or simply $P^0$. In the other three probe sets, designated $p^1$, the MT1 signal is already low as a result of the single base mismatch at the interrogation position.

Comparative Hybridization and Multi-Color Detection

Figure 22:

Patterns of signal intensities and their differences resulting from mismatches, such as the example shown in FIG. 22, can be used to advantage in sequence analysis. The loss of hybridization signal from $P^0$ is a powerful indicator of sequence difference between reference and target. This information is best obtained by hybridizing both the reference and the target sequence simultaneously to the same array. In order to extract the maximum amount of useful information from a simple tiled array, we developed a two-color labelling and detection scheme, allowing us to use as an internal standard the hybridization of a reference sample of known sequence (FIG. 24). The reference is labelled with phycoerythrin (red) and the unknown target with fluorescein (green). This approach minimizes or eliminates experimental variability during the fragmentation, hybridization, washing, and detection steps. A further advantage is that the sample and reference targets are in competition, enhancing mismatch discrimination.

It is also possible to perform the experiment by hybridizing the reference and unknown to two different chips in parallel under identical conditions. In this case, only a single label is required. Using either approach, differences between two related sequences can be identified from a straightforward comparison of the scaled hybridization patterns of the $p^0$ probes. Difference in $p^0$ intensities resulting from a polymorphism extend over a number of positions and correlate with probe length and substitution position (FIG. 24). This characteristic large-scale pattern is more robust and easier to recognize than an intensity difference at a single position. Since the amplitude of each $p^0$ signal is sequence and mismatch dependent, the actual size and shape of footprints is variable. Thus, sequences can be identified by directly comparing hybridization amplitude signatures, rather than by comparing analyzed sequences, which may contain embedded errors of interpretation. Hybridization pattern analysis may provide advantages over other methods of detecting sequence variation, or in some cases may be useful in conjunction with them.

Polymorphism Screening of the Cytochrome b Gene and Control Region

We have shown how a $p^0$ probe set in conjunction with a reference hybridization pattern can be used to analyze sequences over much larger spans than 600 bp, and how single base polymorphisms can be read using a tiled array. We combined the two approaches and used array hybridization patterns to perform automated basecalling from complex target sequences. The combination was useful in overcoming most difficulties. For example, some sequences can cross-hybridize significantly, particularly when the target is long and repetitive on a fine scale, or GC rich, even locally. By analyzing targets in terms of differences from a reference of known sequence, many potentially confusing signals could be disregarded because they were the same in both samples. A second limitation is that if two or more polymorphisms occur within a single probe span, the resulting destabilization tends to reduce the accuracy of sequence interpretation, although the existence of a change can easily be inferred from the loss of signal (FIG. 24). We adopted an approach that simply identifies such regions for further analysis, rather than attempting to read them directly.

After applying an automated basecalling algorithm, which uses all four interrogation probes for each position and compares the reference and sample hybridization intensities the derived sequences were separated into two categories: one that could be read directly with high accuracy, and a second that required further analysis for definitive sequence assignment. The first category was defined as having a derived sequence with no more than a single mismatch with each $p^0$ probe, and agreement between the derived sequence and $p^0$ footprint patterns.

The $p^0$ intensity footprints were detected in the following way: the reference and sample intensities were normalized, and R, the average of log 10 ($p^0$ reference/$p^0$ sample) over a window of 5 positions, centered at the base of interest, calculated for each position in the sequence. To normalize the sample probe intensities to the reference intensities, a histogram of the base 10 logarithm of the intensity ratios for each pair of probes was constructed. The histogram has a mesh size of 0.01, and was smoothed by replacing the value at each point with the average number of counts over a five-point window centered at that point. The highest value in the histogram was located, and the resulting intensity ratio was taken to be the most probable calibration coefficient. Footprints were detected as regions having at least 5 contiguous positions with a reference or sample intensity of at least 50 counts above background, and an R value in the top 10th percentile for the experiment. At 205 polymorphic sites, where the sample was mismatched to $p^0$, the mean R value was 1.01, with a standard deviation of 0.57. At 35,333 non polymorphic sites (i.e., where both reference and sample had a perfect match to $p^0$) the mean R value was −0.05, with a standard deviation of 0.25.

The second category had a derived sequence with multiple mismatches and/or disagreement between derived sequence and $p^0$ patterns. For example, the region of iefOO7 shown in FIG. 24A would fall into the first category, if the sequence were called correctly. A false positive basecall would lack a footprint or would result in the prediction of multiple mismatched probes, and be flagged in either case. False negatives are detected by the presence of a footprint despite a "wild-type" basecall.

An example of a false negative basecall resulting from the use of a limited probe set is shown in FIG. 25A. In this case, there is a $(CA)_n$ length polymorphism, where n=4 in MT2 and n=5 in the reference, MT1. The array is designed to read $(CA)_5$, but the MT2 target hybridizes sufficiently well to be read as "wild type". However, a footprint is detected, and therefore, the region is flagged for further analysis, some differences in hybridization patterns are secondary effects of a change elsewhere in the target. An example that is likely due to a sequence-specific difference in target secondary structure is shown in FIG. 25A. This example shows that the interpretation of difference patterns is not always straightforward. In general, however, the difference patterns provide a substantial amount of additional information that aids sequence analysis.

We analyzed a 2.5 kb region of MT DNA spanning the $tRNA^{Glu,Thr}$, cytochrome b, $tRNA^{Thr}$, $tRNA^{Pro}$, control region and $tRNA^{Phe}$ DNA sequences. These sequences have very different functions ranging from protein coding to tRNA structure to regulatory, and should therefore provide a good comparative basis for evaluating the different mutation rates of MT DNA. The $p^{20,9}$ tiling array was used to analyze a total of 12 samples containing 180 (0.59%) base substitutions relative to MT1. The results are presented in Table 1A. Of the 30,582 bp analyzed, base substitutions were read in 98% of the sequence with >99% accuracy without user intervention. No false positive calls were made. The remaining 2% of sequence was flagged for further analysis. This indicates a very high rate of accuracy, which was obtained for the analysis of 2.5 kb of sequence at one time. Thus, while the more mature gel-based technology was able to read clustered and length polymorphisms, hybridization to a 4N tiled array yielded comparable results over most of the sequence with considerably less effort.

hybridization intensity values was computed by comparing an unknown set of probes to a set of example cases for which the correct basecall was known. The resulting four likelihoods were then normalized so that they summed to 1. Data from both strands were combined by averaging the values. If the most likely basecall had an average normalized

TABLE 1A

Sequence analysis results.

|  | Polymorphic Sites[a] | | | | Non-polymorphic Sites | | | |
| --- | --- | --- | --- | --- | --- | --- | --- | --- |
|  | TOTAL | | Called[b] | | TOTAL | | Called | |
| Mismatches[c] | 0 | ≧1 | 0 | ≧1 | 0 | ≧ | 0 | ≧ |
| All Positions | 134 | 46 | 130 | 35 | 26883 | 3465 | 26883 | 3457 |
| Unflagged Regions | 126 | 1 | 126 | 0 | 26732 | 3020 | 26732 | 3020 |
| Flagged Regions | 8 | 45 | 4 | 35 | 151 | 445 | 151 | 437 |

[a]Sequence differences relative to the MT1 reference sample. A common length polymorphism at position 310 was not detected under the conditions used and was excluded from this analysis. However, this polymorphic size has previously been shown to be amenable to screening by oligonucleotide hybridization.
[b]Number of sequence positions called correctly by automated basecaller.
[c]The $p^0$ probe for each target base is either perfectly matched to the target (0) or has c I mismatches as a result of neighboring polymorphisms.

A total of 12 samples containing 180 substitutions relative to mt1 was analyzed (mt3, mt4, mt5, mt6, ha001, ha002, ha004, ha007, ief002, ief007, ief011 and yr019). Results are summed for all 12 samples. All but two of the 180 substitutions were detected as po intensity differences (one of the exceptions was read correctly by basecalling and automatically flagged for further analysis). In total, only 649 bp (2% of the sequence analyzed) were flagged for further analysis. Basecalling results are broken down separately for unflagged and flagged regions. Fully automated basecalling in unflagged regions had an error rate of 1/127 polymorphisms or 1/29,879 total bp. In contrast, flagged regions, which included 53 (29%) of the substitutions contained 14 false negatives and 8 false positive. However, we estimated that, on average, 2 to 3 conventional sequencing reactions per sample, or ~30 reactions in total, would resolve the flagged regions, to give a basecalling accuracy in excess of 99.9% for the entire sequence. This represents 8-fold less sequencing than we used to determine the sequences by conventional methods alone and a similar saving in the labor intensive task of sequence checking and editing. In this experiment, samples were prepared and hybridized as described in FIG. 24. In order to provide an independently determined reference sequence, each 2.5 kb PCR amplicon was sequenced on both strands by primer-directed fluorescent chain-terminator cycle sequencing using an ABI373A DNA sequencer, and assembled and manually edited using Sequencher 3.0. Hybridization analysis was also performed on both strands. The analysis presented here assumes that the sequence amplified from genomic DNA is essentially clonal, or at least contains one predominant species, and that its determination by gel-based methods is correct. PCR amplification errors might contribute a maximum of ~0.5% sequence difference, essentially randomly distributed, based on an estimation of ~$10^5$ fold amplification and known error rates of Taq polymerase. This would not be expected to affect significantly the results of gel based sequencing or hybridization analysis, particularly when analyzing differences from a reference hybridization pattern.

Basecalling was performed using a Bayesian classification algorithm based on variable kernel density estimation. The likelihood of each basecall associated with a set of likelihood of greater than 0.6, it was called, otherwise the base was called an ambiguity. The example set was derived from 2 different samples, ib013 and ief005, which have a total of 35 substitutions relative to MT1 of which 19 are shared with the 12 samples analyzed and 16 are not. Base calling performance was not sensitive to the choice of samples. The hybridization sequence analysis was fully automated, with no user editing. In contrast, conventional sequencing required contig assembly followed by editing, in which >1% of basecalls were manually corrected.

High Density Oligonucleotide Arrays

Several technologies have been developed to design, synthesize, hybridize and interpret high density oligonucleotide arrays of the type described above. Representative arrays are described in described in U.S. Pat. No. 5,143,854 and PCT patent publication Nos. WO 90/15070 and WO 92/10092, each of which is incorporated herein by reference. Often, arrays have a lower limit of 25, 50 or 100 probes and an upper limit of 1,000,000, 100,00, 10,000 or 1,000 probes. A range of lengths of probes may be employed. Preferably, each of the high density oligonucleotide arrays contain 10,000–20,000 oligonucleotide probes (length 10–20 mers) which are used to determine the sequence of a target nucleic acid (RNA or DNA). Frequently, the density of the different oligonucleotides is greater than about 60 different oligonucleotides per 1 $cm^2$. The determination of a target sequence is accomplished by carrying out a single hybridization reaction involving all of the probes on the surface of the chip. The following is a brief overview describing the synthesis, array design, sample preparation/fluorescent labeling and base calling features of the DNA chips used in this invention.

Light Directed Synthesis

Figure 6:
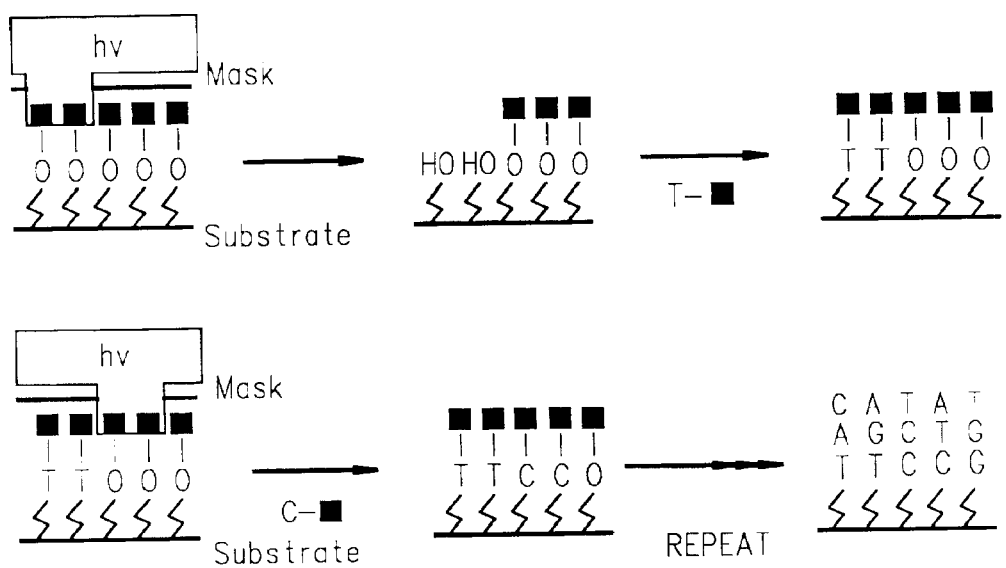
FIG. 6: Shows the light directed synthesis of oligonucleotide probes on a substrate.

DNA chips use light directed synthesis to build oligonucleotide probes on the surface of the chip (Fodor, et al., *Science,* 251:767–73 (1991)). This light-directed synthesis combines semiconductor based photolithography and solid phase chemical synthesis. With reference to FIG. 6, the process begins when linkers modified with photochemically removable protecting groups (C) are attached to a solid substrate, the chip surface. Linkers and phosphoramidites with photolabile protecting groups have been synthesized and are described by Pease, et al., *PNAS*, 91:11241–11245 (1994). Light is directed through a photolithographic mask to specific areas of the synthesis surface, activating those areas for subsequent chemical coupling. The first of a series of nucleotides (T in FIG. 6) possessing photolabile protecting groups, is incubated with the chip and chemical coupling occurs at those sites which have been illuminated in the preceding step. Light is then directed through a different section of the mask to the next synthesis site and the chemical steps, a defined collection of oligonucleotide probes can be constructed, each having its own unique address on the surface of the chip.

Synthesis of Complete and Subset-Combinatorial Arrays

In a light-directed synthesis, the location and composition of the oligonucleotide products depends upon the pattern of illumination and the order of chemical coupling reagents. Consider the synthesis of a chip containing all possible tetranucleotide oligomers (256 possibilities) (FIG. 7). In cycle 1, mask 1 activates one fourth of the substrate surface (dT). In round 2 of cycle 1, mask 2 activates a different quarter of the substrate for coupling with the second nucleoside (dC). This process is continued to build four regions of mononucleotides. The masks of cycle 2 are perpendicular to those of cycle 1, and each synthesis round generates four new dinucleotides until all 16 possible dinucleotides are made (FIG. 7). The masks of cycle 3 further subdivide the synthesis regions so that each coupling round generates 16 trimers. The subdivision of the substrate is continued through cycle 4 to form all possible 256 tetramers (complete combinatorial array). The successful demonstration of light-directed complete combinatorial array has recently been described (Pease, et al., *PNAS*, 91:11241–11245 (1994)). It is important to note that any subset of a complete array can be synthesized by modifying the mask patterns used in each cycle and round of synthesis. The complete combinatorial arrays can be used for applications in which de novo sequencing is sought (Fodor, et al., 1993), while a subset of combinatorial arrays can be used for resequencing applications such as will be employed in this application.

Sample Preparation, and Fluorescent Labeling of Target Nucleic Acid

Figure 8:
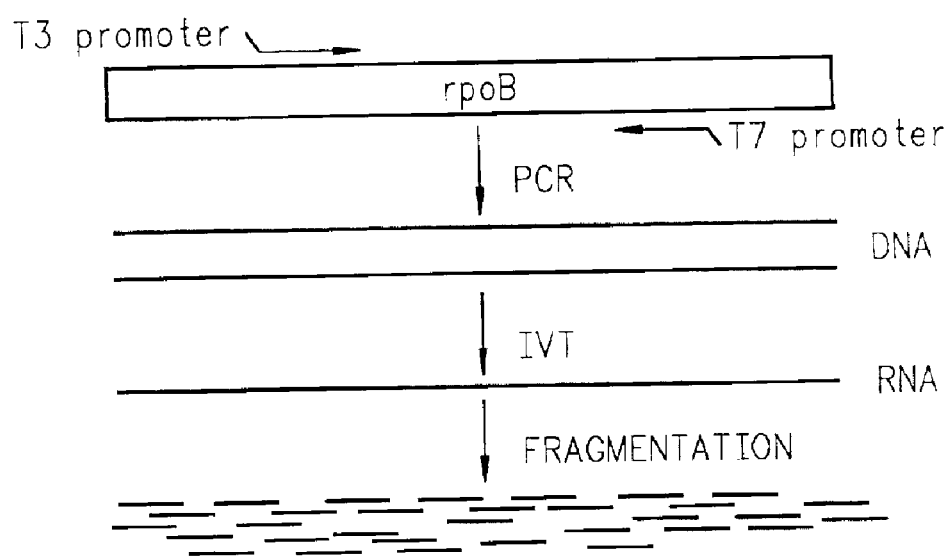
FIG. 8: A schematic diagram of target preparation.

Oligonucleotide arrays hybridized to amplification-generated fluorescently-labeled DNA or RNA and the hybridizations are detected by epi-fluorescence confocal microscopy (Fodor, et al., 1993; Molecular Dynamics, Santa Clara, Calif.). This process is initiated by the extraction of target nucleic acids from the sample. With reference to FIG. 8, the target nucleic acid (mycobacterium genomic DNA) is amplified by the polymerase chain reaction (PCR) using target gene specific primer pairs containing bacteriophage RNA polymerase promoter sequences (FIG. 8). PCR amplified copies of the target nucleic acid are converted from double stranded (ds) DNA into fluorescently-labeled single stranded (ss) RNA during an in vitro transcription (IVT) reaction. Finally, the fluorescein-labeled target gene specific RNA transcripts are fragmented into oligomer length targets under elevated temperature and 30 mM $Mg^{++}$. The precise protocols, primers and conditions for sample extraction, amplification, chip hybridization and analysis are described in the Examples. Of course other labelling strategies may be utilized.

Resequencing Chips and Detection of Single Base Mismatches

As described earlier, a target gene sequence can be represented on a chip in a series of overlapping oligonucleotide probes arrayed in a tiling strategy (FIG. 9). In such a strategy each base in the target is interrogated by using a collection of 4 oligonucleotide probes which are identical except for the base located at or near the center of the probe. Each of the four probes contains dA, dT, dC or dG at this interrogation position. Of the four oligonucleotide probes the one which is the exact complement will produce the most stable hybrid and thus the strongest fluorescent signal after post-hybridization washing the DNA chip. Likewise, the next nucleotide in the target sequence can be interrogated with four identical length probes which are the same as the first four except they are offset one nucleotide downstream. The central base of these probes also have all four possible bases. In like fashion, all of the bases of a target sequence can be interrogated using overlapping probes arranged in a tiling strategy. The determination of which of the four possible probes is the complement to target is made by taking the ratio of highest to next highest hybridization signal. If this ratio is greater than 1.2, then a specific determination of the interrogated base can be made. If the highest hybridization signal does not meet this criteria then an ambiguous determination is made based on the IUPAC sequence codes.

Figure 10:
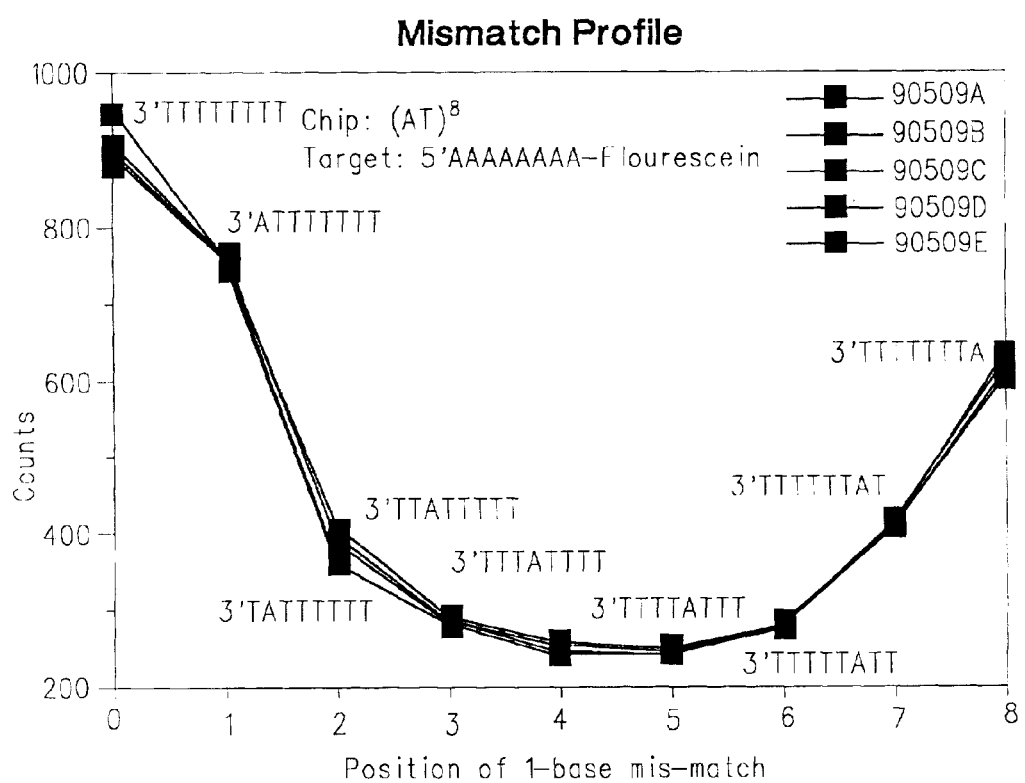
FIG. 10: A mismatch profile for an octamer based chip.

The sensitivity of DNA chip probes to detect single base mismatches is illustrated using a 16 step combinatorial synthesis. The photolabile MenPoc-dA and MenPoc-dT were the only nucleotides used during the synthesis of the probes on the chip. The lithographic masks were chosen such that each of 256 octanucleotides were synthesized in four independent locations on a 1.28×1.28 cm chip surface. This yielded an array of 1024 octanucleotides each occupying a 400×400 $\mu$m synthesis region. Following synthesis and phenoxyacetyl deprotection of the dA amine, the glass substrate was mounted in a thermostatically regulated hybridization cell. The target employed for this experiment was an oligonucleotide 5'-AAAAAAAA-fluorescein-3' present in a 1 nM concentration. After 30 minute hybridization and washes with ×1.0 SSPE at 15° C., the chip was scanned using an epi-fluorescent confocal reader. The fluorescent intensities of each of the hybridization events were plotted against the position of the mismatches of the probes on the surface of the chip (FIG. 10). The position zero mismatch (with the perfect complement 3'-TTTTTTTT-5') is the brightest hybridization on the array with the background signal of this array at approximately 220 counts. Mismatch position 1 (at the 3' end of the probe) (3'-ATTTTTTT-5') is the next highest hybridization. The resulting "U" shaped curve indicates the relative stability of the mismatches at each position of the probe/target complex. The mismatches at positions 3, 4, 5 and 6 are very destabilizing and the intensities of these hybridizations are approximately 3 fold lower than the perfect match hybridization. It is also noteworthy that the mismatch at position 1 (the point where the octanucleotide is tethered to the chip substrate) is less destabilizing than the corresponding mismatch at position 8 (5' free end). The uniformity of the array synthesis and the target hybridization is reflected in the low variance of the intensities of the four duplicate synthesis sites.

Pattern Recognition Algorithm

Hybridization patterns derived from the oligonucleotide probe arrays can be correlated with the drug resistance phenotype and speciation of the organism using mathematical pattern recognition algorithms, such as tree-structured classification techniques. It is important to note that as the total number of analyzed isolates for each species is increased, it is unlikely that a single and unique core fingerprint will define a *mycobacterium* species. Rather, it is expected that any particular isolate of a *Mycobacterium* species will have a subset of all possible fingerprints. Identification of the *Mycobacterium* species based on a fingerprint pattern will require a classification analysis built upon a collected database consisting of species specific and shared SNPs and fingerprints.

The goal of identifying an unknown rpoB hybridization pattern as coming from one of the *Mycobacterium* species in the data base is a general classification problem. Measurements (sequence and fingerprint data) are made on a collection of samples. Based on these measurements a systematic way is developed to predict the class (species) of each member of the collection. The signal produced by the target at each hybridization site is compared to the signal produced by MT rpoB. Based on this comparison one determines whether or not there is a difference in genotype at the interrogated at that site in the target relative to MT rpoB.

Classifier construction is based on past experience. In systematic classifier construction, past experience is summarized by a learning sample (a.k.a. design or training sample). This consists of the measurement data on N cases observed in the past together with their actual classification. It is intended that the database collected in Phase I will serve as the initial training sample. There are two general types of variables that can appear in the measurement data, ordered or numerical variables and categorical variables. A variable is called ordered or numerical if its measured values are real numbers. A variable is categorical if it takes values in a finite set not having any natural ordering. In our case, each nucleotide position in the sequence is a variable. So all measurement variables are categorical. The set of measurement variable for a given case is called the measurement vector. The measurement space is defined as the set of all possible measurement vectors.

The four most commonly used classification procedures are discriminant analysis, kernel density estimation, and kth nearest neighbor, and tree-structured classification. Discriminant analysis assumes that all the measurement vectors are distributed multivariate normal, and thus is not set up to handle categorical variables (See Gnanadesikan, R. *Methods for statistical data analysis of multivariate observations* (Wiley, New York (1977)). Even though kernel density estimation and kth nearest neighbor methods make minimal assumptions about the form of the underlying distribution of the measurement vectors, there are still serious limitations common to both methods. They require a definition of a distance measure (metric) among the measurement vectors; performance of these classifiers is sensitive to the choice of the metric. There is no natural or simple way to handle categorical variables. Both are computationally expensive as classifiers because they require that the learning sample be stored, and the distances and classification rule be recomputed for each new undetermined case. Most seriously, they give very little usable information about the data structure. Kanal, L. (1974) *IEEE Trans. Information Theory* IT-20:697–722, and Hand, D. J. *Discrimination and Classification* (Wiley, Chichester (1981)), give surveys of the literature on these methods.

Tree-structured classification is a recursive and iterative procedure. It proceeds by repeated splits of subsets of the measurement space into two descendant subsets or nodes, beginning with the full measurement space. The fundamental approach is to select each split of a node so that the data in each of the descendant nodes are "purer" than the data in the parent node. A node impurity measure is defined such that it is largest when all classes are equally mixed together in that node, and smallest when the node contains only one class. The sequence of splits is determined such that at each candidate node all possible splits are examined and the split that produces the largest decrease in the impurity is selected. The terminal nodes form a partition of the measurement space. Each terminal node is designated by a class assignment based on the observed proportions of the classes in that partition. (Usually, the assignment is the class with the highest proportion.) There may be two or more terminal nodes with the same class assignment. The partition corresponding to that class is obtained by putting together all terminal nodes corresponding to the same class. The tree classifier predicts a class for a given measurement vector in the following way: From the definition of the first split, it is determined whether the measurement vector goes to the right or to the left. This is repeated until the case moves into a terminal node. The predicted class is then given by the class assignment of that terminal node.

The optimal size of a classification tree is determined in the following manner: continue the splitting until all terminal nodes are very small, resulting in a large tree. This large tree is then selectively pruned upward, and thus producing a decreasing sequence of subtrees. Finally, use cross-validation or test-sample estimates to choose from the sequence of subtrees that subtree having the lowest estimated misclassification rate. The tree-structured classification methodology is covered in detail in Breiman et. al. *Classification and Regression Trees,* (Wadsworth International Group, Belmont, Calif. (1984)).

The tree-structured approach is a powerful and flexible classification tool. It can handle both numerical and categorical variables in a simple and natural way. The final classification has a simple form that can be efficiently used to classify new data. It does automatic stepwise variable selection and complexity reduction. It provides both the classification and the estimate of the misclassification probability for a new case. The output of the tree procedure gives easily understood and interpreted information regarding the predictive structure of the data.

Example of a Tree-Structured Classifier

Figure 11:
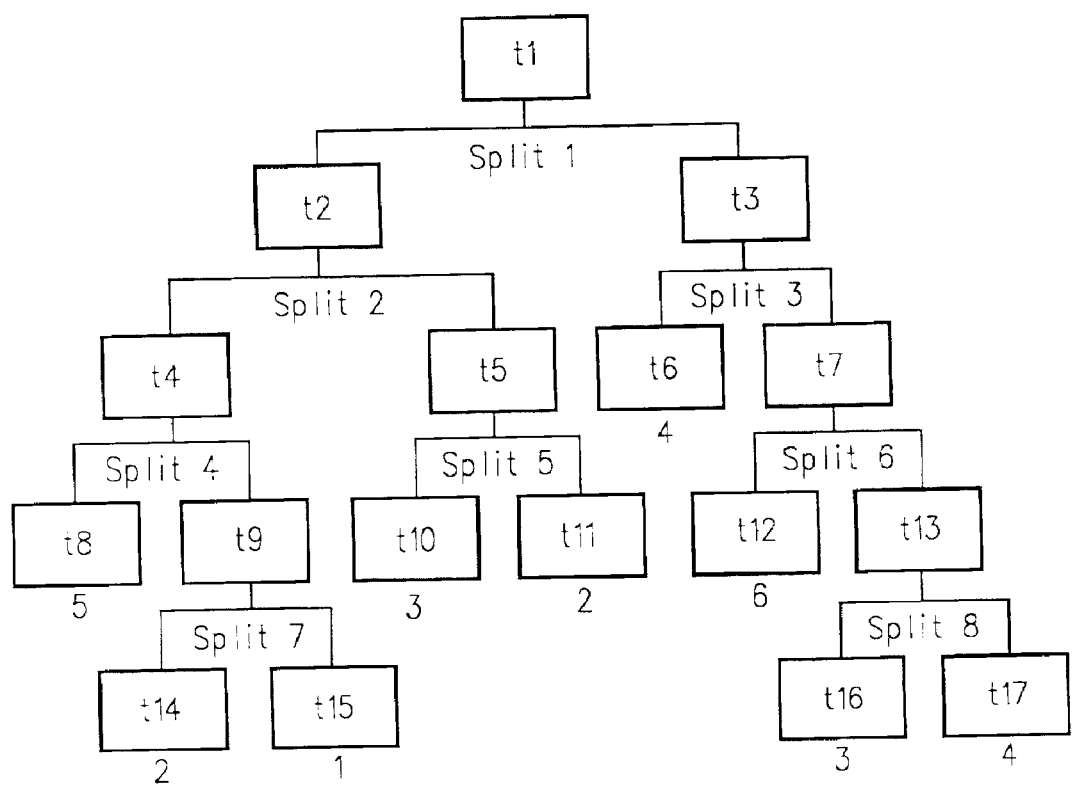
FIG. 11: A hypothetical six-class tree based classification system. The numbers underneath the terminal nodes are the class assignments as determined by this classifier.

FIG. 11 displays a hypothetical six-class tree (numbers under boxes). The boxes represent nodes. Node t1 contains the whole measurement space and is called the root node. Nodes t2 and t3 are disjoint with t1 being the union of t2 and t3. Similarly t4 and t5 are disjoint and t2 is the union of t4 and t5. Those nodes that are not split, in this case, t6, t8, t10, t11, t12, t14, t15, t16, and t17 are called terminal nodes. The numbers beneath the terminal nodes are the class assignments or class labels for this particular classifier.

Let x be a measurement vector (in our case a DNA sequence of length K); $x=(x_1, x_2, \ldots, x_K)$. The splits are formed by setting conditions on the coordinates of x. For example Split 1 of t1 into t2 and t3 could be of the form: t2 is the set of measurement vectors such that $x_{10}=\{A, C\}$ and t3 is the set of measurement vectors such that $x_{10}=\{G, T\}$.

This classifier predicts a class for the measurement vector x in this way: From the definition of the first split, it is determined whether x goes into t2 or t3. For example, if the above definition for Split 1 is used, x goes into t2 if the 10th nucleotide in that sequence is either A or C, otherwise, x goes into t3. If x goes into t2, then from the definition of Split 2, it is determined whether x goes into t4 or t5, and so on. When x finally moves into a terminal node, its predicted class is given by the class label attached to that terminal node.

EXAMPLES

*Mycobacterium tuberculosis* rpoB chip

A high density oligonucleotide array (Mtb rpoB chip) has been synthesized and tested in preliminary experiments. The chip has been synthesized using 2 lengths of oligonucleotides (18 and 20 mers) with the interrogation position located at bases 9 and 10 (sense and antisense probes) and 10 and 11 (sense and antisense probes). The Mtb rpoB chip was used initially to genotype 15 *M. tuberculosis* clinical isolates which were previously determined to be RIF sensitive. Oligonucleotide primer sequences, PCR amplification, in vitro transcription and hybridization to the chip conditions were as follows.

Chromosomal DNA from *M. tuberculosis* was isolated by suspending on colony in 100 $\mu$l of ddH$_2$O, boiling for 10 minutes and briefly centrifuging to separate the DNA solution from cellular debris. The chromosome DNA was then diluted 1:10 in ddH$_2$O. A 705 bp rpoB fragment was amplified in a 100 $\mu$l reaction volume containing each dNTP at 200 µM, each primer at 0.2 µM, 2.5 U of Taq-polymerase (BM, Indianapolis, Ind.), 10 mM Tris (pH 8.3), 50 mM KCl, 1.5 mM MgCl₂. The amplification was carried out in a model 9600 thermocycler (Perkin Elmer Cetus). To amplify the 705 bp fragment using primers rpoB-4 (CTC GGA ATT AAC CCT CAC TAA AGG GAC CCA GGA CGT GGA GGC GAT CAC ACC GCA) (SEQ ID NO:1) and rpoB-7 (TAA TAC GAC TCA CTA TAG GGA GAC GTC GCC GCG TCG ATC GCC GCG C) (SEQ ID NO:2) with incorporated T3 and T7 sequences 5 min 95° C., 35 cycles of 1 min 95° C., 30 sec 68° C. and 2 min at 72°, followed by 10 min of 72° were used. The PCR amplicon was then purified using Amicon Microcon 100 columns. In vitro transcription of approximately 50 ng amplicon was performed in a reaction volume of 20 µl, containing 1.25 mM rNTPs, 10 mM DTT, 125 µm F-CTP, 20 U RNase inhibitor, 40 mM Tris-HCl (pH 7.5), 6 mM MgCl₂, 2 mM spermidine, 10 mM NaCl, 20 U T3/T7 RNA-polymerase for 90 min at 37° C. The RNA was then purified with Amicon Microcon 100 columns and quantitated using a spectrophotometer. Fragmentation was carried out in 30 mM MgCl₂ at 95° C. for 30 min. A 20 nM RNA solution in 6×SSPE, 20% formamide, 0.005% Triton, 0.5 nM control oligo was heated to 68° C. for 10 min, then placed on ice for 5 min and hybridized to the Mtb rpoB chip for 30 min at 22° C. in the Affymetrix Fluidics Station. The post-hybridization wash was performed with 1×SSPE, 20% formamide, 0.005% Triton x 100 in the Affymetrix Fluidics Station (Affymetrix, Santa Clara, Calif.), using 12 wash cycles with 2 fills and drains per cycle, followed by a wash with 6×SSPE, 0.005% Triton, 2 cycles with 2 fills and drains per cycle. The chip was then scanned on a Molecular Dynamics scanner (Molecular Dynamics, Santa Clara, Calif.) at 22° C. with a resolution of 11.25 pixels/µm.

As noted, 20% formamide was used in both hybridization and post-hybridization wash steps since the 700 bp amplicon is 67.7% G:C rich with a 18 bp region which is 73.3% G:C rich. The results from the analysis by the Mtb rpoB chip indicated that there were on polymorphisms at any base of the 700 bp for any of the 15 M. tuberculosis RIF sensitive isolates analyzed. This result was confirmed by conventional dideoxynucleotide sequencing. Thus, both methods were 100% concordant in the analysis of 10,500 nucleotides of total sequence.

Detection of Mutations Conferring RIF Resistance

Four pre-resistant/post-resistant RIF isolates were screened in a blinded fashion. These were analyzed using this first generation Mtb rpoB chip. Table 2 summarizes the results of the chip analysis. Of the 4 pair isolates, three pair were observed to have one member of the pair which possessed mutations in the 81 bp region (all other nucleotides were wild type), with the companion isolates displaying no such mutations. Interestingly, the fourth pair (001415/001417) contained no mutation at any nucleotide of the 700 bp surveyed, although isolate 001417 was characterized as RIF resistant by culture assay. Since 10% of RIF resistant M. tuberculosis isolates have no mutation in the 81 bp region of rpoB, this isolate may be resistant because of a mutation in the portion of rpoB not analyzed by the chip or because of a mutation in some other gene which controls uptake, metabolism or drug binding. The sequences derived using the chip for all 8 isolates were confirmed using dideoxynucleotide sequencing. An additional 4 RIF resistant isolates were also screened. Mutations only within the 81 bp region were detected for each of these isolates by the Mtb rpoB chip and confirmed by dideoxynucleotide sequencing. A total of 25 M. tuberculosis isolates were analyzed. Seven of these were rifampicin resistant and had the mutations shown in Table 2. Other than the mutations shown in Table 2, there were no polymorphisms in any of the 25 isolates.

TABLE 2

RIF Sensitive and Resistant M. tuberculosis Clinical Samples Analyzed by Mtb rpoB Chip and Confirmed by Did

| Sample | Amino Acid[1] | Nucleotide[1] | Phenotypic Resistance[1] |
| --- | --- | --- | --- |
| M0404A | None | None | No |
| 000936 | S456L | TCG->TTG | Yes |
| 00145 | None | None | No |
| 001417 | None | None | Yes |
| 000914 | None | None | No |
| 001231 | S456L | TCG->TTG | Yes |
| 001587 | H451D | CAC->GAC | Yes |
| SM2341 | None | None | No |
| 3407 | H451Y | CAC->TAC | Yes |
| 978 | H451L | CAC->CTC | Yes |
| 3553 | S456L | TCG->TTG | Yes |
| 3466 | S447L | TCG->TTG | Yes |

[1] Amino acid and nucleotide numbering system employs sequencing derived by Miller, et. al. (1993).
[2] Resistance was determined using relative/proportion method of Small et al., "Tuberculosis: Pathogenesis, Protection, and Control" pp. 569–586 (1994) (Am. Soc. Microbiol., ed. B. R. Bloom)

Figure 12:
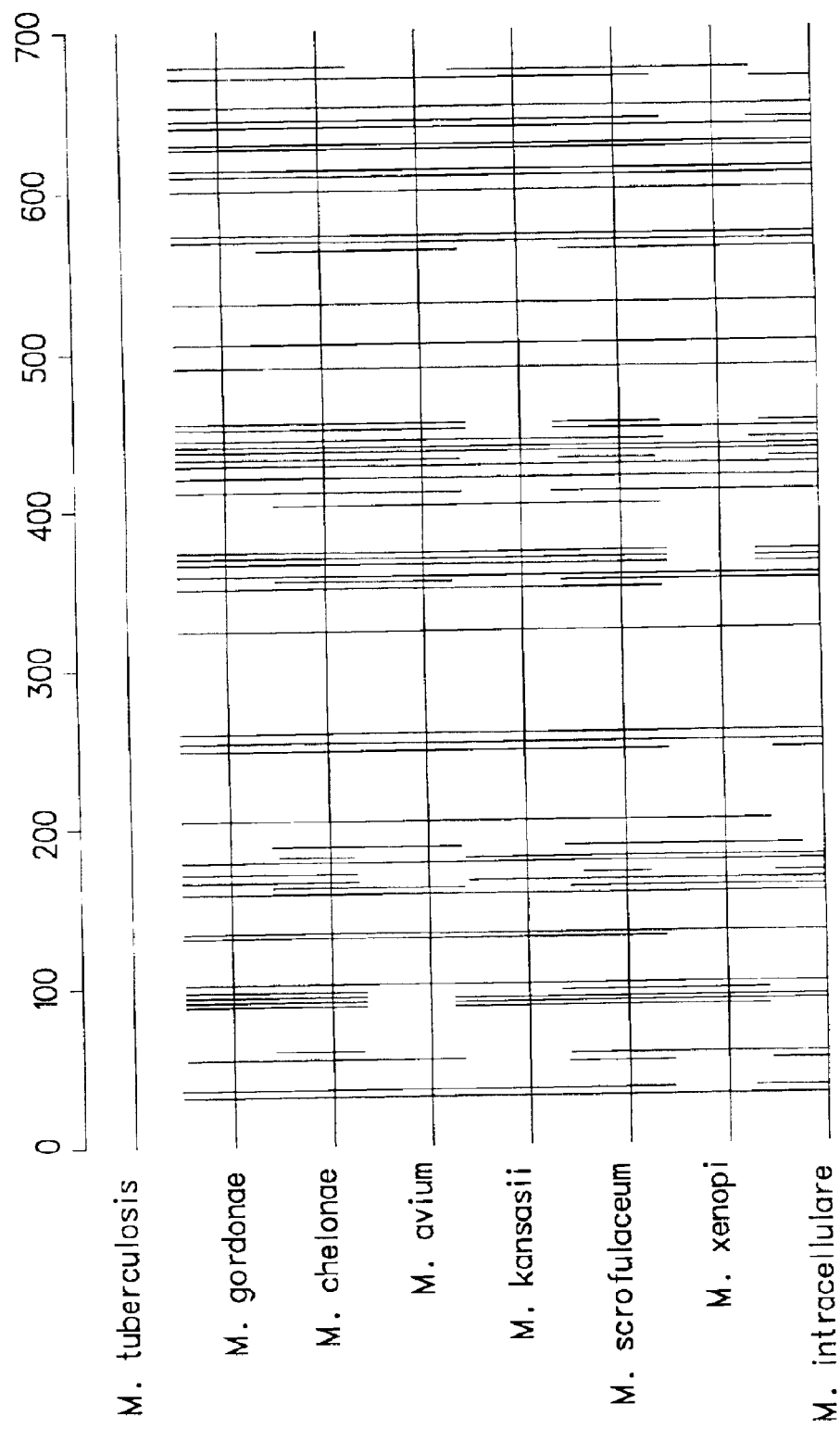
FIG. 12: Shared single nucleotide polymorphisms of seven *Mycobacterium* species.
Figure 13:
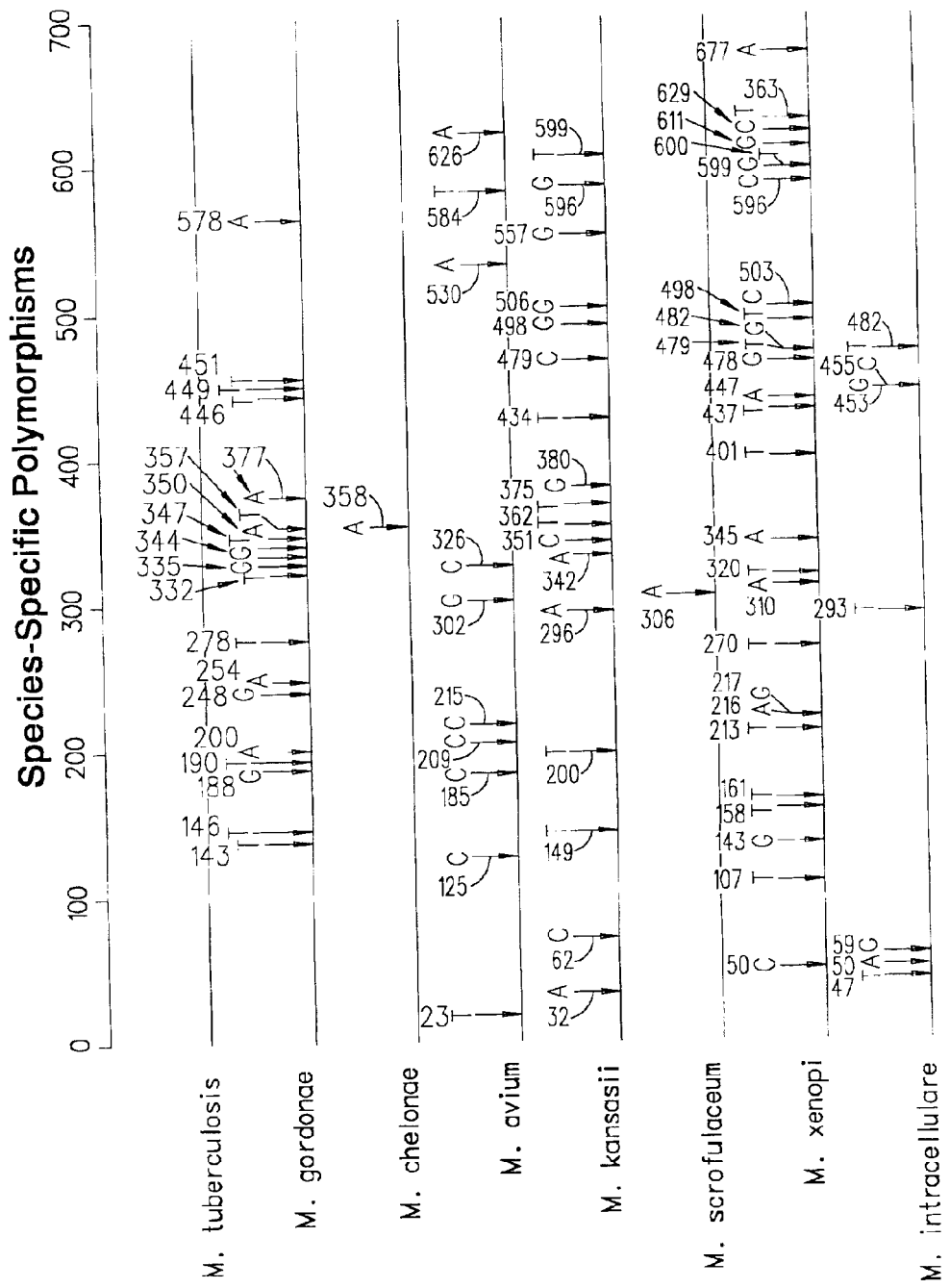
FIG. 13: Unique (species-specific) single nucleotide polymorphisms of seven *Mycobacterium* species.
Figure 14B:
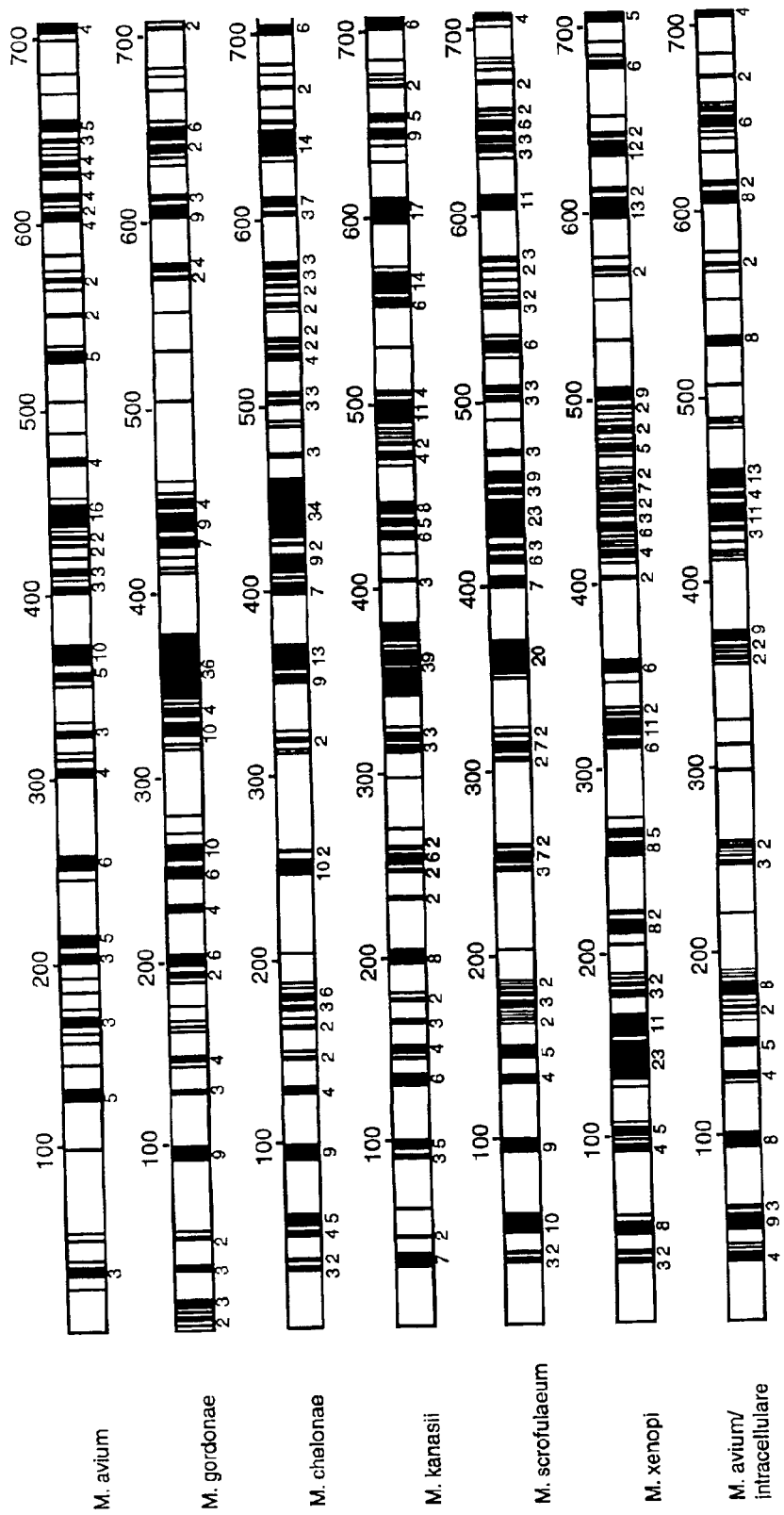

Single Nucleotide Polymorphisms and Hybridization Pattern (Fingerprint) Database for Non-Tuberculosis Mycobacteria The first steps in assembling a database (consisting of SNPs and chip based hybridization fingerprints) capable of identifying mycobacteria species were taken with the analysis of 7 clinically important Mycobacteria species: M. gordonae, M. chelonae, M. kansasii, M, scrofulaceum, M. avium, M. intracellulare and M. xenopi. As a first step, the 700 bp region of the rpoB gene from one isolate from each of these species was sequenced using dideoxynucleotide methodology. Nucleotide (60–71) and amino acid (5–8) differences were compared to M. tuberculosis within the 700 bp region for each of these mycobacteria species (Table 3). Two types of single nucleotide polymorphisms (SNP) were noted: species specific (unique) and shared. The SNPs which were shared with at least 3 other non-tuberculosis mycobacteria are numerous and scattered throughout the 700 bps analyzed. FIG. 12 illustrates the location of these shared SNPs. The species specific SNPs are, however, considerably fewer. FIG. 13 depicts the location and nature of the SNPs for each of the 7 species analyzed based on one isolate for each species.

TABLE 3

Comparison of Polymorphisms in Mycobacteria Species
Number of polymorphic

| | Nucleotides | | AA - changes | |
| --- | --- | --- | --- | --- |
| Strain | Total | Unique | Total | Unique |
| M. gordonae | 71 | 19 | 5 | 1 |
| M. chelonae | 62 | 1 | 5 | 1 |
| M. avium | 60 | 10 | 5 | 0 |
| M. kansasii | 67 | 17 | 6 | 4 |
| M. scrofulaceum | 63 | 1 | 6 | 1 |
| M. xenopi | 72 | 27 | 8 | 7 |
| M. intracellulare | 60 | 7 | 6 | 2 |

When fluorescently-labeled RNA amplicons from each of the 7 mycobacteria species were hybridized to the Mtb rpoB chip, the image of the hybridization is considerably different then when an amplicon for M. tuberculosis was hybridized (FIG. 15A). The differences in the hybridization patterns can be represented as a bar-code-like fingerprint (FIG. 15B). Each line on the fingerprint represents a hybridization difference as compared to when wild type M. tuberculosis is hybridized. These differences are attributable to the species specific and shared polymorphisms identified by the dideoxynucleotide sequencing analysis (Table 3). For any individual *Mycobacteria* species, only some of the different depicted by an individual line of the fingerprint is identifiable as a specific base pair difference. The remainder of the lines of the fingerprint can be characterized only as being different than if a *M. tuberculosis* sample was hybridized. These undefined differences are usually caused when multiple polymorphisms occur in close proximity or they are the result of the destabilization of the hybridization of neighboring probes due to the presence of unique or shared polymorphisms. In such clustered polymorphism cases, there are multiple mismatches within individual probes interrogating nucleotides in a region. Hybridization results involving such probes are unstable leading to ambiguous, wrong or no calls. Thus, a full fingerprint pattern is composed of identified (unique or shared polymorphisms) and unidentified (clustered polymorphisms leading to no base calling determination) differences. An average of 27.7% of the 700 bps interrogated are viewed as different than if a *M. tuberculosis* target were hybridized to the chip (Table 4). In other words, for every base identified by ABI sequencing as being polymorphic, the chip sees three bases as different from Mtb. This is due to, in addition, each of the two bases flanking the base identified by ABI as polymorphic also being viewed as different by the chip, because of destabilization of hybridization at these sites.

analyzed by the Mtb rpoB chip. FIG. 15 presents the images of the sense strand hybridization. Below each chip image is the hybridization fingerprint computed after analysis of both strands. The shared differences among the 11 (10 new and 1 original) isolates analyzed are shown below (Table 5). From this analysis a core (consensus) fingerprint pattern for *M. gordonae* was derived (FIG. 15). A similar core fingerprint has been derived for eight other *Mycobacterium* species, thus allowing identification of those species. It will be apparent that the techniques described above can be used to assemble a database of species-specific and shared polymorphisms which can be used to derive fingerprints for other species.

It is important to note that as the total number of analyzed isolates for each species is increased, it is unlikely that a single and unique core fingerprint will define a *Mycobacterium* species. Rather, it is expected that any particular isolate of a *Mycobacterium* species will have a subset of all possible fingerprints. Identification of the *Mycobacterium* species based on a fingerprint pattern will require a classification analysis, as described earlier, using the tree-based classification algorithms built upon a collected database consisting of species specific and shared SNPs and fingerprints.

TABLE 5

Percent Shared Differences Among Gordonae Clinicals

|  | golz | gord | gordjd | gord1b | gordig | gordil | gordmb | gordow | gordrb | gordwn | gorm |
|---|---|---|---|---|---|---|---|---|---|---|---|
| golz | 0 | | | | | | | | | | |
| gord | 18.7 | 0 | | | | | | | | | |
| gordjd | 16.7 | 17.4 | 0 | | | | | | | | |
| gord1b | 19.3 | 22.7 | 18.3 | 0 | | | | | | | |
| gordig | 23.7 | 18.7 | 17.3 | 19.6 | 0 | | | | | | |
| gordil | 18.3 | 14.6 | 15.2 | 15.5 | 17.9 | 0 | | | | | |
| gordmb | 19.7 | 22.4 | 18.4 | 24.3 | 19.7 | 15.3 | 0 | | | | |
| gordow | 19.6 | 16.3 | 16.6 | 17.0 | 19.6 | 18.7 | 16.7 | 0 | | | |
| gordrb | 20.6 | 23.3 | 18.9 | 24.5 | 20.6 | 16.2 | 25.0 | 18.4 | 0 | | |
| gordwn | 17.6 | 17.4 | 16.9 | 17.9 | 16.9 | 15.2 | 18.0 | 16.2 | 19.0 | 0 | |
| gorm | 20.1 | 22.7 | 19.1 | 24.0 | 20.9 | 16.2 | 24.3 | 17.6 | 25.0 | 18.2 | 0 |

TABLE 4

Differences of Fingerprint Patterns Among
*Mycobacteria* Species Compared to *M. tuberculosis*

|  | Nucleotide Differences[1.] | % Differences[2.] |
|---|---|---|
| *M. gordonae* | 188 | 26.7 |
| *M. chelonae* | 208 | 29.5 |
| *M. avium* | 152 | 21.5 |
| *M. kansasii* | 216 | 30.6 |
| *M. scrofulaceum* | 213 | 30.2 |
| *M. xenopi* | 229 | 32.4 |
| *M. intracellulare* | 164 | 23.2 |

[1.]The nucleotide differences are composed of identified differences compared to the *M. tuberculosis* sequence (species specific and shared polymorphisms) and unidentified differences (caused by clustered polymorphisms).
[2.]% differences are based on a total of 700 bp analyzed by Mtb rpoB gene on the chip.

Since the database for each of the non-tuberculosis mycobacteria was the result of analysis of only a single isolate for each *Mycobacteria* species, the variation of fingerprint patterns that would be observed among multiple isolates of a single *Mycobacteria* species was explored. Consequently, the rpoB gene from 10 isolates of *M. gordonae* were Human Mitochondrial DNA Chip (MT1)

Fluorescein labelled target RNA was synthesized and fragmented, and the transcription mixture diluted 20-fold in 6×SSPE, 0.05% Triton X-100, to give approximately 1 to 10 nMRNA (estimated prior to fragmentation). Hybridization was carried out for 30 min at RT. The chip was washed for a total of 5 to 10 minutes in several changes of 6×SSPE, 0.005% Triton X-100, and scanned.

FIG. 22A shows the design of the tiled array on the MTI chip. Each position in the target sequence (upper case) is interrogated by a set of 4 probes on the chip (lower case), identical except at a single position, termed the interrogation base, which is either A, C, G, or T. The target will be perfectly complementary to one of the 4 probes, but mismatched with the others. As illustrated in FIG. 10, the perfect complement gives a more intense hybridization signal than do the mismatches. Each of the lower three probes represents a 4 probe set, with n=A, C, G, or T. By tiling the sets across the sequence in single base increments as shown, a nucleic acid target of length N can be scanned for mutations with a tiled array containing 4N probes. (B) Hybridization to a tiled array and detection of a point mutation. The array shown was designed to the MT1 target sequence. When hybridized to MTI (upper panel), one probe in each set of 4 in a column is perfectly matched to the target, while the other three contain a single base mismatch. The interrogation base used in each row of probes is indicated on the left of the image. The target sequence can be read 5' to 3' from left to right as the complement of the interrogation base with the brightest signal. Hybridization to MT2 (lower panel), which differs from MT1 in this region by a T→C transition, affects the probe sets differently. At the location of the polymorphism, the G probe is now a perfect match to MT2, with the other three probes having single base mismatches. (A*, C*, G*, T* counts). However, at flanking positions, the probes have either single or double base mismatches, since the MT2 substitution now occurs away from the interrogation position. The location of the mismatch is illustrated in the probe schematic by red circles.

Detection of Base Differences of Base Differences Between a Sample and Reference Sequence in 2.5 kb by Comparison of Scaled $p^{020,9}$ Hybridization Intensity Patterns Between a Sample and a Reference Target In this study, each 2.5 kb target sequence was PCR amplified directly from genomic DNA using the primer pair L14675-T3 (5'aattaaccctcactaaagggATTCTCGCACGGACTACAAC) (SEQ ID NO:7) and H667-T7, transcribed to give RNA targets labelled with fluorescein or biotin, pooled and fragmented as described. In the experiments shown the MT1 reference target was biotin labelled and the sample target fluorescein labelled. Targets were diluted 180 fold from the transcription reaction to a final concentration of –100 to 1000 pM in 3 M TMAC1, 10 MM Tris.Cl pH 8.0, 1 mM EDTA, 0.005% Triton X-100, and 0.2 nM of a control oligonucleotide, 51 fluorescein-CTGAACGGTAGCATCTTGAC (SEQ ID NO:8) (We found that the G-rich H strand target hybridized poorly in 1 M NaCl, but hybridized well in 3 M tetramethyl ammonium chloride, whereas the L strand hybridized well in either solution). Hybridization was carried out in packaged chips. Samples were denatured at 95° C. for 5 min. chilled on ice for 5 min. and equilibrated to 37° C. A volume of 180 gl of hybridization solution was then added to the flow cell and the chip incubated at 37° C. for 3 h with rotation at 60 rpm on a laboratory rotisserie. Following hybridization, the chip was washed 6 times at RT with 6×SSPE, 0.005% Triton X-100. A solution of 2 gg/ml phycoerythrin-conjugated streptavidin in 6×SSPE, 0.005% Triton X-100, was added, and incubation continued at RT for 5 min. The chip was washed again, and scanned at a resolution of –74 pixels per probe cell. Two scans were collected, one using a 530 DF 25 nm bandpass filter, and the second using a 560 nm longpass filter. Signals were deconvoluted to remove spectral overlap and average counts per cell determined. The sample probe intensities were scaled to the reference intensities as follows: a histogram of the base-10 logarithm of the intensity ratios for each pair of probes was constructed. The histogram had a mesh size of 0.01, and was smoothed by replacing the value at each point with the average number of counts over a five-point window centered at that point. The highest value in the histogram was located, and the resulting intensity ratio was taken to be the most probable calibration coefficient.

The data are shown in FIG. 24 for L strand targets hybridized to H strand probes, from a portion of hypervariable region I in the mitochondrial control region. Numbering is conventional. In each plot, the reference target intensities are shown in red and the sample in blue. The reference, MT1, is a perfect match to the $p^0$ probes. FIG. 24A—Comparison of iefOO7 to MT1. There is a single base difference between the two target sequences, located at position 16,223 (MT1 C: iefOO7 T). This results in a "footprint" spanning—20 positions, 11 to the left and 8 to the right of position 16,223, in which the iefOO7 $p^0$ intensities are decreased by a factor of more than 10 fold relative to the MT1 intensities. The size and location of the footprint are consistent with a single base mismatch affecting hybridization to $p^{20,9}$ probes. The theoretical footprint location is indicated by the grey bar, and the location of the polymorphism is shown by a vertical black line within the bar. The size of a footprint changes with probe length, and its relative position with interrogation position (not shown). Because the sample and reference targets are in competition, the MT1 signal in a footprint region actually increases as a proportion of total signal in each probe cell, because the mismatched sample target no longer competes effectively for probe sites. FIG. 24B—Comparison of haOO1 to MT1. The haOO1 target has 4 polymorphisms relative to MT1. The $p^0$ intensity pattern clearly shows two regions of difference between the targets. Furthermore, it can easily be seen that each region contains ≧2 differences, because in both cases the footprints are longer than 20 positions, and therefore are too extensive to be explained by a single base difference. The effect of competition can be seen by comparing the MT1 intensities in the iefOO7 and haOO1 experiments: the relative intensities of MT1 are greater in panel B where haOO1 contains po mismatches but iefOO7 does not. FIG. 24C—The haOO4 sample has multiple differences to MT1, resulting in a complex pattern extending over most of the region shown. Thus, differences are clearly detected, even though basecalling might be compromised using only the 4N tiling array. Even when patterns are highly complex, samples can be compared and matched. For example, if the haOO4 sample is compared to haOO4 as a reference in the same experiment, the $p^0$ pattern indicates a match, even though the effect of multiple mismatches might compromise direct sequence reading (not shown).

Detection of a 2 bp-Deletion

Figure 26:
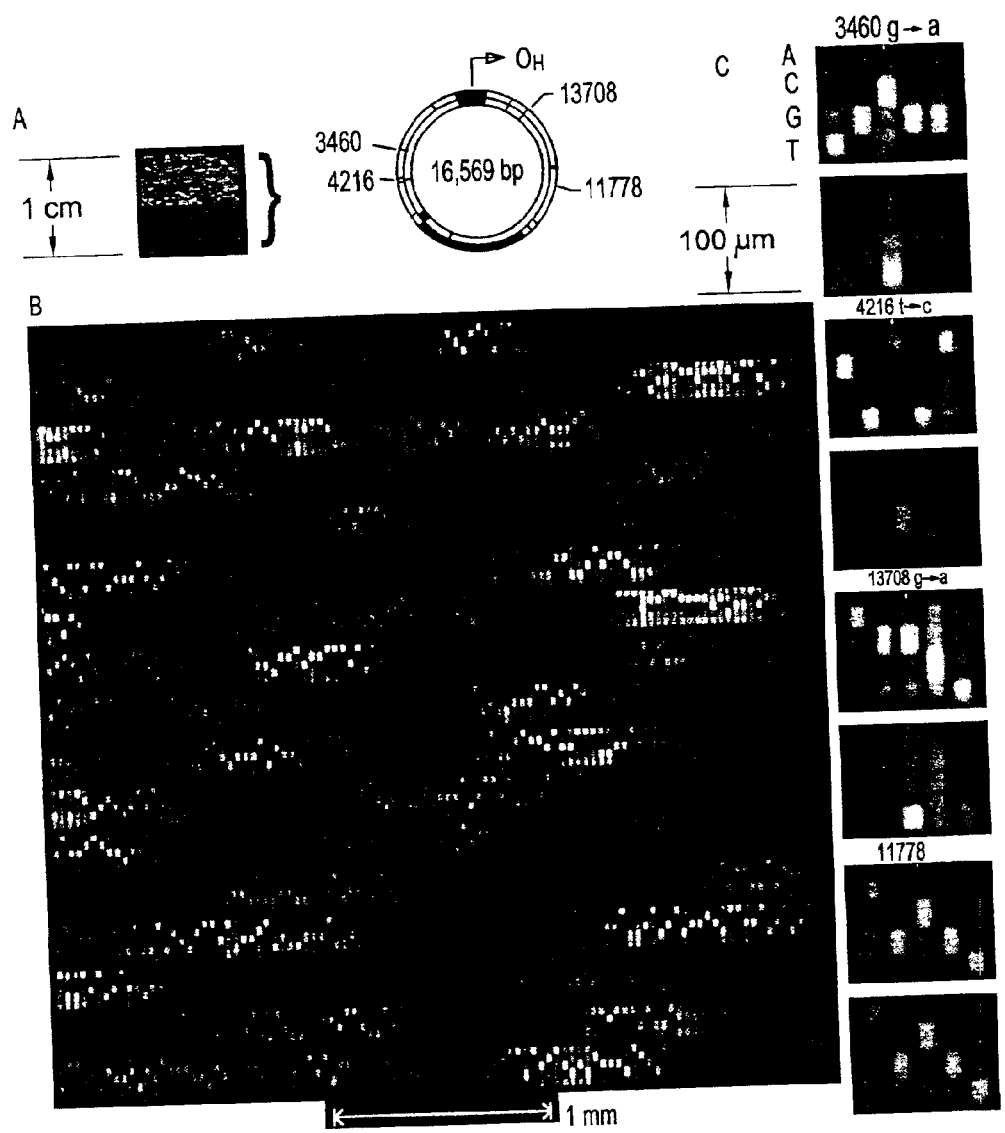

Experimental details are as above. The results are shown in FIG. 26. FIG. 25A shows that although the 4N array was not designed to detect length polymorphisms, this common 2 bp length polymorphism located at 514–523 in the MT DNA was easily detected by the presence of a po intensity footprint. FIG. 24B shows target-specific effects on hybridization. A 2 bp difference between the MT1 reference (GG) and the haOO2 target (AA) is associated with a complex footprint pattern: the po signals of the mismatched haOO2 hybrids are up to 10-fold higher than those of the perfectly attached mt1 hybrids in a region extending leftwards from position 16,381. Both samples were hybridized simultaneously to the same array. In addition, the effect extends beyond the probes directly affected by the mismatches. Therefore, we conclude that the difference is due to changes in target secondary structure. Increased accessibility of the target as a result of disruption of base pairing between inverted repeats (shaded on the diagram) could explain the increase in the sample versus the reference $p^0$ signals.

Hybridization of a 16.3 kb of Mitochondrial Target Sequence to the Whole Genome Chip FIG. 26A shows an image of the array, actual size hybridized to L strand target sample. The 1.28×1.28 cm, $p^{20,9}$ tiled array contains a total of 134,688 probes, each synthesized in a 35×35 micron cell. The number of probes is sufficient to represent the 16.6 kb genome twice over. The array has the capacity for sense and antisense coding. The 16,569 bp map of the genome is shown and the H strand origin of replication (OH)' located in the control region, is indicated. FIG. 26B—A portion of the hybridization pattern is shown, magnified. The scale is indicated by the bar on the left hand side. Most of the array can be read directly. The image, which was generated by the galvanometer scanner detection system in under 2 minutes, was collected at –3 micron, 16 bit pixel resolution, providing ~100 pixels of intensity data for each probe cell in the array. Fluorescence was detected through a 581 Df 52 nm. bandpass filter. FIG. 26C—The ability of the array to detect and read single base differences in a 16.3 kb sample is illustrated. Two different target sequences were hybridized in parallel to different chips. The hybridization patterns are compared for four different positions in the sequence. The top panel of each pair shows the hybridization of a the MT3 target, which matches the chip po sequence at these positions. The lower panel shows the pattern generated by a sample from a patient with Leber's Hereditary Optic Neuropathy (LHON). Three pathogenic mutations are implicated, LHON3460, LHON4216, and LHON13708. All three are clearly detected. For comparison, the third panel in the set shows a region that is identical in both samples, around position 11,778.

The pattern matching techniques described above also provide a method of determining whether the nucleic acid sequence of a biological sample is homozygous or heterozygous for a particular allele, i.e., to identify the presence of a polymorphism in the nucleic acid sequence at a particular position. In this regard, polymorphisms can be identified in both coding and noncoding sections of the sample nucleic acid, i.e., in exons or introns. This is of value, for example, in identifying whether a genetically linked disease is present. Of course, it will be recognized that any genetically related condition, i.e., other than those thought as "disease" can be identified by such a method.

FIG. 33 shows a computer-implemented flowchart of a method of identifying the presence of a polymorphism in a nucleic acid sequence from a patient sample. The flowcharts described herein are for illustration purposes and not limitation. For example, for simplicity FIG. 33 describes analyzing one base position at a time to detect polymorphisms. However, each step may also be performed for the entire nucleic acid sequences and/or some steps may be combined.

At step 200, the system selects a base position in the nucleic acid sequence from the patient sample. The system determines the difference between the hybridization intensities of the nucleic acid sequence from the patient sample and a corresponding nucleic acid sequence from a wild type sample to an array of reference nucleic acid probes at step 202. Although the reference nucleic acid probes may perfectly complementary to the wild type sample, this is not required.

The system derives or calculates a ratio of the difference determined at step 202 to the hybridization intensity of the nucleic acid sequence from the wild type sample. The ratio is derived at step 204 and it indicates how close the hybridization intensities for the nucleic acid sequences from the patient wild type samples are to being the same.

An assigned value is utilized to determine if the ratio indicates that there is a polymorphism at the base position. The assigned value may be user specified and at step 206, the system compares the ratio to the assigned value. If the ratio is greater than the assigned value, the system identifies the presence of a polymorphism at the base position of the nucleic acid sequence from the patient sample. At step 210, the system determines if there is a next base position to analyze.

By way of example and not limitation, one can screen nucleic acid samples from a cancer patient to determine whether the DNA repair genes MSH or MLHI are mutated. This is done by comparing the hybridization pattern of patient DNA from the appropriate region to the hybridization pattern of DNA from the same region of a healthy (i.e., wild-type) sample. FIGS. 27–30 show such comparisons of patient DNA samples from heterozygous MSH2, MLH1, MSH2 and p53 genes and their corresponding wild type genes. The screening can be against any reference sequence immobilized on the chip, though as described earlier it will be advantageous to use a chip in which the reference sequence is complementary to the wild type sequence. The hybridization intensities corresponding to each base position is determined for each sample as described earlier. One then determines the difference between the intensities for the patient sample and the wild type sample at each base position and compares that to the wild type intensity at that base position. This ratio can vary between one and zero, being zero if the wild type and patient sequences are identical in this region (since hybridization will be identical for both samples) and approaching one if there is a complete mismatch, i.e., no hybridization at all between patient sample and the reference sequence in that region. If this ratio is greater than an assigned value, it indicates a polymorphism at that particular base position. Typically, this assigned value is set at about 0.5, preferably 0.6. Positions at which such polymorphisms are present can be identified by plotting this ratio versus the corresponding base position for all positions where the ratio is greater than about 0.25. If the ratio is less than 0.25, this is considered to be statistical noise. Typically such plots will show a spike, with a maximum ratio of about 0.5, centered approximately around the site of the polymorphism. The plots are made with variables derived as follows:

Y axis: y=(WT intensity−PS intensity)/WT intensity

X axis: x=base position where WT=wild type and PS=patient sample

The technique has been refined further to provide a higher level of accuracy by determining hybridization intensities from both the sense and antisense strands of the DNA sample and requiring that the spike occur in both strands at the same respective complementary positions. The probes on the chip are typically 10–20 mers and therefore create a "footprint" as one tiles through the position where the polymorphism is present, i.e., there will be a difference between the hybridization intensities of the patient sequence and the wild type sequence in this region. As a result, an even higher level of confidence that a polymorphism occurs at a particular base position is obtained by requiring that the hybridization intensity ratio derived above be greater than the assigned value, 0.5 in this example, for at least two adjacent base positions, preferably three adjacent positions.

Mismatch Detection by Tiled Arrays

In this example, a reference target T0 and three mutant targets T1, T2, and T3 are provided. T1 has a substitution at position 11, T2 at position 9, and T3 at positions 9 and 11. In writing the mutant sequences, the position of the substitution is noted by S. These sequences are depicted in Table 6.

TABLE 6

Substitutions in Mutant Sequences

| T0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| T1 |   |   |   |   |   |   |   |   |   |    | S  |    |    |    |    |    |    |    |    |    |    |
| T2 |   |   |   |   |   |   |   |   |   | S  |    |    |    |    |    |    |    |    |    |    |    |
| T3 |   |   |   |   |   |   |   |   |   | S  | S  |    |    |    |    |    |    |    |    |    |    |

Each of these targets is hybridized with a DNA chip containing a tiled arrays of probes. For simplicity, a $p^7{}_4$ chip is described herein. The superscript 7 indicates that the chip contains a tiled array of 7-mer probes that are perfectly or partially complementary to the reference target. The subscript 4 denotes the interrogation position, such that the nucleotide at position 4 of each 7-mer is varied (A, T, G, or C in four different synthesis cells).

The number of target-probe mismatches is given in Table 7 below. The top row gives the number of mismatches for the best-match case (i.e., for the most complementary probe of each set of four) and the second row gives the number of mismatches for the other three probes in the set.

TABLE 7

Target Probe Mismatched

| T0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| versus | 0 | 0 | 0 | 0 | 0 | 0 | 0 | 0 | 0 | 0 | 0 | 0 | 0 | 0 | 0 | 0 | 0 | 0 | 0 | 0 | 0 |
| T0 | 1 | 1 | 1 | 1 | 1 | 1 | 1 | 1 | 1 | 1 | 1 | 1 | 1 | 1 | 1 | 1 | 1 | 1 | 1 | 1 | 1 |
| versus | 0 | 0 | 0 | 0 | 0 | 0 | 0 | 1 | 1 | 1 | 0 | 1 | 1 | 1 | 0 | 0 | 0 | 0 | 0 | 0 | 0 |
| T1 | 1 | 1 | 1 | 1 | 1 | 1 | 1 | 2 | 2 | 2 | 1 | 2 | 2 | 2 | 1 | 1 | 1 | 1 | 1 | 1 | 1 |
| versus | 0 | 0 | 0 | 0 | 1 | 1 | 1 | 0 | 1 | 1 | 1 | 0 | 0 | 0 | 0 | 0 | 0 | 0 | 0 | 0 | 0 |
| T2 | 1 | 1 | 1 | 1 | 2 | 2 | 2 | 1 | 2 | 2 | 2 | 1 | 1 | 1 | 1 | 1 | 1 | 1 | 1 | 1 | 1 |
| versus | 0 | 0 | 0 | 0 | 1 | 1 | 1 | 1 | 2 | 2 | 1 | 1 | 1 | 1 | 0 | 0 | 0 | 0 | 0 | 0 | 0 |
| T3 | 1 | 1 | 1 | 1 | 2 | 2 | 2 | 2 | 3 | 3 | 2 | 2 | 2 | 2 | 1 | 1 | 1 | 1 | 1 | 1 | 1 |

Shown below in Table 8 are the number of mismatches in the best-match case for the hybridization of $p^7{}_4$ with a series of targets containing two substitutions at different separations:

TABLE 8

Best Match Hybridization

| T0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
|   |   |   |   |   |   |   |   | S | S |    |    |    |    |    |    |    |    |    |    |    |    |
|   |   |   |   |   | 1 | 2 | 2 | 1 | 1 | 2  | 2  | 1  |    |    |    |    |    |    |    |    |    |
|   |   |   |   |   |   |   |   | S |   | S  |    |    |    |    |    |    |    |    |    |    |    |
|   |   |   |   |   | 1 | 1 | 2 | 1 | 2 | 1  | 2  | 1  | 1  |    |    |    |    |    |    |    |    |
|   |   |   |   |   |   |   |   | S |   |    | S  |    |    |    |    |    |    |    |    |    |    |
|   |   |   |   |   | 1 | 1 | 1 | 1 | 2 | 2  | 1  | 1  | 1  | 1  |    |    |    |    |    |    |    |
|   |   |   |   |   |   |   |   | S |   |    |    | S  |    |    |    |    |    |    |    |    |    |
|   |   |   |   |   | 1 | 1 | 1 | 0 | 2 | 2  | 2  | 0  | 1  | 1  | 1  |    |    |    |    |    |    |
|   |   |   |   |   |   |   |   | S |   |    |    |    | S  |    |    |    |    |    |    |    |    |
|   |   |   |   |   | 1 | 1 | 1 | 0 | 1 | 2  | 2  | 1  | 0  | 1  | 1  | 1  |    |    |    |    |    |
|   |   |   |   |   |   |   |   | S |   |    |    |    |    | S  |    |    |    |    |    |    |    |
|   |   |   |   |   | 1 | 1 | 1 | 0 | 1 | 1  | 2  | 1  | 1  | 0  | 1  | 1  | 1  |    |    |    |    |

When a target is hybridized to a 7-mer chip $P^7$ containing the tiled reference sequence, the number of mismatches in this case is the same as that given by the best-match case above except for an additional mismatch at each substitution position (See Table 9). For T3, for example, $P^7$ has one more mismatch at positions 8 and 11, where T3 has substitutions, than does $P^7{}_4$.

TABLE 9

Mismatches at Substitution Position

| $P^7$ |   |   |   |   |   |   |   | S |   |   | S |   |   |   |   |   |   |   |   |   |   |
|---|---|---|---|---|---|---|---|---|---|---|---|---|---|---|---|---|---|---|---|---|---|
| versus | 0 | 0 | 0 | 0 | 1 | 1 | 1 | 2 | 2 | 2 | 2 | 1 | 1 | 1 | 0 | 0 | 0 | 0 | 0 | 0 | 0 |
| T3 |   |   |   |   |   |   |   |   |   |   |   |   |   |   |   |   |   |   |   |   |   |

Thus, to generalize, for a $P^n_j$ chip, and a target containing a substitution at position a, the best-match set of probes will contain 1 mismatch from a−1 to a−k, 0 at a, and 1 mismatch from a+1 to a+m, where k=j−1 and m=m−j. For $P^7_4$, k=3 and m=3, and so the 1 mismatch zone is from a−1 to a−3, and from a+1 to a+3, with no mismatch at a, the interrogation position.

The effects of multiple substitutions are additive. Thus, for example, using a $P^{16}_{10}$ chip and a target containing substitutions at positions a and b, where k is 9 and m is 6, the effect of the substitution at a is to give 1 mismatch from a−1 to a−9, and from a+1 to a+6. The substitution at b will give 1 mismatch from b−1 to b−9, and from b+1 to b+6. If a and b are at positions 100 and 108, their effect is the sum, as shown in Table 10.

TABLE 10

Effects of Multiple Substitutes

| Position | Mismatches |
|---|---|
| 91–98 | 1 |
| 99 | 2 |
| 100 | 1 |
| 101–106 | 2 |
| 107 | 1 |
| 108 | 0 |
| 109–114 | 1 |

Thus, given a hybridization pattern, the location of substitution mutations can be done as follows.

(a) The first step is to hybridize a $P^n_j$ chip with the reference target, and another $P^n_j$ chip with the unknown target. Alternatively, a single $P^n_j$ chip could be hybridized with a mixture of differently labeled reference and unknown targets (e.g., a red-fluorescent reference target and a green-fluorescent unknown target). By using a pair of chips, or a pair of suitably labeled targets, one can readily identify probes that contain mismatches and distinguish between 0, 1, 2 and a larger number of mismatches.

(b) A substitution at location a is identified by the presence of a 1-mismatch zone that is n-residues long except for a 0-mismatch cell at residue a. The probe giving the highest intensity at residue a identifies the substitution.

(c) A "quiet zone" (i.e., where the unknown target exhibits 1 or more mismatches) that is longer than n must contain at least two substitutions (the effects of insertions and deletions are considered below). The differences between $P^n_j$ and $P^n$ reveal the sites of the substitutions. Again, the probe of $P^n_j$ giving the highest intensity at each of these sites identifies the substitution. An example is provided in Table 11 below.

TABLE 11

| | 5 | 6 | 7 | 8 | 9 | 10 | 11 | 12 | 13 | 14 | 15 | 16 |
|---|---|---|---|---|---|---|---|---|---|---|---|---|
| Target | | | | S | | | | | S | | | |
| $P^7$ | 1 | 1 | 1 | 1 | 1 | 2 | 2 | 1 | 1 | 1 | 1 | 1 |
| $P^7_4$ | 1 | 1 | 1 | 0 | 1 | 2 | 2 | 1 | 0 | 1 | 1 | 1 |
| $P^7-P^7_4$ | 0 | 0 | 0 | 1 | 0 | 0 | 0 | 0 | 1 | 0 | 0 | 0 |

$P^7-P^7_4$, the difference between the tiled reference sequence and the best-case match of the tiled array, exhibits 1's at positions 8 and 13 and 0's elsewhere, showing that substitutions have occurred at these two positions. Their identity is established by seeing which of the four nucleotides at these interrogation positions has the highest intensity.

(d) Further information can be obtained by hybridizing a generic chip, such as one containing all 10-mers of DNA, with both the reference target and the unknown target. The difference in hybridization patterns identifies probes that span mutation sites.

Identifying Species Utilizing Generic Probe Arrays

It has been determined that generic high density DNA probe arrays may be utilized to identify species of isolates. By "generic" it is meant that the probe array was not specifically designed to identify species within the genus of interest. For example, a probe array that includes all nucleic acid probes ten nucleotides in length would be a generic probe array. Additionally, a probe array for an entirely different purpose may be utilized as a generic probe array. Thus, a probe array for detecting mutations in HIV may be utilized to identify species in *Mycobacterium*.

Given multiple isolates that one wants to determine the species of each isolate, the isolates are first hybridized with the generic probe array to obtain hybridization intensities as described above. Typically, the hybridization intensities will then be normalized across the isolates. It has been determined that analyzing each hybridization intensity from the experiments may not be computationally feasible, or at least economically feasible. Accordingly, the invention reduces the number of variables to analyze.

In one embodiment, for each probe in the generic probe array, the mean and variance for the hybridization intensities across the isolates is calculated. The probes that demonstrate the most variance are then selected and the corresponding hybridization intensities are utilized to cluster the isolates into species. Thus the invention utilizes the hybridization intensities from probes that have the most varying hybridization intensities. One may first specify a number of probes which one believes could be processed by the equipment available. Then, the invention would select the hybridization intensities from that number of probes which will provide the most discriminating information.

This process may be generally utilized to assign groups to multiple isolates, where the groups are species, subspecies, phenotypes, genotypes, and the like. For illustration purposes, the following will describe an embodiment that identifies the species of isolates.

FIG. 35 shows a computer-implemented flowchart of a method of identifying species to which organisms belong. At step 400, hybridization intensities indicating hybridization affinity between multiple isolates and a generic probe array are input. Optionally, the hybridization intensities are then standardized or normalized at step 402 to reduce the variability between the experiments. For example, the hybridization intensities may be standardized to a common mean and variance by Z-score analysis or normalization.

The system selects hybridization intensities that have the most variance across the isolates at step 404. Determining which hybridization intensities vary the most may be done any number of ways including calculating a mean and variance. As an example, the number of hybridization intensities to analyze may be reduced from 10,000 to 20 which drastically reduces the computational time required to analyze the hybridization intensities.

At step 406, the species of each of the multiple isolates is determined according to the selected hybridization intensities. Clustering algorithms may be utilized to cluster the isolates into species. As an example, Principal Components analysis and Variable Clustering analysis may be utilized. The purpose of clustering is to place the isolates into groups or clusters suggested by the data, not defined a priori, such that isolates in a give cluster tend to be similar and isolates in different clusters tend to be dissimilar. Thus, no a prior classification is required.

Isolates of *Mycobacterium* have been analyzed and FIG. 37 shows a hierarchical clustering of these isolates. The height of the cluster represents the average distance between the clusters.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method for assigning a first organism to a particular group or species, comprising:
   (a) providing an array of oligonucleotides at known locations on a substrate, said array comprising probes complementary to at least one reference DNA or RNA sequence;
   (b) obtaining a first hybridization pattern for said first organism by hybridizing a target nucleic acid sequence from the first organism to the array;
   (c) comparing the first hybridization pattern to a plurality of reference hybridization patterns to identify the reference hybridization pattern that most closely matches the first hybridization pattern, wherein each reference hybridization pattern is from an organism of known group or species, and
   (d) identifying the group or species of the first organism.

2. A method of identifying the presence of a nucleic acid polymorphism in a patient sample, comprising the steps of:
   (a) obtaining a first hybridization pattern for the patient sample by hybridizing a target nucleic acid sequence from the patient sample to an array comprising a plurality of probes that are complementary to at least one nucleic acid reference sequence;
   (b) comparing the first hybridization pattern obtained for said target nucleic acid sequence from the patient sample and a corresponding second hybridization pattern obtained for a target nucleic acid sequence from a wild type sample to identify at least one difference in hybridization intensity of a reference probe between the first and second hybridization patterns;
   (c) deriving a hybridization intensity ratio from the at the least one difference in (b); and
   (d) identifying the presence of a polymorphism at a base position within the reference probe if the ratio in (c) is greater than or equal to an assigned value.

3. The method of claim 2, wherein the nucleic acid reference sequence is a sequence or subsequence of mitochondrial DNA.

4. The method of claim 2, wherein the nucleic acid reference sequence comprises an HIV gene or subsequence thereof.

5. The method of claim 2, wherein the nucleic acid reference sequence comprises a gene associated with a heritable disease or subsequence thereof.

6. The method of claim 5, wherein the heritable disease is cystic fibrosis.

7. The method of claim 2, wherein the nucleic acid sequence is a least a subsequence of p53.

8. The method of claim 2, wherein the nucleic acid sequence is at least a subsequence of MSH.

9. The method of claim 2 wherein the nucleic acid sequence is at least a subsequence of MLH1.

10. The method of claim 2, wherein the nucleic acid sequence is at least a subsequence of BRCA-1.

11. The method of claim 2 wherein the probes of the array are 19, 20, 21, 22, 23, 24, 25 or 30 bases in length and exhibit perfect complementarity to said reference sequence.

12. The method of claim 1 wherein the probes of the array are 19, 20, 21, 22, 23, 24, 25 or 30 bases in length and exhibit perfect complementarity to said reference DNA or RNA sequence.

* * * * *

```
                            SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 1:

TGACATAGGC TGTAG                                                           15

(2) INFORMATION FOR SEQ ID NO: 2:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 2:

TGACATCGGC TGTAG                                                           15

(2) INFORMATION FOR SEQ ID NO: 3:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 3:

TGACATGGGC TGTAG                                                           15

(2) INFORMATION FOR SEQ ID NO: 4:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 4:
```

-continued

```
TGACATTGGC TGTAG                                                    15

(2) INFORMATION FOR SEQ ID NO: 5:

(i) SEQUENCE CHARACTERISTICS:
          (A) LENGTH: 54 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 5:

CTCGGAATTA ACCCTCACTA AAGGGACCCA GGACGTGGAG GCGATCACAC CGCA         54

(2) INFORMATION FOR SEQ ID NO: 6:

(i) SEQUENCE CHARACTERISTICS:
          (A) LENGTH: 46 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 6:

TAATACGACT CACTATAGGG AGACGTCGCC GCGTCGATCG CCGCGC                  46

(2) INFORMATION FOR SEQ ID NO: 7:

(i) SEQUENCE CHARACTERISTICS:
          (A) LENGTH: 40 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 7:

AATTAACCCT CACTAAAGGG ATTCTCGCAC GGACTACAAC                         40

(2) INFORMATION FOR SEQ ID NO: 8:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 8:

CTGAACGGTA GCATCTTGAC                                               20

(2) INFORMATION FOR SEQ ID NO: 9:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 9:

ACTGTTAGCT AATTGG                                                   16
```

```
(2) INFORMATION FOR SEQ ID NO: 10:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 10:

GGGCAATCGA GGGGGG                                                  16

(2) INFORMATION FOR SEQ ID NO: 11:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 11:

AAAGAAAAAA GACAGTACTA AATGGA                                       26

(2) INFORMATION FOR SEQ ID NO: 12:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 12:

TTTTTTATGT CAT                                                     13

(2) INFORMATION FOR SEQ ID NO: 13:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 13:

TTTTTTCTGT CAT                                                     13

(2) INFORMATION FOR SEQ ID NO: 14:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 14:

TTTTTTGTGT CAT                                                     13

(2) INFORMATION FOR SEQ ID NO: 15:

(i) SEQUENCE CHARACTERISTICS:
         (A) LENGTH: 13 base pairs
```

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

TTTTTTTTGT CAT                                                      13

(2) INFORMATION FOR SEQ ID NO: 16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

TTTTTCAGTC ATG                                                      13

(2) INFORMATION FOR SEQ ID NO: 17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

TTTTTCCGTC ATG                                                      13

(2) INFORMATION FOR SEQ ID NO: 18:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

TTTTTCGGTC ATG                                                      13

(2) INFORMATION FOR SEQ ID NO: 19:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

TTTTTCTGTC ATG                                                      13

(2) INFORMATION FOR SEQ ID NO: 20:

(i) SEQUENCE CHARACTERISTICS:
        (A) LENGTH: 13 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO: 20:

TTTTCTATCA TGA                                                     13

(2) INFORMATION FOR SEQ ID NO: 21:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

TTTTCTCTCA TGA                                                     13

(2) INFORMATION FOR SEQ ID NO: 22:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

TTTTCTGTCA TGA                                                     13

(2) INFORMATION FOR SEQ ID NO: 23:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

TTTTCTTTCA TGA                                                     13

(2) INFORMATION FOR SEQ ID NO: 24:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

NCCCAGGACG TGGAGGCGAT CACACCGCAG ACGTTGATCA ACATCCGGCC GGTGGTCGCC     60

GCGATCAAGG AGTTCTTCGG CACCAGCCAG CTGAGCCAAT TCATGGACCA GAACAACCCG    120

CTGTCGGGGT TGACCCACAA GCGCCGACTG TCGGCGCTGG GGCCCGGCGG TCTGTCACGT    180

GAGCGTGCCG GGCTGGAGGT CCGCGACGTG CACCCGTCGC ACTACGGCCG GATGTGCCCG    240

ATCGAAACCC TGAGGGGCC CAACATCGGT CTGATCGGCT CGCTGTCGGT GTACGCGCGG    300

GTCAACCCGT TCGGGTTCAT CGAAACGCCG TACCGCAAGG TGGTCGACGG CGTGGTTAGC    360

GACGAGATCG TGTACCTGAC CGCCGACGAG GAGGACCGCC ACGTGGTGGC ACAGGCCAAT    420

TCGCCGATCG ATGCGGACGG TCGCTTCGTC GAGCCGCGCG TGCTGGTCCG CCGCAAGGCG    480

```
GGCGAGGTGG AGTACGTGCC CTCGTCTGAG GTGGACTACA TGGACGTCTC GCCCCGCCAG      540

ATGGTGTCGG TGGCCACCGC GATGATTCCC TTCCTGGAGC ACGACGACGC CAACCGTGCC      600

CTCATGGGGG CAAACATGCA GCGCCAGGCG GTGCCGCTGG TCCGTAGCGA GGCCCCGCTG      660

GTGGGCACCG GGATGGAGCT GCGCGCGGCG ATCGACGCGG CGACGT                     706
```

(2) INFORMATION FOR SEQ ID NO: 25:

(i) SEQUENCE CHARACTERISTICS:
        (A) LENGTH: 706 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

```
NCCCAGGACG TGGAGGCGAT CACACCGCAG ACCCGCATCA ACATCCGGCG GGTCGTCGCC       60

GCGATCAAGG AGTTCTTCGG CACCAGCCAG CCCAKGTGGN TCATGGACCA GAACAACCCG      120

CTGTCGGTTC GGACCCACAA GCGTDNTHYG TCGGCGCTGG GGTCGGGTBG TCTGTCCCGT      180

GAGCGTGCGG GTGGNATDNA ANNTCACGTG CACCCGTCGC ACTACGGNCS CATGTGCCCG      240

ATCGAGAAAT KNGCCKNAGN BNTHVTCGGC CTGATCGGTT CGCTGTCGGT GTACGCGCGG      300

GTCAACCCGT TCGGCTTCCA VCNGNTNASN NTNNTGBDGR NGKGGNNSKC NACCHGDBGT      360

VAGYTNNKNT CNCVCHGCAC CGCCGACGAG GAGGACCGCC ACGTGGDGGC GCCGWNCAAC      420

TCGCCGNGNG MCNCGCGNGD GCTNCSTATT GGGCCGCGCG TTCTGGTCCG CCGCAGGGCG      480

GGCGAGGTGG AGTACGTGCC CTCGTCCGAG GTGGACTACA TGGACGTCTC CCCGCGCCAG      540

ATGGTGTCGG TGGGCACCGC GATGATTCCG DKCCBCSTAC ACGACGACGC CAACCGTGCC      600

CTGGNNNTTC DCMACATGCA GCGCCAGGCG GTTCCGGTCN TGSGCCNGHN NGCACCGCTG      660

GTGGGCACCG GCATGGAGTT GCGGGCGGCG ATCGACGCGG CGAANV                    706
```

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

```
GGACTTTGTG GGATACCCTC GCTT                                             24
```

(2) INFORMATION FOR SEQ ID NO: 27:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

```
GAAACAACCT ATGGG                                                       15
```

(2) INFORMATION FOR SEQ ID NO: 28:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

GAAACACCCT ATGGG                                                    15

(2) INFORMATION FOR SEQ ID NO: 29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

GAAACAGCCT ATGGG                                                    15

(2) INFORMATION FOR SEQ ID NO: 30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

GAAACATCCT ATGGG                                                    15

(2) INFORMATION FOR SEQ ID NO: 31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

AAACACNCTA TGGGA                                                    15

(2) INFORMATION FOR SEQ ID NO: 32:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

AACACCNTAT GGGAG                                                    15

(2) INFORMATION FOR SEQ ID NO: 33:

(i) SEQUENCE CHARACTERISTICS:
        (A) LENGTH: 15 base pairs
        (B) TYPE: nucleic acid
        (C) STRANDEDNESS: single -continued (D) TOPOLOGY: linear (ii) MOLECULE TYPE: cDNA (xi) SEQUENCE DESCRIPTION: SEQ ID NO: 33:

ACACCCNATG GGAGC                                                           15

(2) INFORMATION FOR SEQ ID NO: 34:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 34:

CAGCACACAC ACACCGCTGC TA                                                   22

(2) INFORMATION FOR SEQ ID NO: 35:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 35:

CAGCACACAC ANNCCGCTGC TA                                                   22

(2) INFORMATION FOR SEQ ID NO: 36:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 36:

CCCTTGACCA C                                                               11